United States Patent
Ying et al.

(10) Patent No.: US 12,377,163 B2
(45) Date of Patent: Aug. 5, 2025

(54) ANTI-B7H3 ANTIBODY-EXATECAN ANALOG CONJUGATE AND MEDICINAL USE THEREOF

(71) Applicants: JIANGSU HANSOH PHARMACEUTICAL GROUP CO., LTD, Jiangsu (CN); SHANGHAI HANSOH BIOMEDICAL CO., LTD, Shanghai (CN); CHANGZHOU HANSOH PHARMACEUTICAL CO., LTD, Jiangsu (CN)

(72) Inventors: Hua Ying, Shanghai (CN); Ling Zhang, Shanghai (CN); Ting Zhang, Shanghai (CN); Lei Zhang, Shanghai (CN); Jianyan Xu, Shanghai (CN); Weikang Tao, Shanghai (CN)

(73) Assignees: JIANGSU HANSOH PHARMACEUTICAL GROUP CO., LTD, Jiangsu (CN); SHANGHAI HANSOH BIOMEDICAL CO., LTD, Shanghai (CN); CHANGZHOU HANSOH PHARMACEUTICAL CO., LTD, Jiangsu (CN)

( * ) Notice: Subject to any disclaimer, the term of this patent is extended or adjusted under 35 U.S.C. 154(b) by 1164 days.

(21) Appl. No.: 17/281,062

(22) PCT Filed: Sep. 25, 2019

(86) PCT No.: PCT/CN2019/107852
§ 371 (c)(1),
(2) Date: Mar. 29, 2021

(87) PCT Pub. No.: WO2020/063673
PCT Pub. Date: Apr. 2, 2020

(65) Prior Publication Data
US 2021/0347894 A1 Nov. 11, 2021

(30) Foreign Application Priority Data
Sep. 30, 2018 (CN) .......................... 201811156667.5

(51) Int. Cl.
| | | |
|---|---|---|
| *A61K 47/68* | (2017.01) | |
| *A61K 31/4745* | (2006.01) | |
| *A61K 39/00* | (2006.01) | |
| *A61P 35/00* | (2006.01) | |
| *C07K 16/28* | (2006.01) | |

(52) U.S. Cl.
CPC ...... *A61K 47/6849* (2017.08); *A61K 31/4745* (2013.01); *A61K 47/68037* (2023.08); *A61P 35/00* (2018.01); *C07K 16/2827* (2013.01); *A61K 2039/505* (2013.01)

(58) Field of Classification Search
CPC ............ C07K 16/2827; C07K 2317/24; C07K 2317/77; C07K 2317/565; A61K 31/4745;
A61K 47/6803; A61K 47/6849; A61K 2039/505; A61K 47/68037; A61K 47/6889; A61K 47/65; A61P 35/00
See application file for complete search history.

(56) References Cited

U.S. PATENT DOCUMENTS

| | | | | |
|---|---|---|---|---|
| 2017/0362322 A1* | 12/2017 | DuBridge | .............. | C07K 16/30 |
| 2020/0031934 A1* | 1/2020 | Gu | ........................ | G01N 33/577 |
| 2021/0353764 A1* | 11/2021 | Xu | ......................... | C07K 16/18 |

FOREIGN PATENT DOCUMENTS

| | | |
|---|---|---|
| CN | 103333246 A | 10/2013 |
| CN | 104530235 A | 4/2015 |
| CN | 104755494 A | 7/2015 |
| CN | 105829346 A | 8/2016 |
| CN | 108066772 A | 5/2018 |
| WO | 2008066691 A2 | 6/2008 |
| WO | 2008100934 A1 | 8/2008 |
| WO | 2012147713 A1 | 11/2012 |
| WO | 2014057687 A1 | 4/2014 |
| WO | 2014061277 A1 | 4/2014 |
| WO | 2015184203 A1 | 3/2015 |
| WO | 2016044383 A1 | 3/2016 |

OTHER PUBLICATIONS

Cuzick, et al Lancet Oncol Jan. 2015; 16(1) 67-75 (Year: 2015).*
(Continued)

*Primary Examiner* — Julie Wu
*Assistant Examiner* — Sydney Van Druff
(74) *Attorney, Agent, or Firm* — Fish & Richardson P.C.

(57) ABSTRACT

Disclosed by the present invention are an anti-B7H3 antibody-exatecan analog conjugate, a preparation method therefor and an anti-tumor medicinal use thereof.

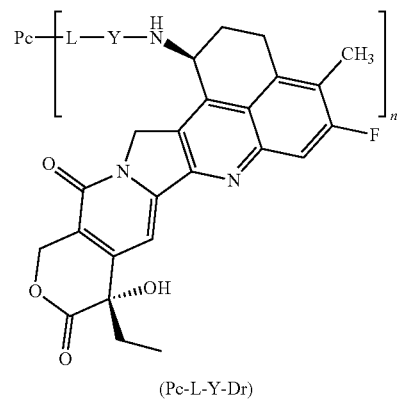

(Pc-L-Y-Dr)

40 Claims, 6 Drawing Sheets
Specification includes a Sequence Listing.

(56) References Cited

OTHER PUBLICATIONS

Shah, et al., World J Clin Oncol 2014 (Year: 2014).*
Selleckchem, et al., Dxd datasheet; https://www.selleckchem.com/datasheet/dxd-E289101-DataSheet.html ; First posted Oct. 15, 2016; Accessed 06/172024 (Year: 2016).*
MedChemExpress, et al., Exatecan product page; https://www.medchemexpress.com/exatecan.html ; first posted Feb. 3, 2018; Accessed Jun. 17, 2024 (Year: 2018).*
Li, et al., ACS Med. Chem. Lett. 2019, 10:1386 (Year: 2019).*
Chan, et al., PLoS ONE 2015 10(4) Article ID e0124708 (Year: 2015).*
Sela-Culang, et al., Front. In Immunol. 2013; vol. 4 Article 302 (Year: 2013).*
Y.-H. Zhou et al., "4IgB7-H3 is the major isoform expressed on immunocytes as well as malignant cells" Tissue Antigens, Aug. 2007, vol. 70, pp. 96-104.
Guangbo Zhang et al., "Diagnosis value of serum B7-H3 expression in non-small cell lung cancer" Lung Cancer, Nov. 2009, vol. 66(2), pp. 245-249.
Paul L. Crispen et al., "Tumor Cell and Tumor Vasculature Expression of B7-H3 Predict Survival in Clear Cell Renal Cell Carcinoma" Clinical Cancer Res., Aug. 15, 2008, vol. 14(16), pp. 5150-5157.
Timothy J. Roth et al., "B7-H3 Ligand Expression by Prostate Cancer: A Novel Marker of Prognosis and Potential Target for Therapy" Cancer Research, Aug. 15, 2007, vol. 67(16), pp. 7893-7900.
Xingxing Zang et al., "Tumor associated endothelial expression of B7-H3 predicts survival in ovarian carcinomas" Modern Pathology, Aug. 2010, vol. 23(8), pp. 1104-1112.
Kim Kramer et al., "Compartmental intrathecal radioimmunotherapy: results for treatment for metastatic CNS neuroblastoma" J Neurooncol (2010), vol. 97(3), pp. 409-418.
Titus Kretzschmar et al., "Antibody discovery: phage display" Current Opinion in Biotechnology, Dec. 2002, vol. 13(6), pp. 598-602.
Yusuke Ogitani et al., "DS-8201a, A Novel HER2-Targeting ADC with a Novel DNA Topoisomerase I Inhibitor, Demonstrates a Promising Antitumor Efficacy with Differentiation from T-DM1" Clinical Cancer Research, Oct. 15, 2016, vol. 22(20), pp. 5097-5108.
Yusuke Ogitani et al., "Bystander killing effect of DS-8201a, a novel anti-human epidermal growth factor receptor 2 antibody-drug conjugate, in tumors with human epidermal growth factor receptor 2 heterogeneity" Cancer Science, Jul. 2016, vol. 107(7), pp. 1039-1046.
Takashi Nakada et al., "Novel Antibody Drug Conjugates Containing Exatecan Derivative-based Cytotoxic Payloads" Bioorganic & Medicinal Chemistry Letters, Feb. 8, 2016, vol. 26, No. 6, pp. 1542-1545.

* cited by examiner

```
                        SEQUENCE LISTING

<160> NUMBER OF SEQ ID NOS: 17

<210> SEQ ID NO 1
<211> LENGTH: 534
<212> TYPE: PRT
<213> ORGANISM: Artificial Sequence
<220> FEATURE:
<223> OTHER INFORMATION: Synthetic Sequence_Human B7H3 full-length amino
      acid sequence

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320
```

```
Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
            485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
            515                 520                 525

Asp Gly Gln Glu Ile Ala
    530

<210> SEQ ID NO 2
<211> LENGTH: 316
<212> TYPE: PRT
<213> ORGANISM: Artificial Sequence
<220> FEATURE:
<223> OTHER INFORMATION: Synthetic Sequence_Mouse B7H3 full-length amino
      acid sequence

<400> SEQUENCE: 2

Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
            20                  25                  30

Val Ser Glu Asp Pro Val Val Ala Leu Val Asp Thr Asp Ala Thr Leu
            35                  40                  45

Arg Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
                85                  90                  95

Pro Asp Leu Leu Val Gln Gly Asn Ala Ser Leu Arg Leu Gln Arg Val
            100                 105                 110

Arg Val Thr Asp Glu Gly Ser Tyr Thr Cys Phe Val Ser Ile Gln Asp
            115                 120                 125

Phe Asp Ser Ala Ala Val Ser Leu Gln Val Ala Ala Pro Tyr Ser Lys
    130                 135                 140
```

```
Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Thr
            180                 185                 190

Ser Gln Met Ala Asn Glu Arg Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Leu Thr Phe Pro Pro Glu Ala Leu Trp Val Thr Val Gly Leu Ser
                245                 250                 255

Val Cys Leu Val Val Leu Leu Val Ala Leu Ala Phe Val Cys Trp Arg
            260                 265                 270

Lys Ile Lys Gln Ser Cys Glu Glu Asn Ala Gly Ala Glu Asp Gln
            275                 280                 285

Asp Gly Asp Gly Glu Gly Ser Lys Thr Ala Leu Arg Pro Leu Lys Pro
290                 295                 300

Ser Glu Asn Lys Glu Asp Asp Gly Gln Glu Ile Ala
305                 310                 315

<210> SEQ ID NO 3
<211> LENGTH: 223
<212> TYPE: PRT
<213> ORGANISM: Artificial Sequence
<220> FEATURE:
<223> OTHER INFORMATION: Synthetic Sequence_2Ig-B7H3

<400> SEQUENCE: 3

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Ala Glu Gly Gln Asp Gln Gly Ser Ala Tyr Ala Asn Arg
        50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
                100                 105                 110

Pro Tyr Ser Lys Pro Ser Met Thr Leu Glu Pro Asn Lys Asp Leu Arg
            115                 120                 125

Pro Gly Asp Thr Val Thr Ile Thr Cys Ser Ser Tyr Gln Gly Tyr Pro
130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190
```

```
Leu Val Arg Asn Pro Val Leu Gln Gln Asp Ala His Ser Ser Val Thr
            195                 200                 205

Ile Thr Pro Gln Arg Ser Pro Thr Gly His His His His His
    210                 215                 220
```

<210> SEQ ID NO 4
<211> LENGTH: 439
<212> TYPE: PRT
<213> ORGANISM: Artificial Sequence
<220> FEATURE:
<223> OTHER INFORMATION: Synthetic Sequence_4Ig-B7H3

<400> SEQUENCE: 4

```
Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
        35                  40                  45

His Ser Phe Ala Glu Gly Gln Asp Gln Gly Ser Ala Tyr Ala Asn Arg
    50                  55                  60

Thr Ala Leu Phe Pro Asp Leu Leu Ala Gln Gly Asn Ala Ser Leu Arg
65                  70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asp Thr Val Thr Ile Thr Cys Ser Ser Tyr Gln Gly Tyr Pro
    130                 135                 140

Glu Ala Glu Val Phe Trp Gln Asp Gly Gln Gly Val Pro Leu Thr Gly
145                 150                 155                 160

Asn Val Thr Thr Ser Gln Met Ala Asn Glu Gln Gly Leu Phe Asp Val
                165                 170                 175

His Ser Ile Leu Arg Val Val Leu Gly Ala Asn Gly Thr Tyr Ser Cys
            180                 185                 190

Leu Val Arg Asn Pro Val Leu Gln Gln Asp Ala His Ser Ser Val Thr
        195                 200                 205

Ile Thr Pro Gln Arg Ser Pro Thr Gly Ala Val Glu Val Gln Val Pro
    210                 215                 220

Glu Asp Pro Val Val Ala Leu Val Gly Thr Asp Ala Thr Leu Arg Cys
225                 230                 235                 240

Ser Phe Ser Pro Glu Pro Gly Phe Ser Leu Ala Gln Leu Asn Leu Ile
                245                 250                 255

Trp Gln Leu Thr Asp Thr Lys Gln Leu Val His Ser Phe Thr Glu Gly
            260                 265                 270

Arg Asp Gln Gly Ser Ala Tyr Ala Asn Arg Thr Ala Leu Phe Pro Asp
        275                 280                 285

Leu Leu Ala Gln Gly Asn Ala Ser Leu Arg Leu Gln Arg Val Arg Val
    290                 295                 300

Ala Asp Glu Gly Ser Phe Thr Cys Phe Val Ser Ile Arg Asp Phe Gly
305                 310                 315                 320

Ser Ala Ala Val Ser Leu Gln Val Ala Ala Pro Tyr Ser Lys Pro Ser
                325                 330                 335
```

```
Met Thr Leu Glu Pro Asn Lys Asp Leu Arg Pro Gly Asp Thr Val Thr
            340                 345                 350

Ile Thr Cys Ser Ser Tyr Arg Gly Tyr Pro Glu Ala Glu Val Phe Trp
            355                 360                 365

Gln Asp Gly Gln Gly Val Pro Leu Thr Gly Asn Val Thr Thr Ser Gln
370                 375                 380

Met Ala Asn Glu Gln Gly Leu Phe Asp Val His Ser Val Leu Arg Val
385                 390                 395                 400

Val Leu Gly Ala Asn Gly Thr Tyr Ser Cys Leu Val Arg Asn Pro Val
                405                 410                 415

Leu Gln Gln Asp Ala His Gly Ser Val Thr Ile Thr Gly Gln Pro Met
            420                 425                 430

Thr His His His His His His
            435

<210> SEQ ID NO 5
<211> LENGTH: 222
<212> TYPE: PRT
<213> ORGANISM: Artificial Sequence
<220> FEATURE:
<223> OTHER INFORMATION: Synthetic Sequence_Mouse B7H3 antigen for
      screening and detection

<400> SEQUENCE: 5

Val Glu Val Gln Val Ser Glu Asp Pro Val Ala Leu Val Asp Thr
1               5                   10                  15

Asp Ala Thr Leu Arg Cys Ser Phe Ser Pro Glu Pro Gly Phe Ser Leu
            20                  25                  30

Ala Gln Leu Asn Leu Ile Trp Gln Leu Thr Asp Thr Lys Gln Leu Val
            35                  40                  45

His Ser Phe Thr Glu Gly Arg Asp Gln Gly Ser Ala Tyr Ser Asn Arg
        50                  55                  60

Thr Ala Leu Phe Pro Asp Leu Leu Val Gln Gly Asn Ala Ser Leu Arg
65                  70                  75                  80

Leu Gln Arg Val Arg Val Thr Asp Glu Gly Ser Tyr Thr Cys Phe Val
                85                  90                  95

Ser Ile Gln Asp Phe Asp Ser Ala Ala Val Ser Leu Gln Val Ala Ala
            100                 105                 110

Pro Tyr Ser Lys Pro Ser Met Thr Leu Glu Pro Asn Lys Asp Leu Arg
            115                 120                 125

Pro Gly Asn Met Val Thr Ile Thr Cys Ser Ser Tyr Gln Gly Tyr Pro
    130                 135                 140

Glu Ala Glu Val Phe Trp Lys Asp Gly Gln Gly Val Pro Leu Thr Gly
145                 150                 155                 160

Asn Val Thr Thr Ser Gln Met Ala Asn Glu Arg Gly Leu Phe Asp Val
                165                 170                 175

His Ser Val Leu Arg Val Leu Gly Ala Asn Gly Thr Tyr Ser Cys
            180                 185                 190

Leu Val Arg Asn Pro Val Leu Gln Gln Asp Ala His Gly Ser Val Thr
            195                 200                 205

Ile Thr Gly Gln Pro Leu Thr Phe His His His His His
        210                 215                 220

<210> SEQ ID NO 6
<211> LENGTH: 119
<212> TYPE: PRT
```

```
<213> ORGANISM: Artificial Sequence
<220> FEATURE:
<223> OTHER INFORMATION: Synthetic Sequence_Heavy chain variable
      sequence of 1702

<400> SEQUENCE: 6

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ala Arg Leu Tyr Ala Ser Phe Asp Tyr Trp Gly Gln Gly
            100                 105                 110

Ala Leu Val Thr Val Ser Ser
        115

<210> SEQ ID NO 7
<211> LENGTH: 110
<212> TYPE: PRT
<213> ORGANISM: Artificial Sequence
<220> FEATURE:
<223> OTHER INFORMATION: Synthetic Sequence_Light chain variable
      sequence of 1702

<400> SEQUENCE: 7

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu
            100                 105                 110

<210> SEQ ID NO 8
<211> LENGTH: 8
<212> TYPE: PRT
<213> ORGANISM: Artificial Sequence
<220> FEATURE:
<223> OTHER INFORMATION: Synthetic Sequence_1702 HCDR1

<400> SEQUENCE: 8

Gly Phe Ile Phe Ser Ser Ser Ala
1               5

<210> SEQ ID NO 9
<211> LENGTH: 8
```

```
<212> TYPE: PRT
<213> ORGANISM: Artificial Sequence
<220> FEATURE:
<223> OTHER INFORMATION: Synthetic Sequence_1702 HCDR2

<400> SEQUENCE: 9

Ile Ser Tyr Asp Gly Ser Asn Lys
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic Sequence_1702 HCDR3

<400> SEQUENCE: 10

Ala Arg Ser Ala Arg Leu Tyr Ala Ser Phe Asp Tyr
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Sequence_1702 LCDR1

<400> SEQUENCE: 11

Ser Gly Ser Val Ser Thr Ser His Tyr
1               5

<210> SEQ ID NO 12

<400> SEQUENCE: 12

000

<210> SEQ ID NO 13
<211> LENGTH: 10
<212> TYPE: PRT
<213> ORGANISM: Artificial Sequence
<220> FEATURE:
<223> OTHER INFORMATION: Synthetic Sequence_1702 LCDR3

<400> SEQUENCE: 13

Ala Ile His Val Asp Arg Asp Ile Trp Val
1               5                   10

<210> SEQ ID NO 14
<211> LENGTH: 449
<212> TYPE: PRT
<213> ORGANISM: Artificial Sequence
<220> FEATURE:
<223> OTHER INFORMATION: Synthetic Sequence_Heavy chain (IgG1) amino
      acid sequence of 1702

<400> SEQUENCE: 14

Gln Val Gln Leu Val Gln Ser Gly Gly Gly Val Val Gln Pro Gly Thr
1               5                   10                  15

Ser Leu Arg Leu Ser Cys Ala Ala Ser Gly Phe Ile Phe Ser Ser Ser
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Val Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ala Arg Leu Tyr Ala Ser Phe Asp Tyr Trp Gly Gln Gly
            100                 105                 110

Ala Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 15
<211> LENGTH: 216
<212> TYPE: PRT
<213> ORGANISM: Artificial Sequence
```

```
<220> FEATURE:
<223> OTHER INFORMATION: Synthetic Sequence_Light chain amino acid
      sequence of 1702

<400> SEQUENCE: 15

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 16
<211> LENGTH: 215
<212> TYPE: PRT
<213> ORGANISM: Artificial Sequence
<220> FEATURE:
<223> OTHER INFORMATION: Synthetic Sequence_Light chain sequence of
      1702DS after mutation modification

<400> SEQUENCE: 16

Asp Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu Gly Gln
            100                 105                 110
```

```
Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys
    210                 215

<210> SEQ ID NO 17
<211> LENGTH: 110
<212> TYPE: PRT
<213> ORGANISM: Artificial Sequence
<220> FEATURE:
<223> OTHER INFORMATION: Synthetic Sequence_Light Chain Variable Region
      of h1702DS

<400> SEQUENCE: 17

Asp Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

His Tyr Pro Ser Trp Tyr Gln Gln Thr Pro Gly Gln Ala Pro Arg Met
        35                  40                  45

Leu Ile Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Ile His Val Asp Arg
                85                  90                  95

Asp Ile Trp Val Phe Gly Gly Gly Thr Lys Leu Thr Val Leu
                100                 105                 110
```

ANTI-B7H3 ANTIBODY-EXATECAN ANALOG CONJUGATE AND MEDICINAL USE THEREOF

CROSS-REFERENCE TO RELATED APPLICATIONS

This application is the national stage of International Patent Application No. PCT/CN2019/107852, filed Sep. 25, 2019, which claims the benefit of and priority to Chinese Patent Application No. 201811156667.5, filed Sep. 30, 2018, each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 8, 2024, is named "719075CPUS 126268-5014-US_Sequence_Listing.TXT" and is 27 kilobytes in size.

FIELD OF THE INVENTION

The present disclosure relates to an anti-B7H3 antibody-exatecan analog conjugate, a method for preparing the same, a pharmaceutical composition comprising the same, and a use thereof in the preparation of medicaments for the treatment of B7H3-mediated diseases or disorders, especially a use thereof in the preparation of an anti-cancer drug.

BACKGROUND OF THE INVENTION

The T cell-mediated immune response plays an extremely important role in anti-tumor processes of an organism. However, the activation and proliferation of T cells requires not only an antigen signal recognized by TCR, but also a second signal provided by co-stimulatory molecules. The molecules of the B7 family belong to the co-stimulatory molecule immunoglobulin superfamily. More and more studies have shown that molecules of this family play an important regulatory role in the normal immune function and pathological state in an organism.

B7H3 is a member of B7 family and is a type I transmembrane protein, which contains a signal peptide at the amino terminus, an extracellular immunoglobulin-like variable region (IgV) and constant region (IgC), a transmembrane region, and a cytoplasmic tail region having 45 amino acids (Tissue Antigens. 2007 August; 70(2): 96-104). B7H3 has two kinds of splicing variants, B7H3a and B7H3b. The extracellular domain of B7H3a consists of two immunoglobulin domains of IgV-IgC (also known as 2IgB7H3), and the extracellular domain of B7H3b consists of four immunoglobulin domains of IgV-IgC-IgV-IgC (also known as 4IgB7H3).

B7H3 protein is not expressed or is poorly expressed in normal tissues and cells, but highly expressed in various tumor tissues and is closely correlated with tumor progression, patient survival and prognosis. It has been clinically reported that B7H3 is over-expressed in many types of cancers, especially in non-small cell lung cancer, renal cancer, urinary tract epithelial cancer, colorectal cancer, prostate cancer, glioblastoma multiforme, ovarian cancer and pancreas cancer (Lung Cancer. 2009 November; 66(2): 245-249; Clin Cancer Res. 2008 Aug. 15; 14(16): 5150-5157). In addition, it has also been reported in the literature that, in prostate cancer, the expression level of B7H3 is positively correlated with clinical pathological malignancy (such as tumor volume, extra-prostatic invasion or Gleason score), and is also associated with cancer progression (Cancer Res. 2007 Aug. 15; 67(16):7893-7900). Similarly, in glioblastoma multiforme, the expression of B7H3 is inversely associated with event-free survival, and in pancreatic cancer, the expression of B7H3 is associated with lymph node metastasis and pathological progression. Therefore, B7H3 is considered as a new tumor marker and potential therapeutic target.

Currently, there have been therapeutic strategies specific for B7H3 target for preclinical studies. For example, antibodies targeting murine B7H3 will enhance infiltrative CD8-positive T cells in tumors and inhibit tumor growth (Mod Pathol. 2010 August; 23(8): 1104-1112). Furthermore, patent application WO 2008/066691 shows that antibodies recognizing the B7H3 variant, B7-H3a, exhibited an in vivo anti-tumor effect on adenocarcinoma. In clinical studies, a drug of murine B7H3 antibody conjugated with radioactive $I^{131}$ significantly inhibited the growth of neuroblastoma in patients [J Neufooocol 97(3):409-18 (2010)]. However, the projects currently under study are humanized antibodies that have been engineered by humanization of murine antibodies. Humanized antibodies upon immunization have higher immunogenicity risk, which is an unfavorable factor in human application.

Phage display technology refers to the fusion of an exogenous protein or polypeptide with a phage coat protein, so as to express an exogenous protein on the surface of the phage particles. The phage antibody library is an antibody library established by combining phage display technology, PCR amplification technology and protein expression technology through comprehensive technical means.

The biggest advantage of the phage antibody library is to prepare a fully humanized antibody by mimicking the three processes of antibody production in vivo without animal immunization. In addition, the phage antibody library has the following advantages: 1) the unification of genotype and phenotype is achieved; in addition, the experimental method is simple and rapid; the traditional antibody production method by hybridoma technology takes several months, while the antibody library technology takes only a few weeks; 2) The expressed product is a fully humanized antibody, and the antibody is mainly expressed in the form of active fragments Fab and scFv. With the small molecular weight, the expressed antibody has obvious advantages in tissue penetrability compared with intact antibody; 3) Screening capacity is large; hybridoma technology is used to screen among thousands of clones, while antibody library technology can be used to select from millions or even hundreds of millions of molecules; therefore, more diversified antibodies will be obtained; 4) wide application; prokaryotic expression system is used, which leads to more obvious advantage in large scale production (Curr Opin Biotechnol. 2002 December; 13(6):598-602; Immunotechnology, 2013, 48(13) 48(13): 63-73).

Antibody drug conjugates (ADCs) enable combining a monoclonal antibody or an antibody fragment with a biologically active cytotoxin through a chemically stable linker, taking full advantage of the specificity of antibody binding to the surface antigens of normal cells or tumor cells and the high efficiency of the cytotoxin, while avoiding low efficacy of the antibody and the toxic side effect of the cytotoxin. That means, comparing with conventional chemotherapy drugs, antibody drug conjugates can accurately bind to tumor cells and reduce the affect to normal cells.

At present, a variety of ADC drugs have been used in clinical or clinical research. For example, Kadcyla is an ADC drug formed by trastuzumab targeting Her2 and DM1. At the same time, there are also patent applications that report antibodies and ADC drugs targeting B7H3, such as WO2008100934, WO2012147713, WO2014061277, WO2015184203 and WO2016044383.

There are several types of cytotoxic small molecules used in antibody drug conjugate, one of which is camptothecin derivatives, which show anti-tumor effect by inhibiting topoisomerase I. Documents reporting the use of the camptothecin derivative, exatecan (chemical name: (1S,9S)-1-amino-9-ethyl-5-fluoro-2,3-dihydro-9-hydroxy-4-methyl-1H,12H-benzo[de]pyrano[3',4':6,7]imidazo[1,2-b]quinoline-10,13(9H,15H)-dione) in antibody drug conjugate (ADC) comprise WO2014057687, *Clinical Cancer Research* (2016) 22 (20): 5097-5108, and *Cancer Sci* (2016) 107: 1039-1046. However, further development of ADC drugs with better efficacy is still needed.

SUMMARY OF THE INVENTION

The present disclosure relates to an ADC of anti-B7H3 antibody and a use thereof, and provides an ADC drug formed by conjugating a monoclonal antibody or antigen-binding fragment to a cytotoxic exatecan analogs, wherein the monoclonal antibody or antigen-binding fragment binds to the amino acid sequence or three-dimensional structure of the extracellular region of B7H3.

Therefore, the object of the present disclosure is to provide a ligand-drug conjugate of formula (Pc-L-Y-Dr) or a pharmaceutically acceptable salt or solvate thereof:

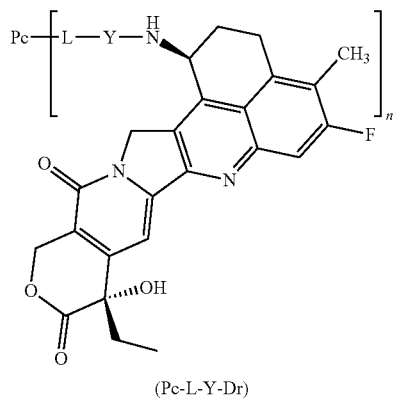

(Pc-L-Y-Dr)

wherein:

Y is selected from the group consisting of —O—$(CR^aR^b)_m$—, —$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen atom, deuterium atom, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$ together with the carbon atom to which they are attached form a cycloalkyl or heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl;

$R^2$ is selected from the group consisting of hydrogen atom, halogen, haloalkyl, deuterated alkyl, cycloalkyl, cycloalkylalkyl, alkoxyalkyl, heterocyclyl, aryl and heteroaryl;

or, $R^1$ and $R^2$ together with the carbon atom to which they are attached form a cycloalkyl or heterocyclyl;

or, $R^a$ and $R^2$ together with the carbon atom to which they are attached form a cycloalkyl or heterocyclyl;

m is an integer from 0 to 4;

n is 1 to 10, optionally selected from about 1, 2, 3, 4, 5, 6, 7, 8, 9, 10; n can be an integer or a decimal;

L is a linker unit;

Pc is an anti-B7H3 antibody or an antigen-binding fragment thereof.

In some embodiments of the present disclosure, in the provided ligand-drug conjugate of formula (Pc-L-Y-Dr) or the pharmaceutically acceptable salt or solvate thereof, the anti-B7H3 antibody or the antigen-binding fragment thereof comprises:

the heavy chains HCDR1, HCDR2 and HCDR3 represented by amino acid sequences of SEQ ID NOs: 8, 9 and 10 respectively, or HCDR variants having 3, 2 or 1 amino acid difference(s) from HCDR1, HCDR2 and HCDR3 represented by SEQ ID NOs: 8, 9 and 10 respectively; and the light chains LCDR1, LCDR2 and LCDR3 represented by amino acid sequences of SEQ ID NOs: 11, 12 and 13 respectively, or LCDR variants having 3, 2 or 1 amino acid difference(s) from LCDR1, LCDR2 and LCDR3 represented by SEQ ID NOs: 11, 12 and 13 respectively.

In some embodiments of the present disclosure, in the ligand-drug conjugate of formula (Pc-L-Y-Dr) or the pharmaceutically acceptable salt or solvate thereof, the light chain FR region on the light chain variable region of the anti-B7H3 antibody or the antigen-binding fragment thereof is derived from the human germline light chain sequence or the mutant sequence thereof, and/or the heavy chain FR region on the heavy chain variable region is derived from the human germline heavy chain sequence or the mutant sequence thereof.

In some embodiments of the present disclosure, in the ligand-drug conjugate of formula (Pc-L-Y-Dr) or the pharmaceutically acceptable salt or solvate thereof, the anti-B7H3 antibody or the antigen-binding fragment thereof comprises a heavy chain variable region and/or a light chain variable region selected from the follows:

the amino acid sequence of the heavy chain variable region is represented by SEQ ID NO: 6 or has at least 95% sequence identity with SEQ ID NO: 6, the amino acid sequence of the light chain variable region is represented by SEQ ID NO: 7 or has at least 95% sequence identity with SEQ ID NO: 7.

In some embodiments of the present disclosure, in the ligand-drug conjugate of formula (Pc-L-Y-Dr) or the pharmaceutically acceptable salt or solvate thereof, the anti-B7H3 antibody or the antigen-binding fragment thereof comprises an antibody constant region; the heavy chain constant region of the antibody constant region is derived from human IgG1, IgG2, IgG3 or IgG4 or has at least 95% sequence identity with them, the light chain constant region of the antibody constant region is derived from a human antibody κ, λ chain or has at least 95% sequence identity with them; and preferably, the amino acid sequence of the heavy chain constant region is derived from human IgG1 or has at least 95% sequence identity with it.

In some embodiments of the present disclosure, in the ligand-drug conjugate of formula (Pc-L-Y-Dr) or the pharmaceutically acceptable salt or solvate thereof, Pc is a full-length antibody; wherein the full-length antibody is selected from the group consisting of:
  the h1702 antibody consisting of the heavy chain sequence represented by SEQ ID NO: 14 and the light chain sequence represented by SEQ ID NO: 15, and
  the h1702DS antibody consisting of the heavy chain sequence represented by SEQ ID NO: 14 and the light chain sequence represented by SEQ ID NO: 16.

In some embodiments of the present disclosure, in the ligand-drug conjugate of formula (Pc-L-Y-Dr) or the pharmaceutically acceptable salt or solvate thereof, the antigen-binding fragment is selected from the group consisting of Fab, Fab', F(ab')2, single-chain antibodies (scFv), dimerized V regions (double antibody), disulfide stabilized V regions (dsFv), and antigen-binding fragments of peptides containing CDRs.

In some embodiments of the present disclosure, in the ligand-drug conjugate of formula (Pc-L-Y-Dr) or the pharmaceutically acceptable salt or solvate thereof, $R^1$ is a haloalkyl or $C_{3-6}$ cycloalkyl.

In some embodiments of the present disclosure, in the ligand-drug conjugate of formula (Pc-L-Y-Dr) or the pharmaceutically acceptable salt or solvate thereof, $R^2$ is a hydrogen atom.

In some embodiments of the present disclosure, in the ligand-drug conjugate of formula (Pc-L-Y-Dr) or the pharmaceutically acceptable salt or solvate thereof, $R^1$ is a $C_{3-6}$ cycloalkyl; and $R^2$ is a hydrogen atom.

In some embodiments of the present disclosure, the ligand-drug conjugate of formula (Pc-L-Y-Dr) or the pharmaceutically acceptable salt or solvate thereof, wherein:
  Y is —O—(CR$^a$R$^b$)$_m$—CR$^1$R$^2$—C(O)—;
  $R^a$ and $R^b$ are identical or different and are each independently selected from the group consisting of hydrogen atom, deuterium atom, halogen and alkyl;
  $R^1$ is a haloalkyl or $C_{3-6}$ cycloalkyl;
  $R^2$ is selected from the group consisting of hydrogen atom, haloalkyl or $C_{3-6}$ cycloalkyl;
  or, $R^1$ and $R^2$ together with the carbon atom to which they are attached form a $C_{3-6}$ cycloalkyl;
  m is 0 or 1.

In some embodiments of the present disclosure, the ligand-drug conjugate of formula (Pc-L-Y-Dr) or the pharmaceutically acceptable salt or solvate thereof, wherein:
  Y is —O—(CR$^b$)$_m$—CR$^1$R$^2$—C(O)—;
  $R^a$ and $R^b$ are identical or different and are each independently selected from the group consisting of hydrogen atom, deuterium atom, halogen and alkyl;
  $R^1$ is a $C_{3-6}$ cycloalkyl;
  $R^2$ is a hydrogen atom;
  or, $R^1$ and $R^2$ together with the carbon atom to which they are attached form a $C_{3-6}$ cycloalkyl; m is 0.

In some embodiments of the present disclosure, in the ligand-drug conjugate of formula (Pc-L-Y-Dr) or the pharmaceutically acceptable salt or solvate thereof, Y is selected from the group consisting of:

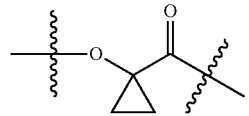

-continued

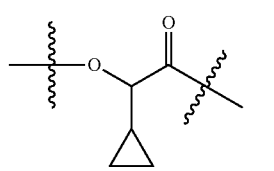

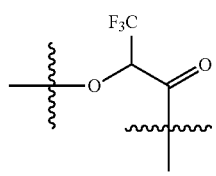

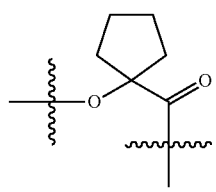

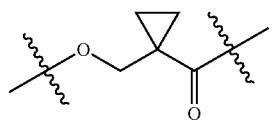

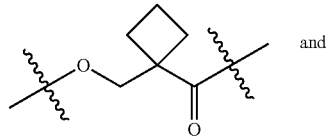

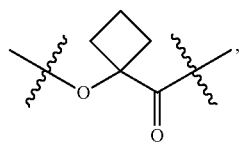

and preferably

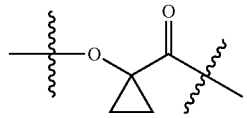

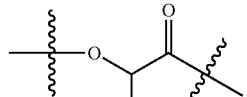

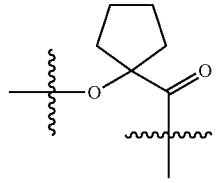

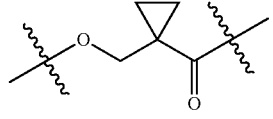

-continued

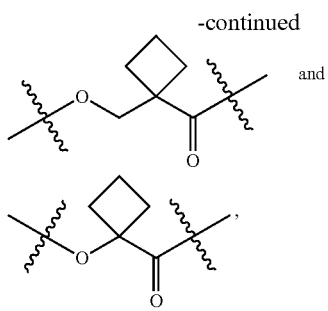

and and most preferably

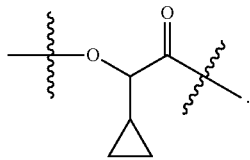 [SMILES: *OC(C(*)=O)C1CC1]

In some embodiments of the present disclosure, in the ligand-drug conjugate of formula (Pc-L-Y-Dr) or the pharmaceutically acceptable salt or solvate thereof, the O terminal of Y is connected to the linker unit L.

In some embodiments of the present disclosure, in the ligand-drug conjugate of formula (Pc-L-Y-Dr) or the pharmaceutically acceptable salt or solvate thereof, n is 2 to 8, preferably 5 to 9, and most preferably 7.5; and non-limiting examples include 3, 4, 5, 6, 7.2, 7.5, 8, 8.5, 9.

In some embodiments of the present disclosure, in the ligand-drug conjugate of formula (Pc-L-Y-Dr) or the pharmaceutically acceptable salt or solvate thereof, the linker unit -L- is -$L^1$-$L^2$-$L^3$-$L^4$-, $L^1$ is

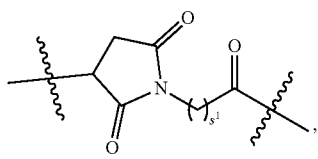

and $s^1$ is an integer from 2 to 8;

$L^2$ is a chemical bond;
$L^3$ is a tetrapeptide residue;
$L^4$ is —$NR^5(CR^6R^7)t$-, $R^5$, $R^6$ and $R^7$ are identical or different and are each independently selected from the group consisting of hydrogen atom and alkyl, and t is 1 or 2.

In some embodiments of the present disclosure, in the ligand-drug conjugate of formula (Pc-L-Y-Dr) or the pharmaceutically acceptable salt or solvate thereof, the $L^1$ terminal of the linker unit -L- is connected to the ligand, and the $L^4$ terminal of the linker unit -L- is connected to Y.

In some embodiments of the present disclosure, in the ligand-drug conjugate of formula (Pc-L-Y-Dr) or the pharmaceutically acceptable salt or solvate thereof, the tetrapeptide residue of $L^3$ is an amino acid residue composed of two or more amino acids selected from the group consisting of phenylalanine (E), glycine (G), valine (V), lysine (K), citrulline, serine (S), glutamic acid (E) and aspartic acid (N), and preferably a tetrapeptide residue of GGFG (glycine-glycine-phenylalanine-glycine).

In some embodiments of the present disclosure, in the ligand-drug conjugate of formula (Pc-L-Y-Dr) or the pharmaceutically acceptable salt or solvate thereof, -L-Y- is a structure as follows:

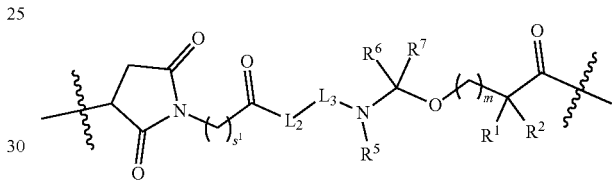

$L^2$ is a chemical bond;
$L^3$ is a tetrapeptide residue of GGFG;
$R^1$ is a haloalkyl or $C_{3-6}$ cycloalkyl;
$R^2$ is selected from the group consisting of hydrogen atom, haloalkyl or $C_{3-6}$ cycloalkyl;
or, $R^1$ and $R^2$ together with the carbon atom to which they are attached form a $C_{3-6}$ cycloalkyl;
$R^5$, $R^6$ and $R^7$ are identical or different and are each independently selected from the group consisting of hydrogen atom and alkyl;
$s^1$ is an integer from 2 to 8;
m is an integer from 0 to 4.

In some embodiments of the present disclosure, in the ligand-drug conjugate of formula (Pc-L-Y-Dr) or the pharmaceutically acceptable salt or solvate thereof, -L-Y- is selected from the group consisting of:

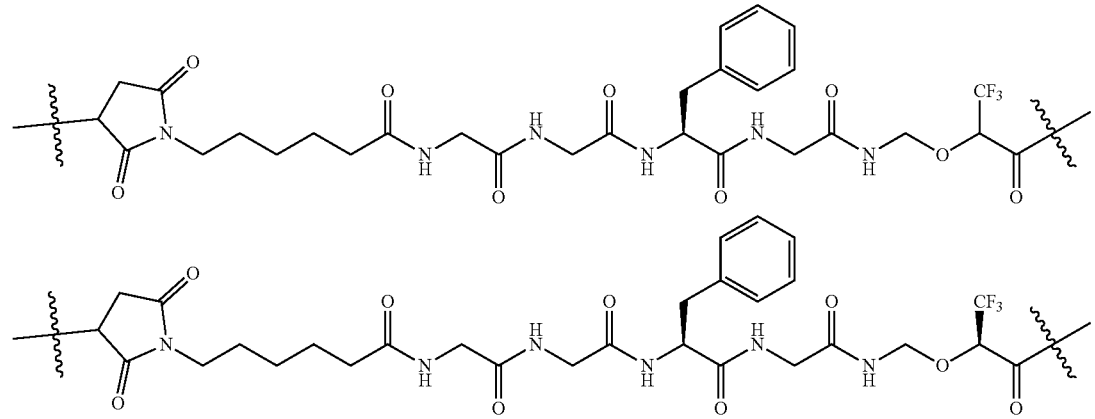

-continued
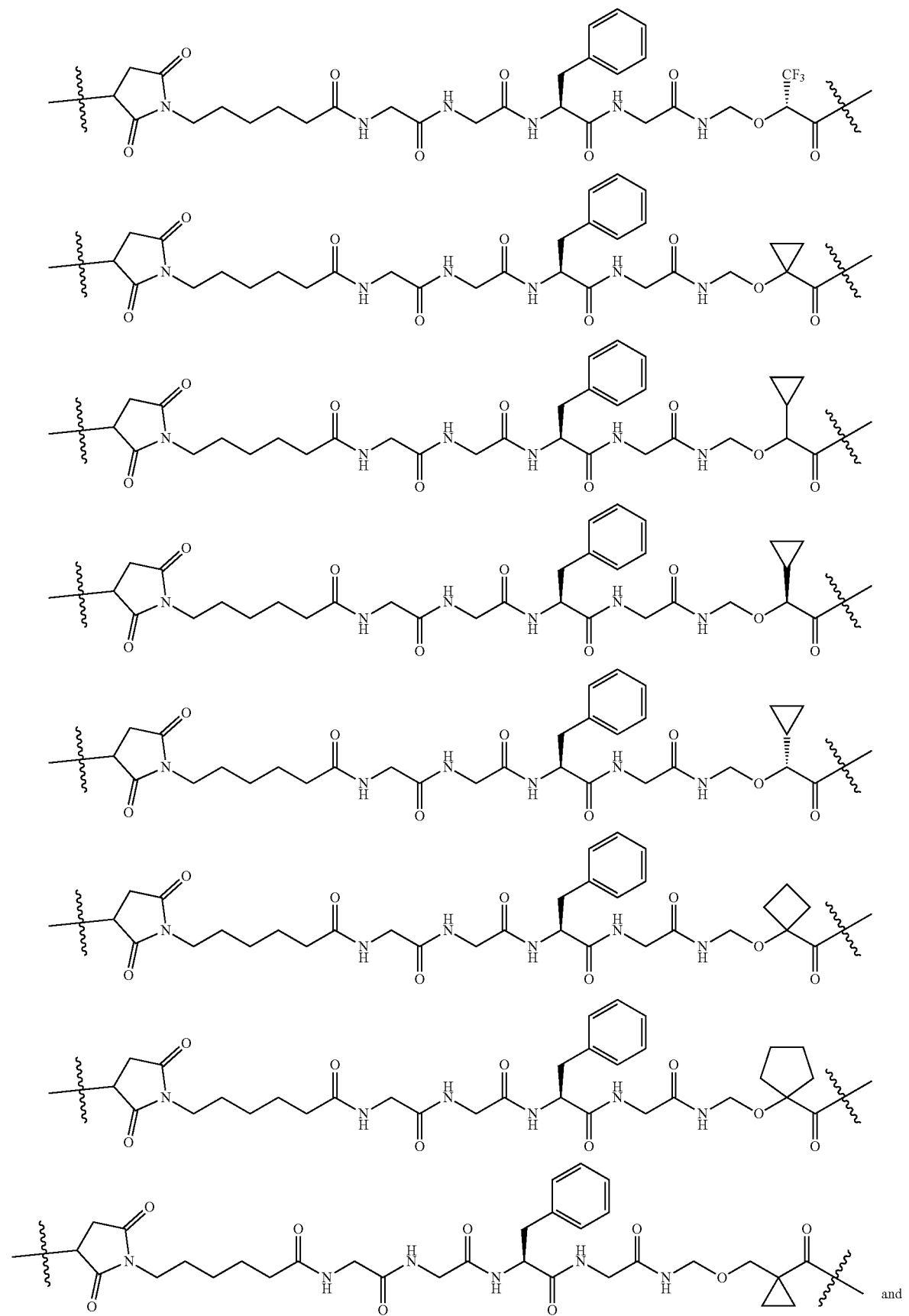
and

-continued

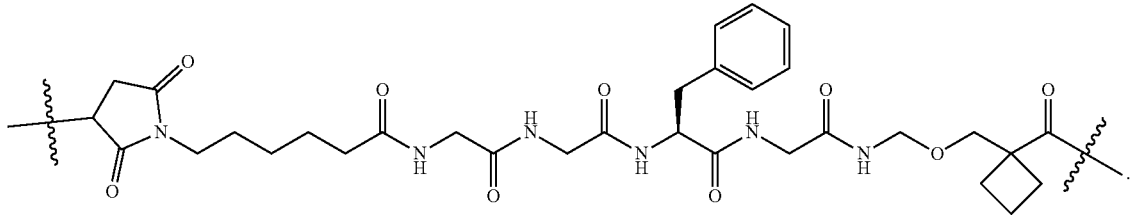

In some embodiments of the present disclosure, the ligand-drug conjugate of formula (Pc-L-Y-Dr) or the pharmaceutically acceptable salt or solvate thereof is a ligand-drug conjugate of formula (Pc-$L_a$-Y-Dr) or a pharmaceutically acceptable salt or solvate:

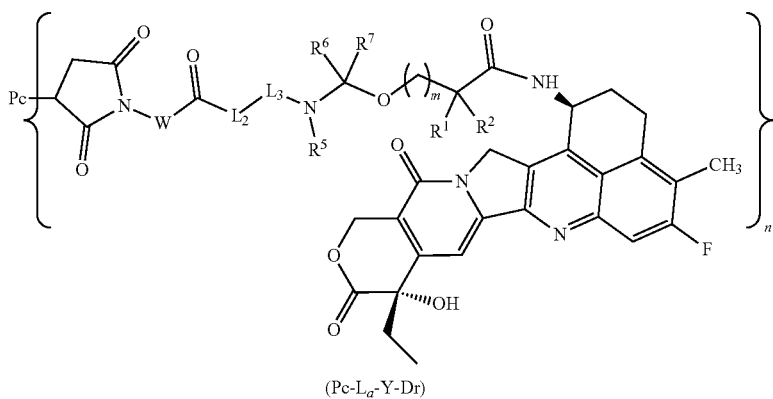

(Pc-$L_a$-Y-Dr)

wherein:

W is selected from the group consisting of $C_{1-8}$ alkyl, $C_{1-8}$ alkyl-cycloalkyl and linear heteroalkyl comprising 1 to 8 atom(s), the heteroalkyl comprises 1 to 3 heteroatom(s) selected from the group consisting of N, O and S, wherein the $C_{1-8}$ alkyl, cycloalkyl and linear heteroalkyl are each independently optionally further substituted by one or more substituent(s) selected from the group consisting of halogen, hydroxy, cyano, amino, alkyl, chloroalkyl, deuterated alkyl, alkoxy and cycloalkyl;

$L^2$ is selected from the group consisting of —$NR^4$ $(CH_2CH_2O)_{p1}CH_2CH_2C(O)$—, —$NR^4(CH_2CH_2O)_{p1}$ $CH_2C(O)$—, —$S(CH_2)_{p1}C(O)$— and a chemical bond, $p^1$ is an integer from 1 to 20, and preferably 1 to 6;

$L^3$ is a peptide residue composed of 2 to 7 amino acids, the amino acid can be substituted or unsubstituted, when substituted, the substituent group(s) can be substituted at any available connection point, the substituent group(s) is one or more group(s) independently selected from the group consisting of halogen, hydroxy, cyano, amino, alkyl, chloroalkyl, deuterated alkyl, alkoxy and cycloalkyl;

$R^1$ is selected from the group consisting of halogen, haloalkyl, deuterated alkyl, cycloalkyl, heterocyclyl, aryl and heteroaryl;

$R^2$ is selected from the group consisting of hydrogen atom, halogen, haloalkyl, deuterated alkyl, cycloalkyl, heterocyclyl, aryl and heteroaryl;

or, $R^1$ and $R^2$ together with the carbon atom to which they are attached form a cycloalkyl or heterocyclyl;

$R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

m is an integer from 0 to 4;

n is 1 to 10, which can be an integer or a decimal;

Pc is an anti-B7H3 antibody or an antigen-binding fragment thereof.

In some embodiments of the present disclosure, the ligand-drug conjugate of formula (Pc-L-Y-Dr) or the pharmaceutically acceptable salt or solvate thereof is a ligand-drug conjugate of formula (Pc-$L_b$-Y-Dr) or a pharmaceutically acceptable salt or solvate:

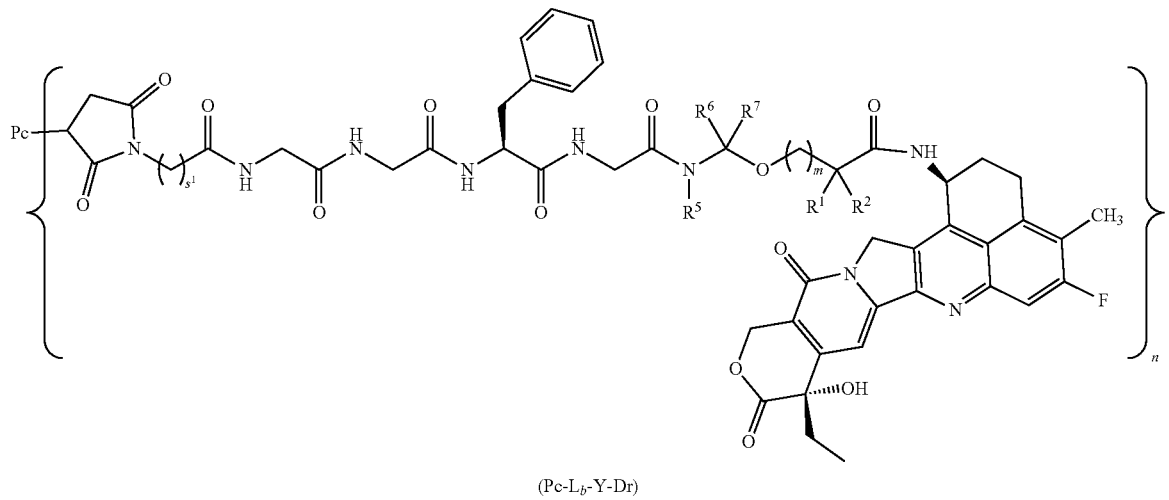
(Pc-L_b-Y-Dr)
wherein:
$s^1$ is an integer from 2 to 8, and preferably 5;
$R^1$, $R^2$, $R^5\sim R^7$, m and n are as defined in formula (Pc-L_a-Y-Dr).
In some embodiments of the present disclosure, in the ligand-drug conjugate of formula (Pc-L-Y-Dr) or the pharmaceutically acceptable salt or solvate thereof, the ligand-drug conjugate is selected from the group consisting of:
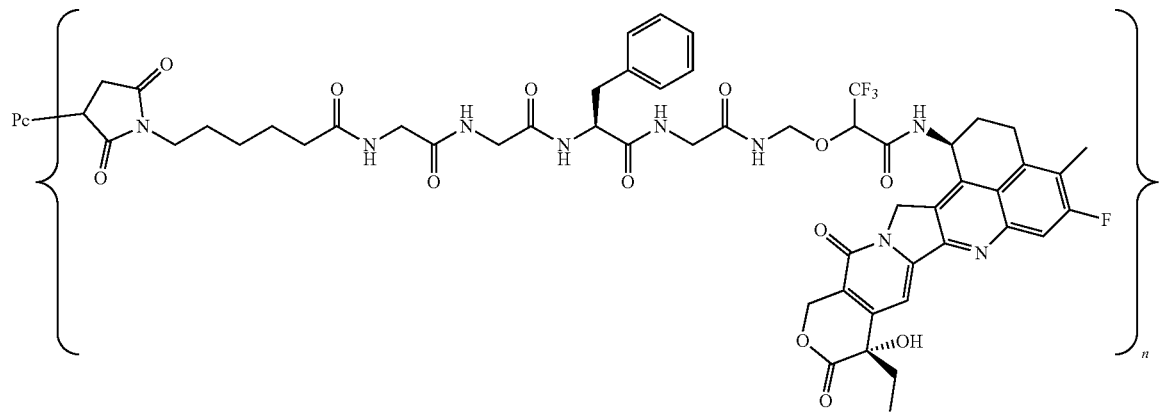
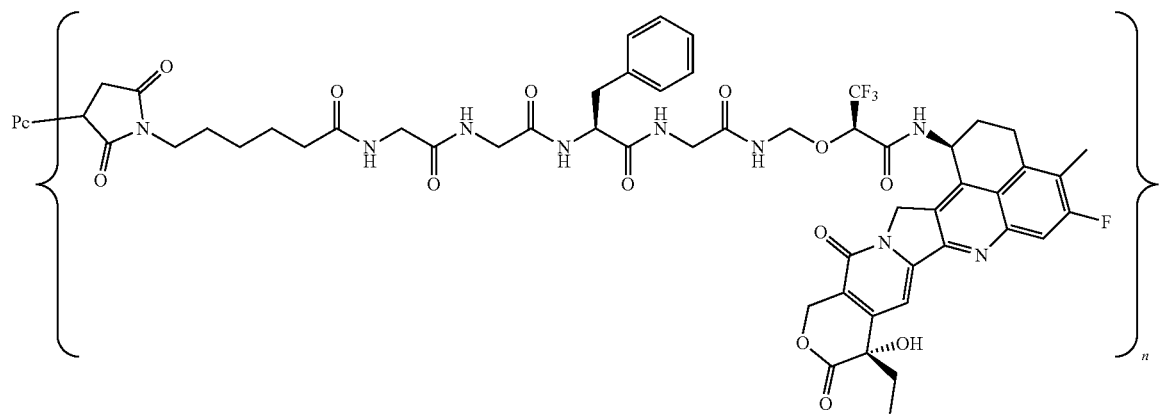

-continued
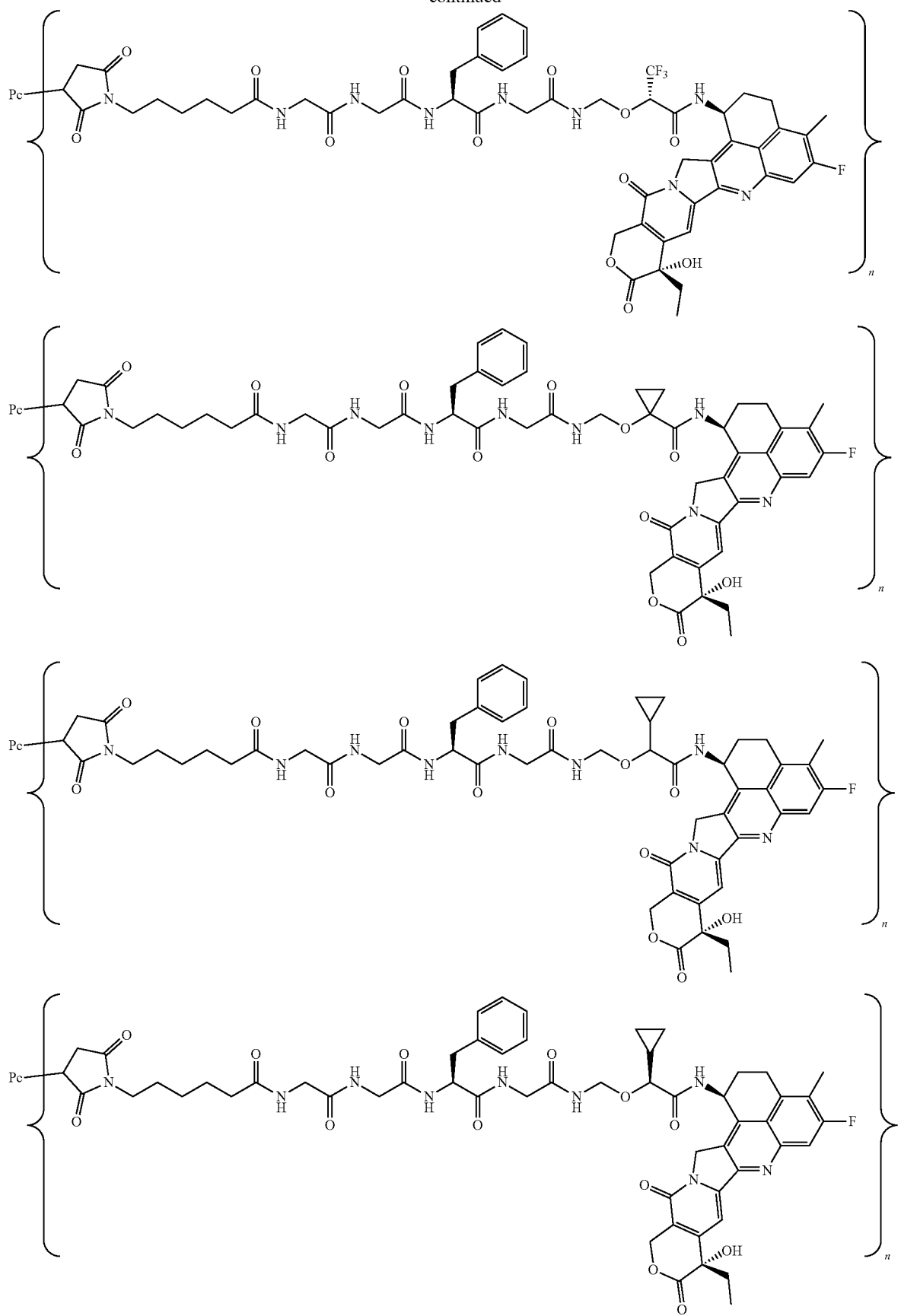

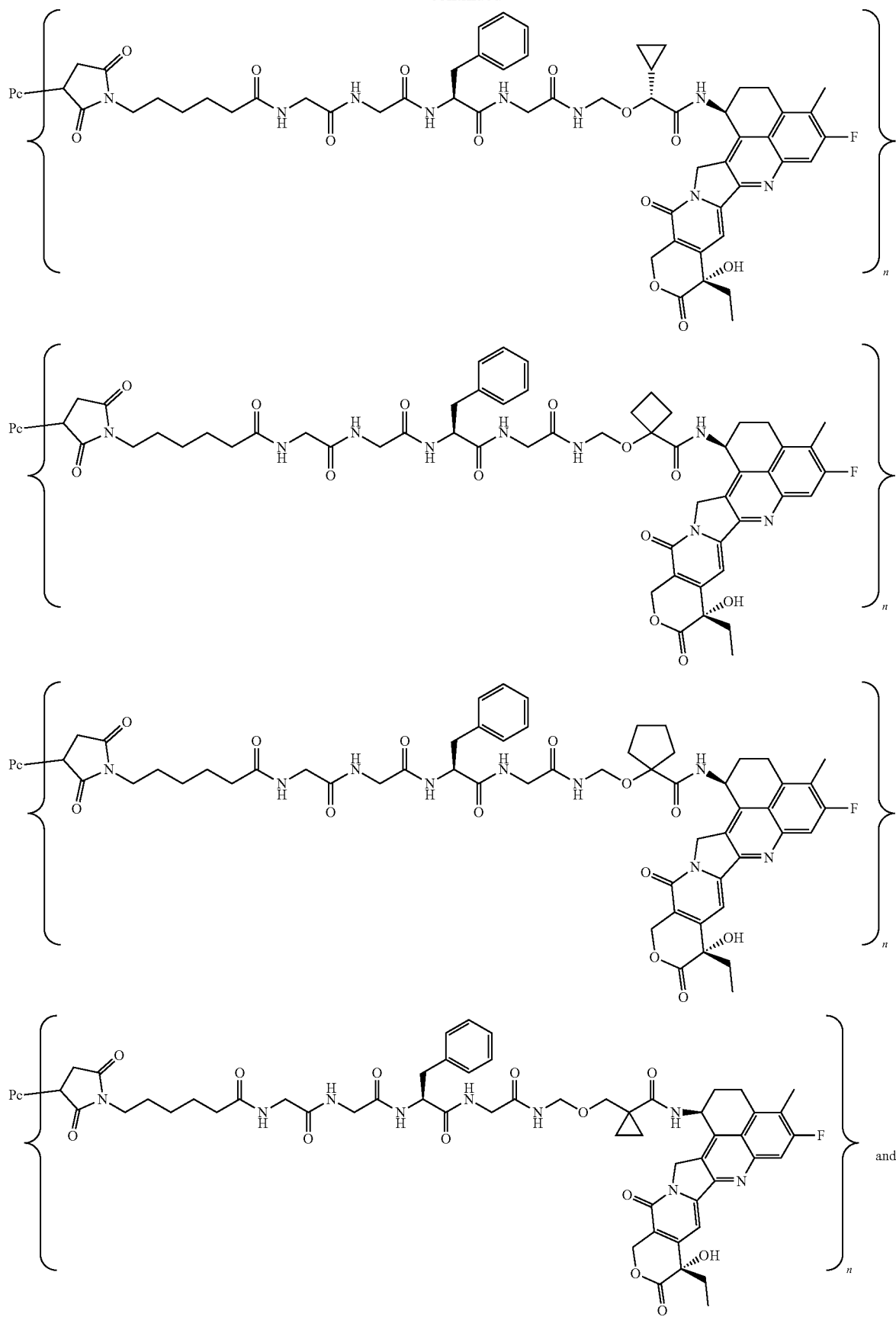

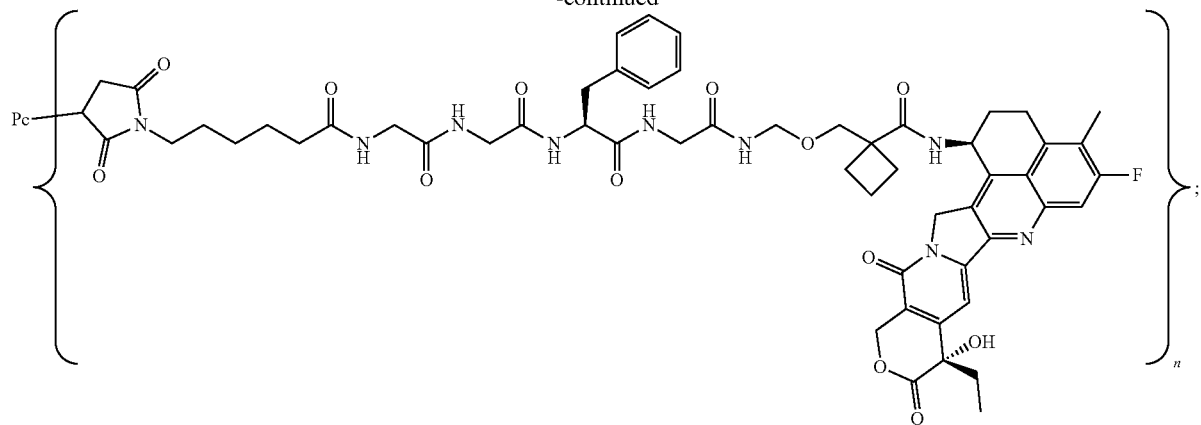
wherein Pc and n are as defined in formula (Pc-L-Y-Dr).
Typical ligand-drug conjugates of formula (Pc-L-Y-Dr) of the present disclosure include, but are not limited to the following ligand-drug conjugates:
| Example No. | Structure formula of ADC |
|---|---|
| ADC-1 | 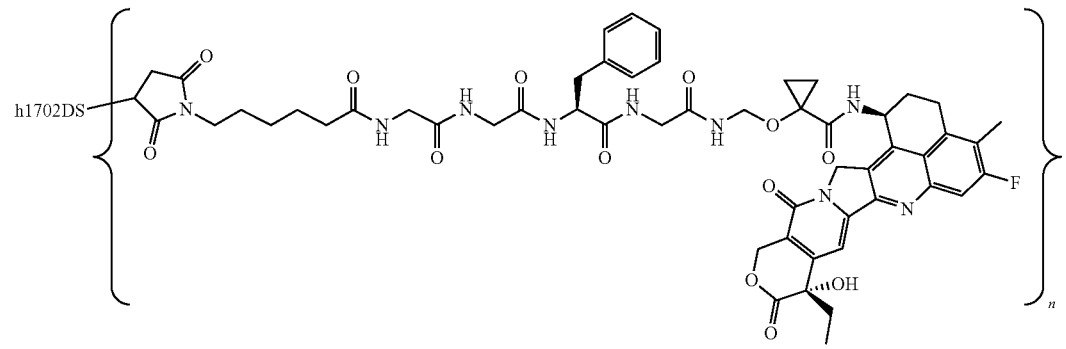<br>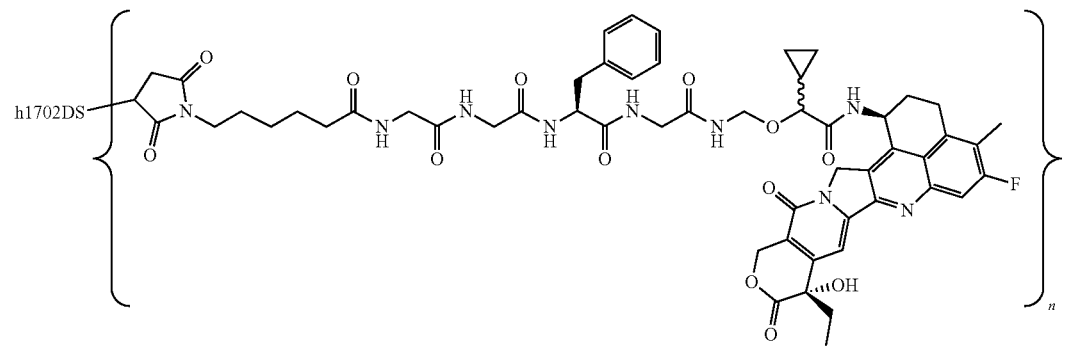 |

| Example No. | Structure formula of ADC |
|---|---|
| | 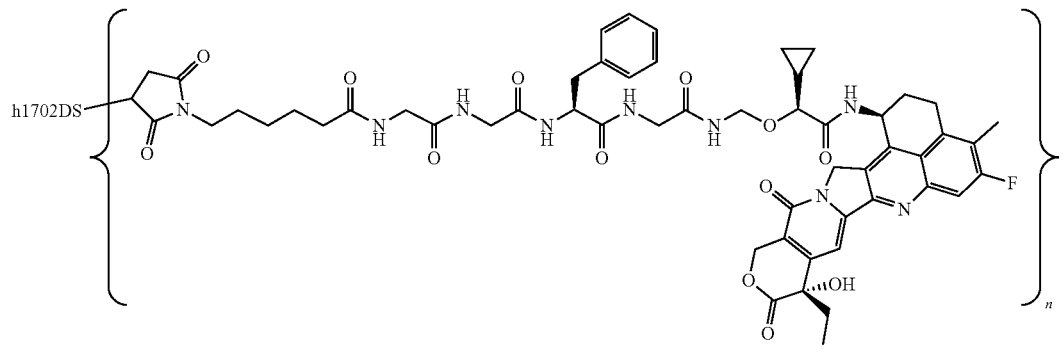 |
| ADC-2 | 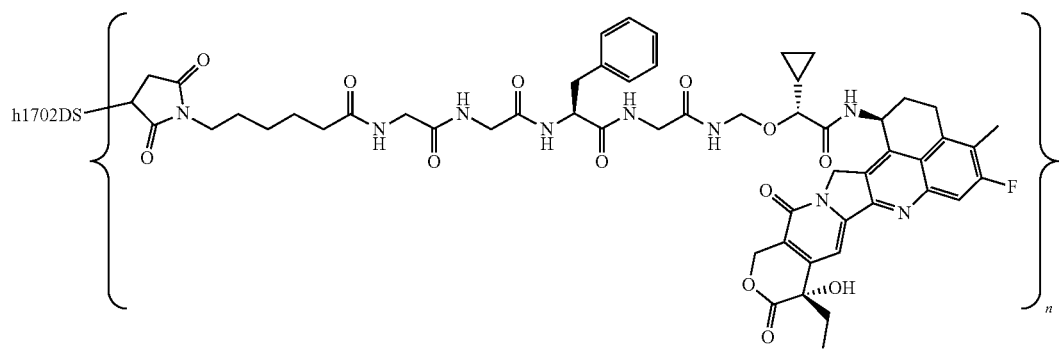 |
| ADC-3 | 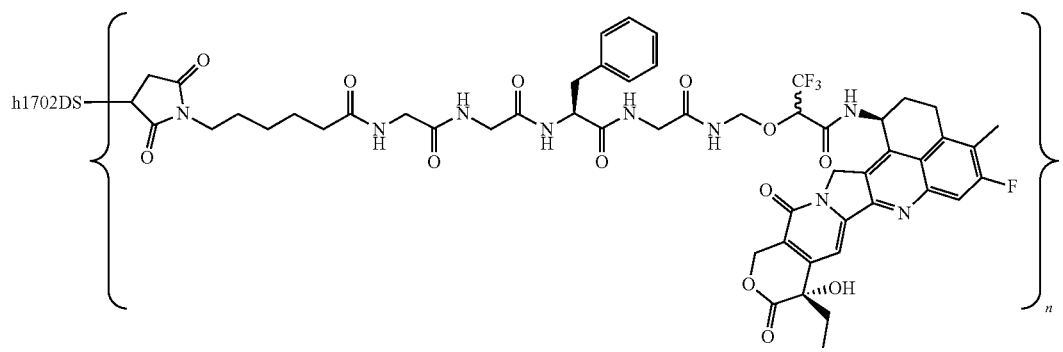 |
| | 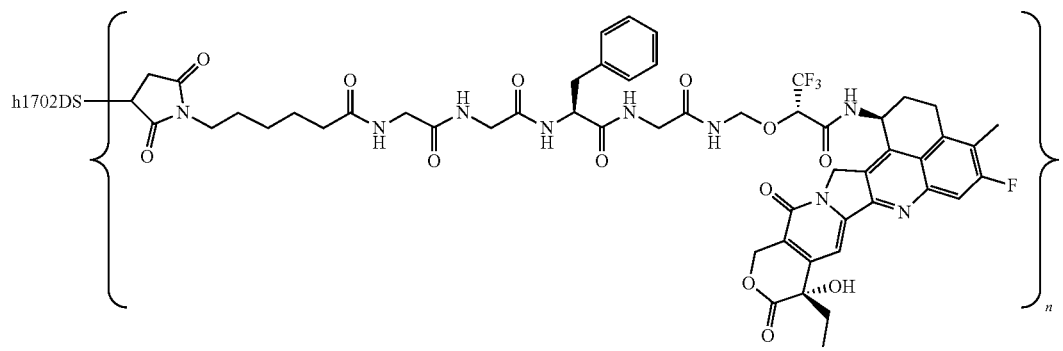 |

| Example No. | Structure formula of ADC |
|---|---|
| | 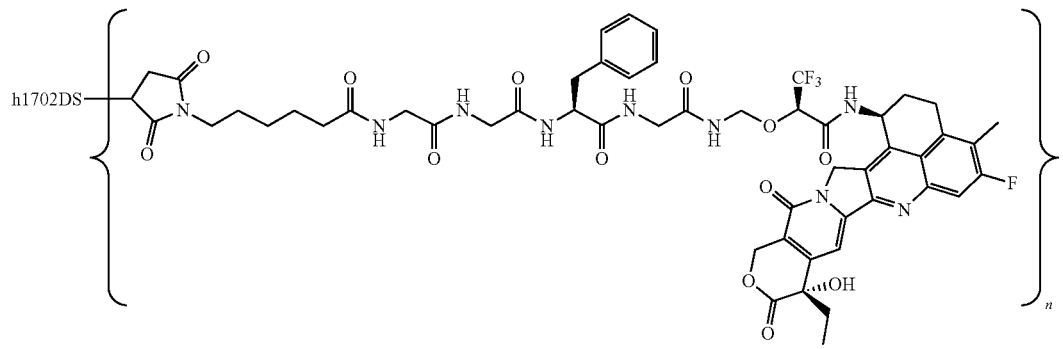 | or a pharmaceutically acceptable salt or solvate thereof, wherein, n can be a non-zero integer or decimal from 0 to 10, preferably n is an integer or decimal from 1 to 10; more preferably n is 2 to 8, which can be an integer or a decimal; and most preferably n is 3 to 8, which can be an integer or a decimal.

The present disclosure further provides a method for preparing the ligand-drug conjugate of formula (Pc-$L_a$-Y-Dr) or the pharmaceutically acceptable salt or solvate thereof, comprising the following step of:

Pc is coupled with the compound of formula ($L_a$-Y-Dr) after reduction to obtain the compound of formula (Pc-$L_a$-Y-Dr); the reducing agent is preferably TCEP;

wherein:

Pc is an anti-B7H3 antibody or an antigen-binding fragment thereof,

W, $L^2$, $L^3$, $R^1$, $R^2$, $R^5$~$R^7$, m and n are as defined in formula (Pc-$L_a$-Y-Dr).

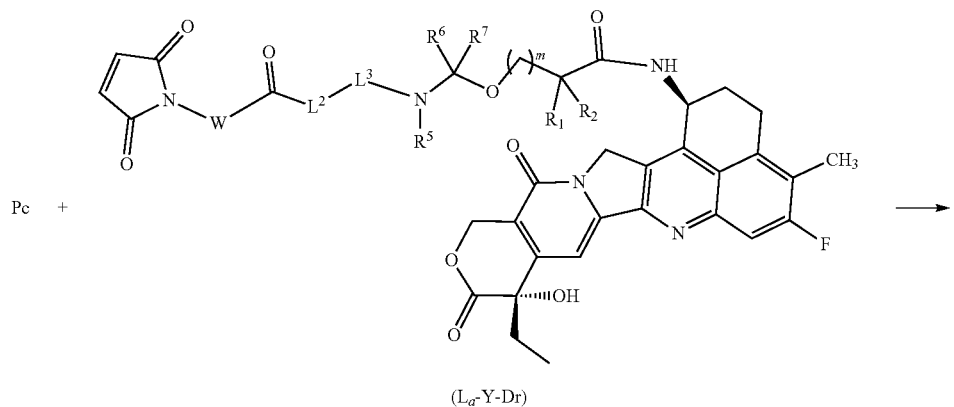

($L_a$-Y-Dr)

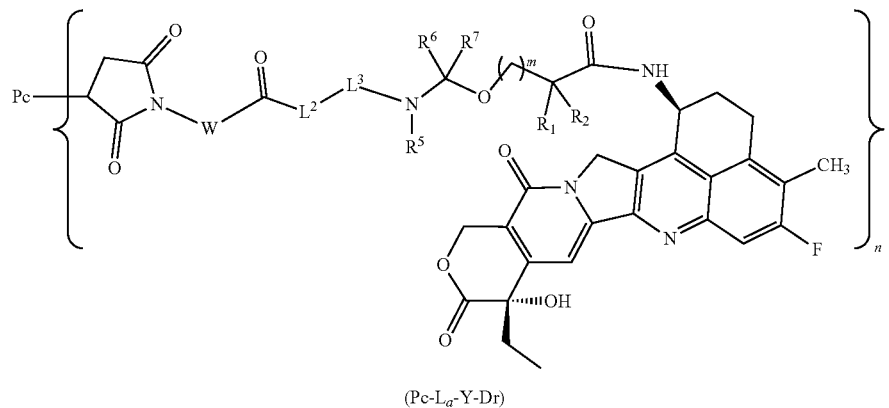

(Pc-$L_a$-Y-Dr)

Another embodiment provides another method, wherein the compound of formula L-Y-Dr is a compound of formula 4b-Y-Dr:

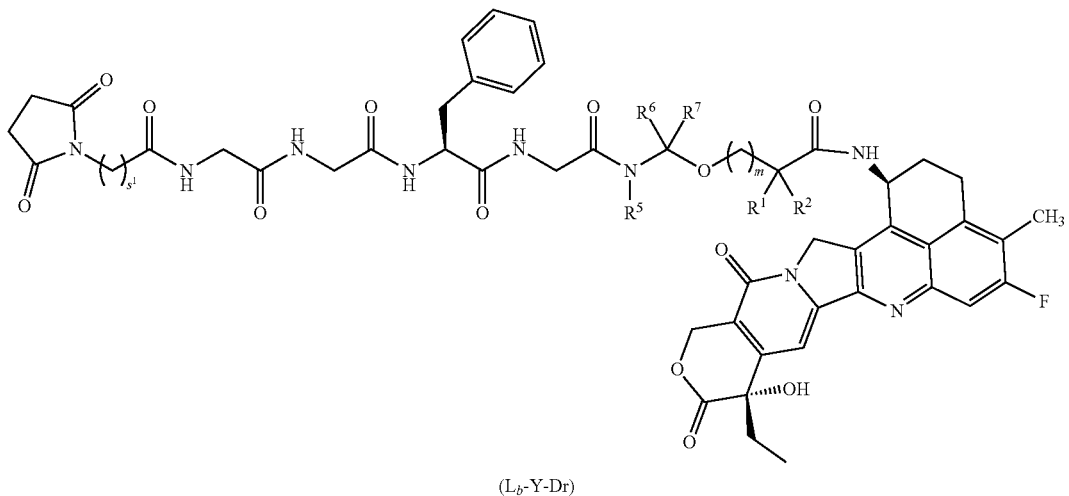

(L$_b$-Y-Dr)

or a tautomer, mesomer, racemate, enantiomer, diastereomer thereof, or mixture thereof, or a pharmaceutically acceptable salt thereof, wherein $R^1$, $R^2$, $R^5\sim R^7$, $s^1$ and m are as defined in formula Pc-L$_b$-Y-Dr.

In a preferred embodiment of the present disclosure, in method for preparing the ligand-drug conjugate of formula (Pc-L$_a$-Y-Dr) or (Pc-L$_b$-Y-Dr) or the pharmaceutically acceptable salt or solvate thereof, the compound of formula (L$_a$-Y-Dr) or the compound of formula (L$_b$-Y-Dr) is selected from the group consisting of:

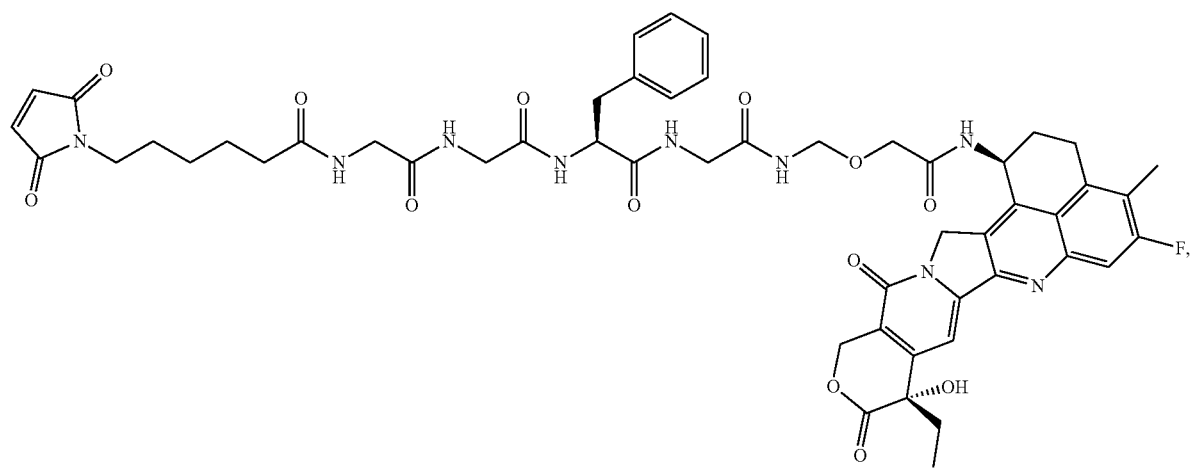

8

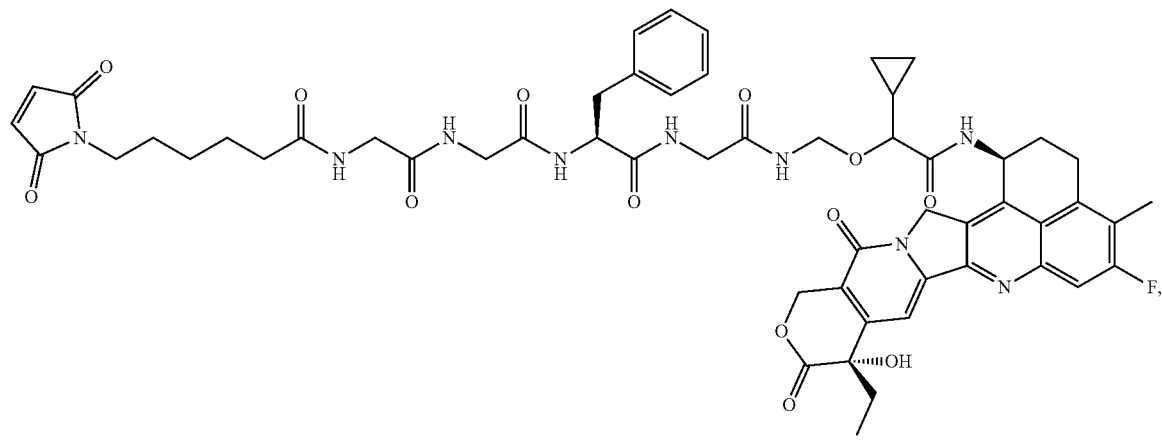
9
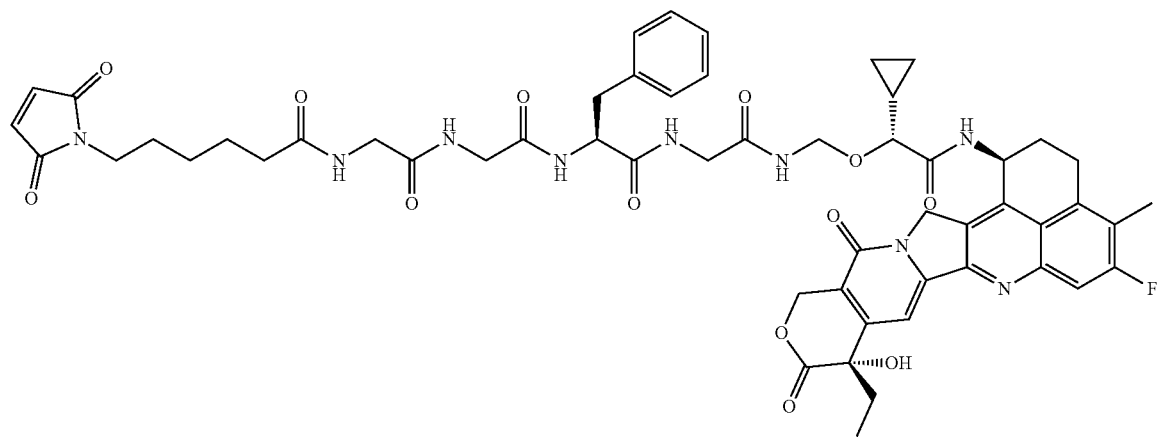
9-A
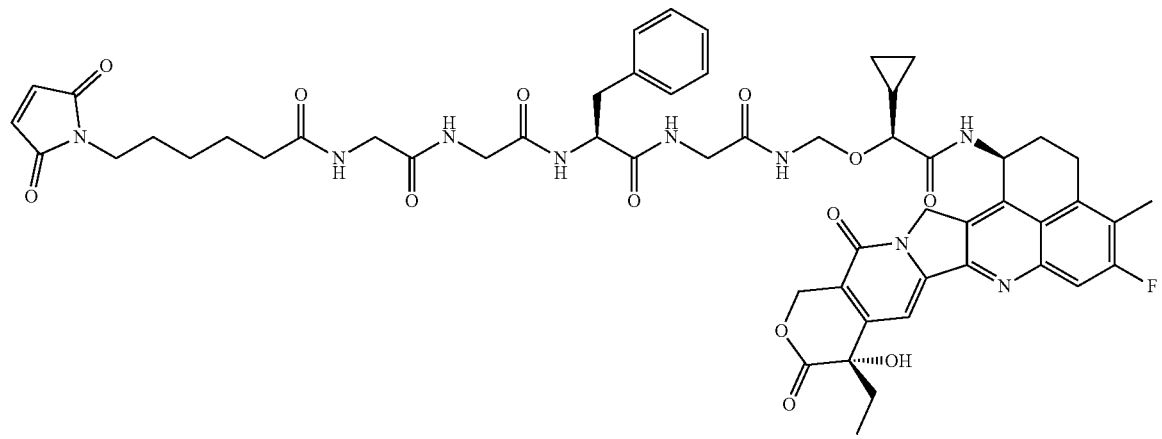
9-B

-continued
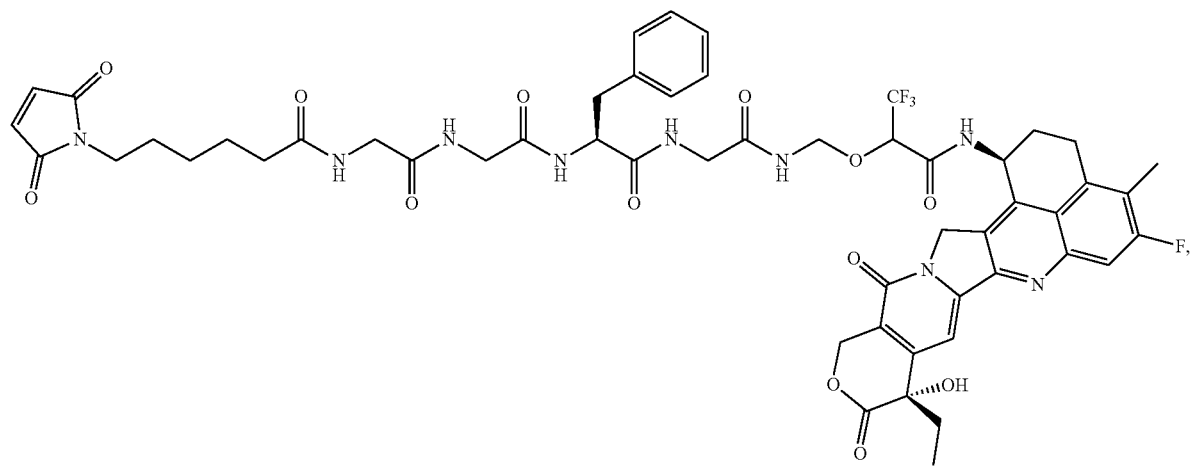
10
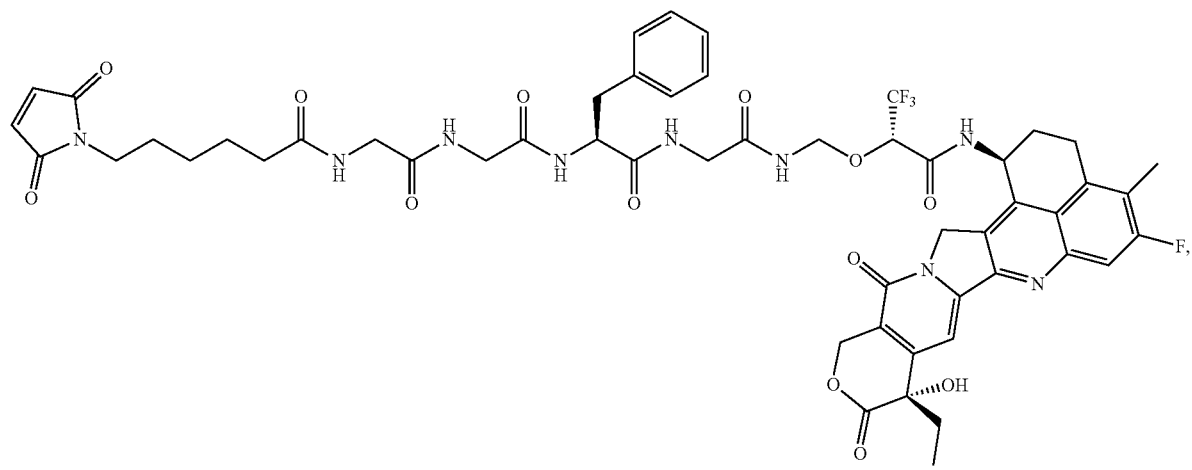
10-A
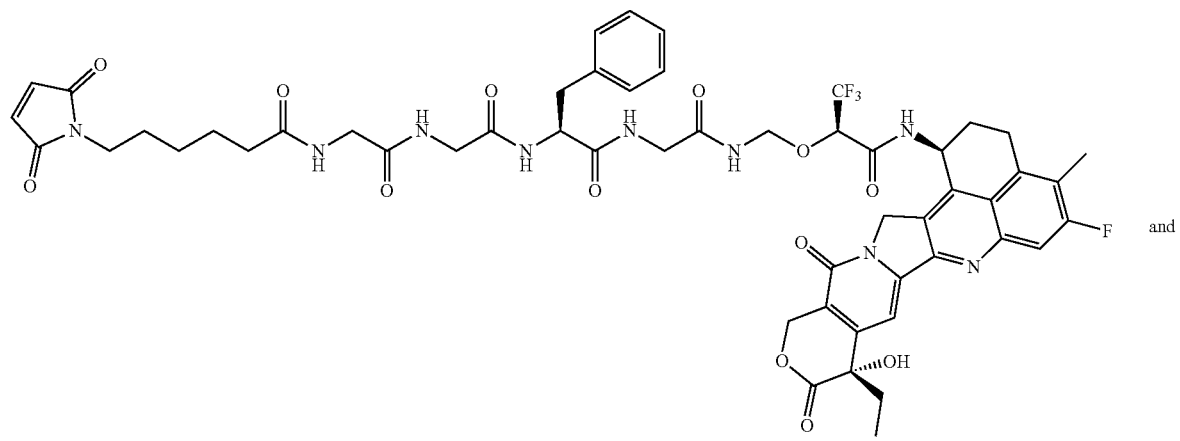
10-A
and

-continued

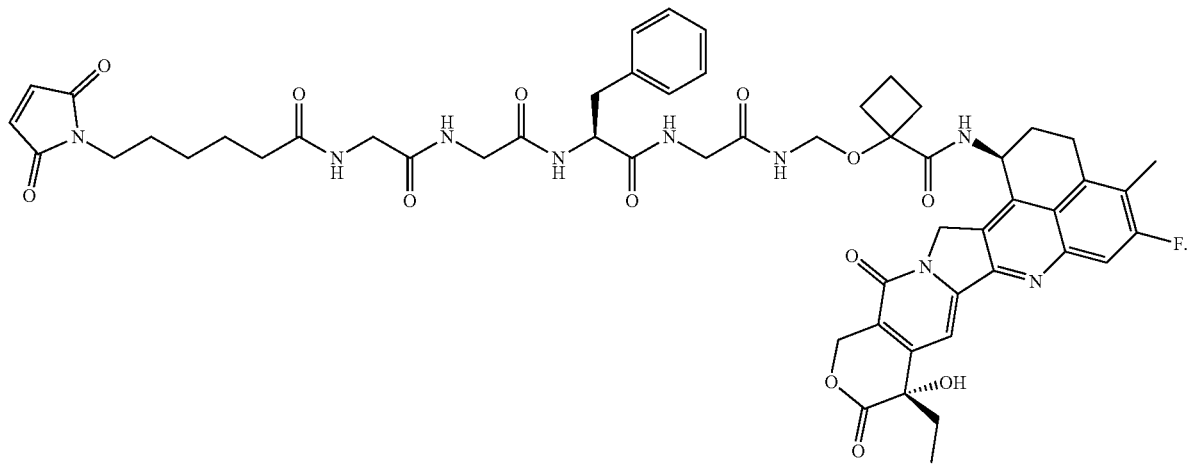

In another aspect, the present disclosure provides a pharmaceutical composition comprising the ligand-drug conjugate or the pharmaceutically acceptable salt or solvate thereof according to the present disclosure, and one or more pharmaceutically acceptable excipient(s), diluent(s) or carrier(s).

In another aspect, the present disclosure provides a use of the ligand-drug conjugate or the pharmaceutically acceptable salt or solvate thereof, or the pharmaceutical composition comprising the same according to the present disclosure in the preparation of medicaments for the treatment of B7H3-mediated diseases or disorders; the B7H3-mediated disease or disorder is a cancer with high expression of B7H3.

In another aspect, the present disclosure provides a use of the ligand-drug conjugate or the pharmaceutically acceptable salt or solvate thereof, or the pharmaceutical composition comprising the same according to the present disclosure in the preparation of medicaments for the treatment or prevention of a tumor, wherein the cancer is preferably selected from the group consisting of breast cancer, ovarian cancer, cervical cancer, lung cancer, uterine cancer, prostate cancer, kidney cancer, urethral cancer, bladder cancer, ovarian cancer, liver cancer, stomach cancer, endometrial cancer, salivary gland cancer, esophageal cancer, melanoma, glioma, neuroblastoma, sarcoma, pharyngeal cancer, lung cancer, colon cancer, rectal cancer, colorectal cancer, leukemia, bone cancer, skin cancer, thyroid cancer, pancreatic cancer and lymphoma.

In another aspect, the present disclosure further relates to a method for treating and/or preventing a tumor comprising administering to a patient in need thereof a therapeutically effective amount of the ligand-drug conjugate or the pharmaceutically acceptable salt or solvate thereof, or the pharmaceutical composition comprising the same according to the present disclosure, wherein the tumor is preferably a cancer related to high expression of B7H3.

In another aspect, the present disclosure further relates to a method for treating or preventing a cancer comprising administering to a patient in need thereof a therapeutically effective amount of the ligand-drug conjugate or the pharmaceutically acceptable salt or solvate thereof, or the pharmaceutical composition comprising the same according to the present disclosure, wherein the cancer is preferably selected from the group consisting of breast cancer, ovarian cancer, cervical cancer, lung cancer, uterine cancer, prostate cancer, kidney cancer, urethral cancer, bladder cancer, ovarian cancer, liver cancer, stomach cancer, endometrial cancer, salivary gland cancer, esophageal cancer, melanoma, glioma, neuroblastoma, sarcoma, pharyngeal cancer, lung cancer, colon cancer, rectal cancer, colorectal cancer, leukemia, bone cancer, skin cancer, thyroid cancer, pancreatic cancer and lymphoma.

The active compound can be formulated into a form suitable for administration by any appropriate route, and the active compound is preferably in the form of a unit dose, or in a form in which the patient can self-administer in a single dose. The form of the unit dose of the compound or composition of the present disclosure can be tablet, capsule, cachet, ampoule, powder, granule, lozenge, suppository, regenerating powder or liquid preparation.

The dosage of the compound or composition used in the therapeutic method of the present disclosure will generally vary according to the severity of the disease, the weight of the patient, and the relative efficacy of the compound. However, as a general guide, a suitable unit dose can be 0.1 to 1000 mg.

In addition to the active compound, the pharmaceutical composition of the present disclosure can also comprise one or more auxiliaries including filler (diluent), binder, wetting agent, disintegrant, excipient and the like. Depending on the administration mode, the composition can comprise 0.1 to 99% by weight of the active compound.

DESCRIPTION OF THE DRAWINGS

FIG. 2A is the test results of the inhibitory effect of various ADCs on the proliferation of A498 cells; FIG. 2B is the test results of the inhibitory effect of various ADCs on the proliferation of Calu-6 cells; FIG. 2C is the test results of the inhibitory effect of various ADCs on the proliferation of U87 cells; FIG. 2D is the test results of the inhibitory effect of various ADCs on the proliferation of A375 cells; FIG. 2E is the test results of the inhibitory effect of various ADCs on the proliferation of Detroit562 cells; and FIG. 2F is the test results of the inhibitory effect of various ADCs on the proliferation of CHOK1 cells.

DETAILED DESCRIPTION OF THE INVENTION

I. Terms

Figure 1:
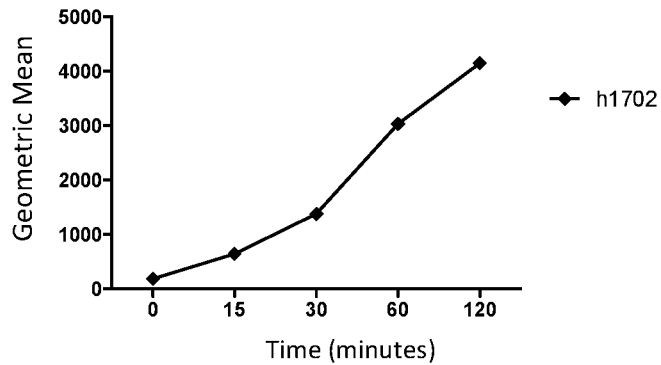
FIG. 1: The endocytosis effect of B7H3 antibody on U87MG cells.
Figure 2A:
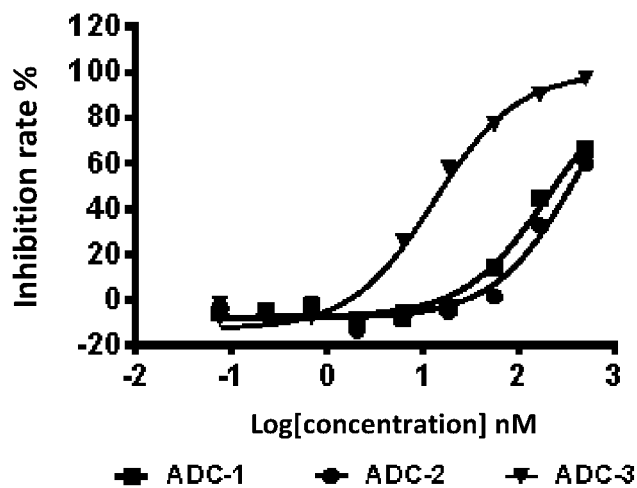
FIG. 2A-2F: The results of the inhibitory effect of the present ADC on the proliferation of various tumor cells.
Figure 2B:
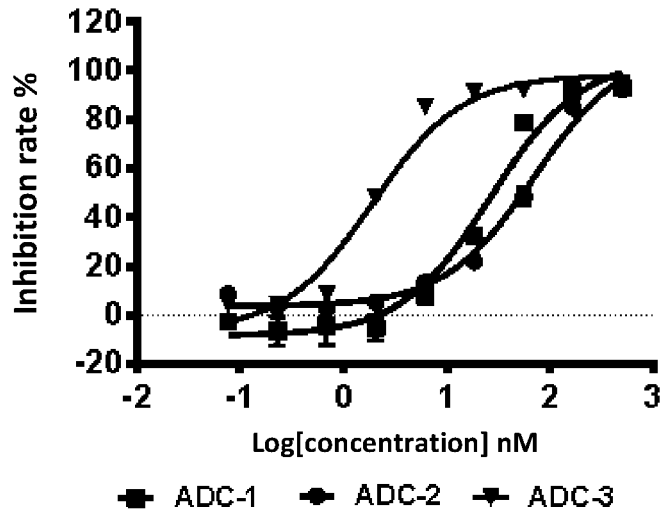
Figure 2C:
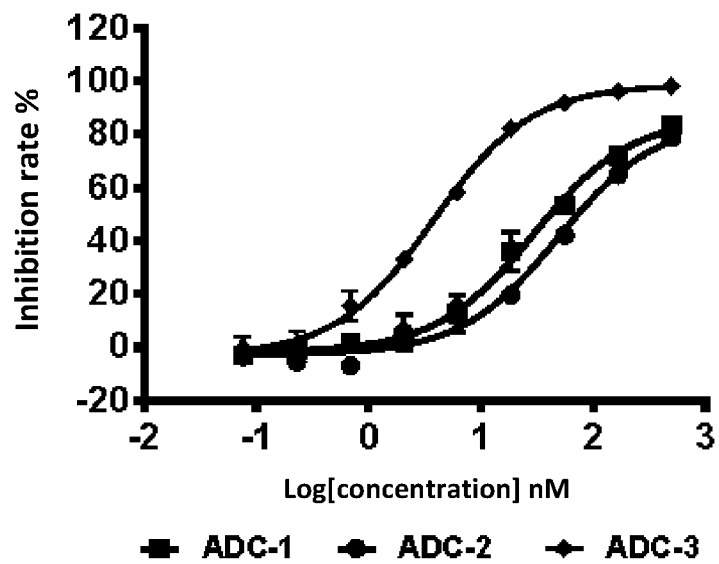
Figure 2D:
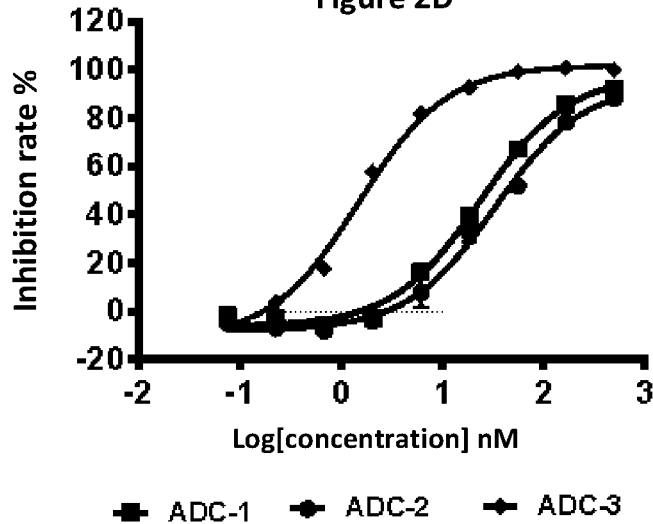
Figure 2E:
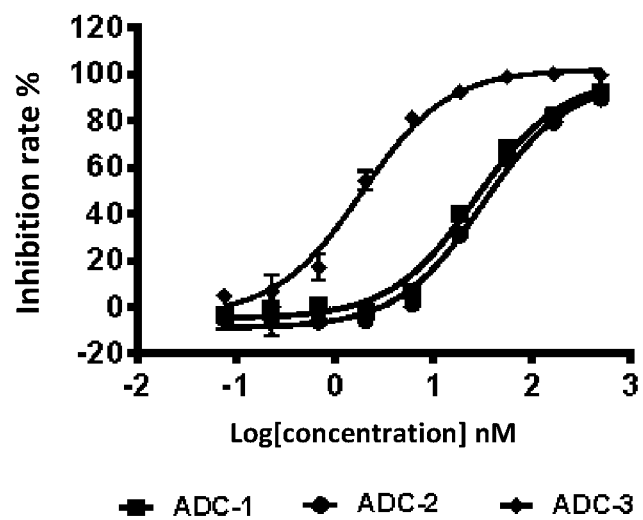
Figure 2F:
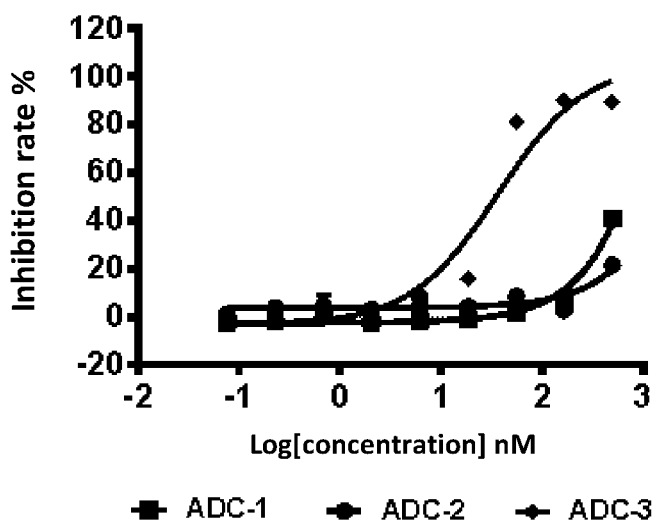

Unless otherwise specified, all technical and scientific terms used herein are consistent with the common understanding of those of ordinary skill in the art to which the present disclosure belongs. Although any methods and materials similar or equivalent to those described herein can be used in the practice or testing of the present disclosure, preferred methods and materials are described herein. When describing and protecting the present disclosure, the following terms are used in accordance with the following definitions.

When a trade name is used in the present disclosure, the applicant is intended to include the preparations, the generic drug and the active ingredients of the product under the trade name.

Unless otherwise stated, the terms used in the specification and claims have the meanings described below.

The term "drug" refers to a cytotoxic drug, which is represented by Dr, being a chemical molecule that can strongly disrupt the normal growth of tumor cells. In principle, all cytotoxic drugs can kill tumor cells at a sufficiently high concentration. However, it can cause the apoptosis of normal cell and serious side effects while killing tumor cells due to the lack of specificity.

This term includes toxins, such as small molecule toxins or enzymatically active toxins of bacterial, fungal, plant or animal origin, radioisotopes (for example, radioisotopes of $At^{211}$, $I^{131}$, $I^{125}$, $Y^{90}$, $Re^{186}$, $Re^{188}$, $Sm^{153}$, $Bi^{212}$, $P^{32}$ and Lu), toxic drugs, chemotherapy drugs, antibiotics and nucleolytic enzymes, and preferably toxic drugs.

The term "linker unit (or linking fragment)" refers to a chemical structural fragment or bond, which is linked to a ligand at one end and linked to a drug at another end, or linked to a drug via another linkers. The preferred embodiments of the present disclosure are represented by L and $L^1$ to $L^4$, wherein the $L^1$ end is linked to the ligand, and the $L^4$ end is linked to the drug (Dr) through the structural unit Y.

The linker, including extension unit, spacer unit, and amino acid unit, can be synthesized by methods known in the art, such as those described in US 2005-0238649A1. The linker can be a "cleavable linker" that facilitates the release of the drug in cell. For example, an acid labile linker (for example, hydrazone), a protease-sensitive (for example, peptidase-sensitive) linker, a light-labile linker, a dimethyl linker or a disulfide-containing linker (Chari et al, Cancer Research 52: 127-131 (1992); U.S. Pat. No. 5,208,020) can be used.

The term "ligand-drug conjugate" means that a ligand is linked to a biologically active drug through a stable linking unit. In the present disclosure, the "ligand-drug conjugate" is preferably an antibody-drug conjugate (ADC), which means that a monoclonal antibody or antibody fragment is linked to a biologically active toxic drug through a stable linking unit.

The three-letter codes and one-letter codes for amino acids used in the present disclosure are as described in J. biol. chem, 243, p3558 (1968).

The term "antibody" refers to immunoglobulin, a four polypeptide chain structure connected together by interchain disulfide bond between two identical heavy chains and two identical light chains. Different immunoglobulin heavy chain constant regions exhibit different amino acid constituents and sequences, thereby presenting different antigenicity. Accordingly, immunoglobulins can be divided into five types, or called immunoglobulin isotypes, namely IgM, IgD, IgG, IgA and IgE, with corresponding heavy chain μ, δ, γ, α and ε, respectively. According to the amino acid constituents of hinge region and the number and location of heavy chain disulfide bonds, the same type of Ig can further be divided into different sub-types, for example, IgG can be divided into IgG1, IgG2, IgG3 and IgG4. Light chain can be divided into κ or λ chain based on different constant region. Each five types of Ig can have a κ or λ chain.

The sequence of about 110 amino acids adjacent to the N-terminus of the antibody heavy chains or light chains is highly variable, thus called variable region (Fv region). The rest of amino acid sequence adjacent to the C-terminus is relatively stable, thus called constant region. The variable region includes three hypervariable regions (HVR) and four relatively conservative framework regions (FR). The three hypervariable regions, which determine the specificity of the antibody, are also known as the complementarity determining regions (CDR). Each light chain variable region (LCVR) or each heavy chain variable region (HCVR) consists of three CDR regions and four FR regions, with sequential order from the amino terminus to carboxyl terminus in the following order: FR1, CDR1, FR2, CDR2, FR3, CDR3, FR4. The three CDR regions of the light chain refer to LCDR1, LCDR2, and LCDR3; and the three CDR regions of the heavy chain refer to HCDR1, HCDR2, and HCDR3. The number and location of the CDR amino acid residues in the LCVR and HCVR regions of the antibody or antigen binding fragment of the present disclosure comply with known Kabat numbering criteria (LCDR1-3, HCDR2-3), or comply with Kabat and Chothia numbering criteria (HCDR1).

The term "fully humanized antibody" is also known as "fully humanized monoclonal antibody", wherein the variable region and constant region of the antibody are both of human origin, eliminating immunogenicity and side effects. The development of monoclonal antibody has gone through four stages, namely: murine monoclonal antibody, chimeric monoclonal antibody, humanized monoclonal antibody and fully humanized monoclonal antibody. The related technologies of fully humanized antibody preparation mainly include human hybridoma technology, EBV transformed B lymphocyte technology, phage display technology, transgenic mouse antibody preparation technology, single B cell antibody preparation technology and the like. The "fully humanized antibody" of the present disclosure is obtained by phage display technology. The phage display technology includes constructing natural single-stranded phage human antibody library by isolating B cells from human PBMC, spleen, lymph node tissue, or screening antibodies by immunizing transgenic mice expressing human antibody light and heavy chain.

The term "antigen binding fragment" refers to one or more fragments of an antibody retaining the specific binding ability to the antigen. It has been shown that fragments of full-length antibody can be used to achieve the function of binding with an antigen. The examples of binding fragments in the term "antigen binding fragment" include (i) Fab fragment, a monovalent fragment composed of VL, VH, CL and CH1 domain; (ii) F(ab')$_2$ fragment, a bivalent fragment comprising two Fab fragments connected by a disulphide bond in the hinge region; (iii) Fd fragment, consisting of VH and CH1 domains; (iv) Fv fragment, consisting of VH and VL domains of one-arm antibody; (v) single domain or dAb fragment (Ward et al. (1989) Nature 341:544-546) composed of VH domain; and (vi) an isolated complementary determining region (CDR) or (vii) a combination of two or more isolated CDRs optionally connected by a synthetic linker. In addition, although the VL domain and VH domain of the Fv fragment are encoded by two separate genes, they can be connected by a synthetic linker by using recombinant methods, thereby generating a single protein chain in which a monovalent molecular formed by pairing the VL and VH domain (referred to as single chain Fv (scFv); see, e.g., Bird et al. (1988) Science: 242:423-426, and Huston et al. (1988) Proc. Natl. Acad. Sci USA 85:5879-5883). This single chain antibody is also intended to be included in the term "antigen binding fragment" of the antibody. Such antibody fragments are obtained using conventional techniques known by those skilled in the art, and screened for functional fragments by using the same method as that for an intact antibody. Antigen binding sites can be produced by recombinant DNA technology or by enzymatic or chemical disruption of an intact immunoglobulin. Antibodies can be antibodies of different isotypes, e.g., IgG (e.g., IgG1, IgG2, IgG3 or IgG4 subtype), IgA1, IgA2, IgD, IgE or IgM antibody.

Fab is an antibody fragment obtained by treating an IgG antibody molecule with a papain (which cleaves the amino acid residue at position 224 of the H chain). The Fab fragment has a molecular weight of about 50,000 and has antigen binding activity, in which about a half of the N-terminal side of H chain and the entire L chain are bound together through a disulfide bond.

F(ab')2 is an antibody fragment obtained by digesting the downstream part of the two disulfide bonds in the hinge region of IgG with pepsin, which has a molecular weight of about 100,000 and has antigen binding activity and comprises two Fab regions which are bound at the hinge position.

Fab' is an antibody fragment obtained by cleaving the disulfide bond at the hinge region of the above F(ab')2, which has a molecular weight of about 50,000 and has antigen binding activity.

Moreover, the Fab' can be produced by inserting DNA encoding Fab' fragment of the antibody into a prokaryotic expression vector or eukaryotic expression vector which is then introduced into a prokaryote or eukaryote to express the Fab'.

The term "single chain antibody", "single chain Fv" or "scFv" refers to a molecule comprising an antibody heavy chain variable domain (or region; VH) and an antibody light chain variable domain (or region; VL) connected by a linker. Such scFv molecules can have the general structure of NH$_2$-VL-linker-VH—COOH or NH$_2$-VH-linker-VL-COOH. A suitable linker in the prior art consists of repeated GGGGS amino acid sequence or variant thereof, for example, using a variant with 1-4 repeats (Holliger et al. (1993), Proc. Natl. Acad. Sci. USA 90:6444-6448). Other linkers that can be used in the present disclosure are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

The term "CDR" refers to one of the six hypervariable regions within the variable domain of an antibody that primarily contributes to antigen binding. One of the most commonly used definitions for the six CDRs is provided by Kabat E. A. et al. (1991) Sequences of proteins of immunological interest. NIH Publication 91-3242. As used herein, the Kabat definition of CDR only applies to CDR1, CDR2 and CDR3 of the light chain variable domain (CDR L1, CDR L2, CDR L3 or L1, L2, L3), as well as CDR2 and CDR3 of heavy chain variable domain (CDR H2, CDR H3 or H2, H3).

The term "antibody framework" refers to a portion of the variable domain VL or VH, which serves as a scaffold for the antigen binding loop (CDR) of the variable domain. Essentially, it is a variable domain without CDR.

The term "epitope" or "antigenic determinant" refers to a site of an antigen to which an immunoglobulin or antibody specifically binds. Epitopes typically include at least 3, 4, 5, 6, 7, 8, 9, 10, 11, 12, 13, 14 or 15 contiguous or non-contiguous amino acids in an unique spatial conformation. See, for example, Epitope Mapping Protocols in Methods in Molecular Biology, Vol. 66, G. E. Morris, Ed. (1996).

The terms "specific binding", "selective binding", "selectively bind" and "specifically bind" refer to the binding of an antibody to an epitope on a predetermined antigen. Typically, the antibody binds with an affinity (KD) of less than about $10^{-7}$ M, such as less than about $10^{-8}$ M, $10^{-9}$ M or $10^{-10}$ M or less.

The term "nucleic acid molecule" refers to a DNA molecule and a RNA molecule. The nucleic acid molecule can be single stranded or double stranded, but is preferably a double stranded DNA. A nucleic acid is "effectively linked" when it is placed into functional relationship with another nucleic acid sequence. For example, if a promoter or enhancer affects transcription of a coding sequence, the promoter or enhancer is effectively linked to the coding sequence.

The term "vector" refers to a nucleic acid molecule capable of transporting another nucleic acid to which it has been linked to it. In one embodiment, the vector is a "plasmid" which refers to a circular double stranded DNA loop into which additional DNA segment can be ligated. In another embodiment, the vector is a viral vector, wherein an additional DNA segment can be ligated into viral genome. The vectors disclosed herein are capable of self-replicating in a host cell into which they have been introduced (for example, a bacterial vector having a bacterial replication origin and an episomal mammalian vector) or can be integrated into the genome of a host cell upon introduction into host cell, thereby is replicated along with the host genome (for example, a non-episomal mammalian vector).

Methods for producing and purifying antibodies and antigen binding fragments are well known in the art, such as Cold Spring Harbor Antibody Technical Guide, Chapters 5-8 and 15. The antigen binding fragment can also be prepared by conventional methods. The antibodies or antigen binding fragments of the invention are genetically engineered to add one or more human FR regions in non-human CDR regions. The human FR germline sequence(s) can be obtained by aligning IMGT human antibody variable germlines gene databases and MOE software from the ImMunoGeneTics (IMGT) website at http://imgt.cines.fr or from the Journal of Immunoglobulins 20011SBN012441351.

The term "host cell" refers to a cell into which an expression vector has been introduced. Host cells can include bacterial, microbial, plant or animal cells. Bacteria susceptible to be transformed include members of the Enterobacteriaceae, such as strains of *Escherichia coli* or *Salmonella*; Bacillaceae such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

The engineered antibody or antigen binding fragment of the present disclosure can be prepared and purified by conventional methods. For example, cDNA sequence(s) encoding a heavy chain and a light chain can be cloned and recombined into a GS expression vector. The recombinant immunoglobulin expression vector can be stably transfected in CHO cells. As a more recommended existing technology, mammalian expression systems can result in glycosylation of antibodies, particularly at the highly conserved N-terminal site of the Fc region. Positive clones are amplified in serum-free medium in a bioreactor to produce antibodies. The culture medium containing the secreted antibody can be purified by conventional technique. For example, purification is carried out using an A or G Sepharose FF column that contains an adjusted buffer. The non-specifically bound components are removed by eluting. The bound antibody is eluted by a pH gradient method, and the antibody fragments are detected by SDS-PAGE and collected. The antibody can be filtered and concentrated by a conventional method. Soluble aggregate and multimers can also be removed by conventional methods such as size exclusion or ion exchange. The resulting product needs to be frozen immediately, such as at −70° C., or lyophilization.

The term "peptide" refers to a compound fragment between amino acid and protein, consisting of two or more amino acid molecules connected to each other through peptide bonds. Peptides are structural and functional fragments of proteins. Hormones, enzymes and the like are essentially peptides.

The term "saccharide" refers to a biological macromolecule composed of three elements of C, H, and O, which can be divided into monosaccharides, disaccharides and polysaccharides.

The term "fluorescent probe" refers to a kind of fluorescent molecules with characteristic fluorescence in the ultraviolet-visible-near infrared region. The fluorescence property (excitation and emission wavelengths, intensity, lifetime and polarization, etc.) of fluorescent probecan sensitively vary according to the property of the environment, such as polarity, refractive index, viscosity, etc. Non-covalently interaction between fluorescent probe and nucleic acid (DNA or RNA), protein or other macromolecular structure enables the change of one or more fluorescent properties, which can be used to study the property and behavior of macromolecular substance.

The term "toxic drug" refers to a substance that inhibits or stops the function of cells and/or causes cell death or destruction. Toxic drugs include toxins and other compounds that can be used in tumor treatment.

The term "alkyl" refers to a saturated aliphatic hydrocarbon group, which is a straight or branched chain group comprising 1 to 20 carbon atoms, preferably an alkyl having 1 to 12 carbon atoms, more preferably an alkyl having 1 to 10 carbon atoms, and most preferably an alkyl having 1 to 6 carbon atoms (having 1, 2, 3, 4, 5 or 6 carbon atoms). Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio and oxo.

The term "heteroalkyl" refers to an alkyl containing one or more heteroatom(s) selected from the group consisting of N, O and S, wherein the alkyl is as defined above.

The term "alkylene" refers to a saturated linear or branched aliphatic hydrocarbon group having two residues derived from the removal of two hydrogen atoms from the same carbon atom or two different carbon atoms of the parent alkane. The alkylene is a linear or branched group having 1 to 20 carbon atoms, preferably 1 to 12 carbon atoms, and more preferably 1 to 6 carbon atoms (having 1, 2, 3, 4, 5 or 6 carbon atoms). Non-limiting examples of alkylene include, but are not limited to, methylene (—CH$_2$—), 1,1-ethylene (—CH(CH$_3$)—), 1,2-ethylene (—CH$_2$CH$_2$)—, 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), 1,5-pentylene (—CH$_2$CH$_2$CH$_2$CH$_2$CH$_2$—), and the like. The alkylene can be substituted or unsubstituted. When substituted, the substituent group(s) can be substituted at any available connection point. The substituent group(s) is preferably one or more groups independently optionally selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heteroalkoxy, cycloalkylthio, heterocyclylthio and oxo.

The term "alkoxy" refers to an —O-(alkyl) or an —O-(unsubstituted cycloalkyl) group, wherein the alkyl and cycloalkyl are as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocloalkoxy, cycloalkylthio and heterocyclylthio.

The term "cycloalkyl" refers to a saturated or partially unsaturated monocyclic or polycyclic hydrocarbon substituent group having 3 to 20 carbon atoms, preferably 3 to 12 carbon atoms, more preferably 3 to 10 carbon atoms, and most preferably 3 to 8 carbon atoms (having 3, 4, 5, 6, 7 or 8 carbon atoms). Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "heterocyclyl" refers to a 3 to 20 membered saturated or partially unsaturated monocyclic or polycyclic hydrocarbon group, wherein one or more ring atoms are heteroatoms selected from the group consisting of N, O and $S(O)_m$ (wherein m is an integer of 0, 1 or 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms (1, 2, 3 or 4 heteroatoms); and more preferably, 3 to 10 ring atoms (having 3, 4, 5, 6, 7, 8, 9 or 10 ring atoms). Non-limiting examples of monocyclic heterocyclyl include pyrrolidinyl, piperidinyl, piperazinyl, morpholinyl, thiomorpholinyl, homopiperazinyl and the like. Polycyclic heterocyclyl includes a heterocyclyl having a spiro ring, fused ring or bridged ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O and $S(O)_m$ (wherein m is an integer of 0 to 2), with the remaining ring atoms being carbon atoms, where the rings can contain one or more double bonds, but none of the rings has a completely conjugated π-electron system. The spiro heterocyclyl is preferably a 6 to 14 membered spiro heterocyclyl, and more preferably a 7 to 10 membered spiro heterocyclyl. According to the number of the spiro atoms shared between the rings, the spiro heterocyclyl can be divided into a mono-spiro heterocyclyl, di-spiro heterocyclyl, or poly-spiro heterocyclyl, and the spiro heterocyclyl is preferably a mono-spiro heterocyclyl or di-spiro heterocyclyl, and more preferably a 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

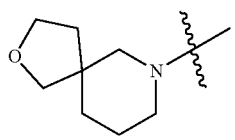

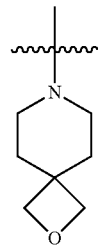

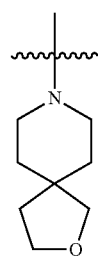

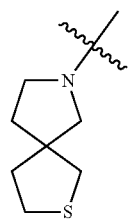

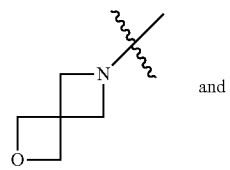 and

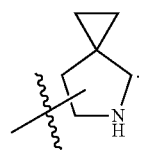

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and $S(O)_m$ (wherein m is an integer of 0, 1 or 2), with the remaining ring atoms being carbon atoms. The fused heterocyclyl is preferably a 6 to 14 membered fused heterocyclyl, and more preferably a 7 to 10 membered (7, 8, 9 or 10 membered) fused heterocyclyl. According to the number of membered rings, the fused heterocyclyl can be divided into a bicyclic, tricyclic, tetracyclic or polycyclic fused heterocyclyl, and the fused heterocyclyl is preferably a bicyclic or tricyclic fused heterocyclyl, and more preferably a 5-membered/5-membered or 5-membered/6-membered bicyclic fused heterocyclyl. Non-limiting examples of fused heterocyclyl include:

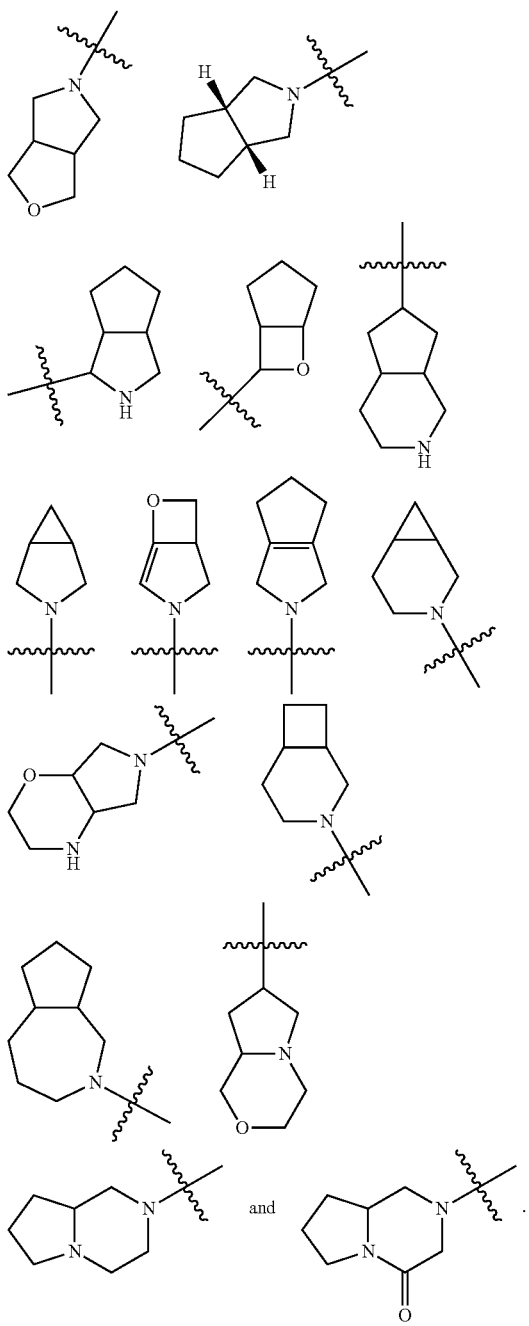

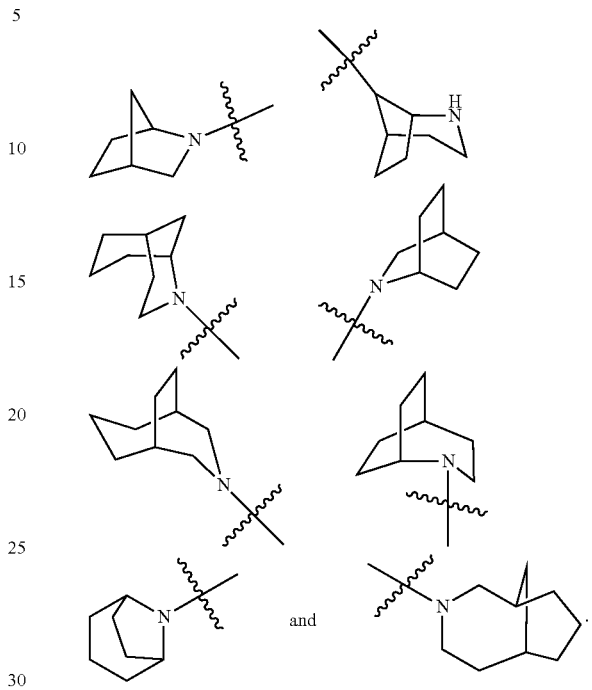

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and S(O)$_m$ (wherein m is an integer of 0, 1 or 2), with the remaining ring atoms being carbon atoms. The bridged heterocyclyl is preferably a 6 to 14 membered bridged heterocyclyl, and more preferably a 7 to 10 membered (7, 8, 9 or 10 membered) bridged heterocyclyl. According to the number of membered rings, the bridged heterocyclyl can be divided into a bicyclic, tricyclic, tetracyclic or polycyclic bridged heterocyclyl, and the bridged heterocyclyl is preferably a bicyclic, tricyclic or tetracyclic bridged heterocyclyl, and more preferably a bicyclic or tricyclic bridged heterocyclyl. Non-limiting examples of bridged heterocyclyl include:

The heterocyclyl ring can be fused to the ring of aryl, heteroaryl or cycloalkyl, wherein the ring bound to the parent structure is heterocyclyl. Non-limiting examples thereof include:

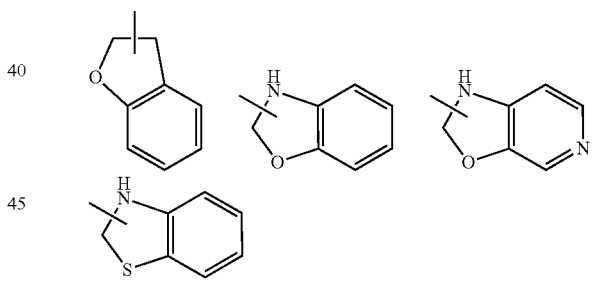

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio and oxo.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably a 6 to 10 membered (6, 7, 8, 9 or 10 membered) aryl, for example, phenyl and naphthyl, and preferably phenyl. The aryl ring can be fused to the ring of heteroaryl, heterocyclyl or cycloalkyl, wherein the ring bound to the parent structure is aryl ring. Non-limiting examples thereof include:

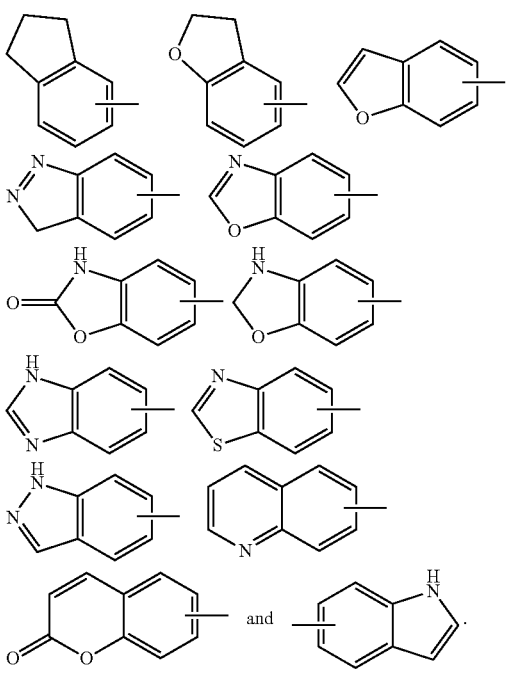

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "heteroaryl" refers to a 5 to 14 membered heteroaromatic system having 1 to 4 heteroatoms (1, 2, 3 or 4 heteroatoms) selected from the group consisting of O, S and N. The heteroaryl is preferably a 5 to 10 membered (5, 6, 7, 8, 9 or 10 membered) heteroaryl, more preferably a 5 or 6 membered heteroaryl, for example furyl, thienyl, pyridyl, pyrrolyl, N-alkylpyrrolyl, pyrimidinyl, pyrazinyl, imidazolyl, tetrazolyl and the like. The heteroaryl ring can be fused to the ring of aryl, heterocyclyl or cycloalkyl, wherein the ring bound to the parent structure is heteroaryl ring. Non-limiting examples thereof include:

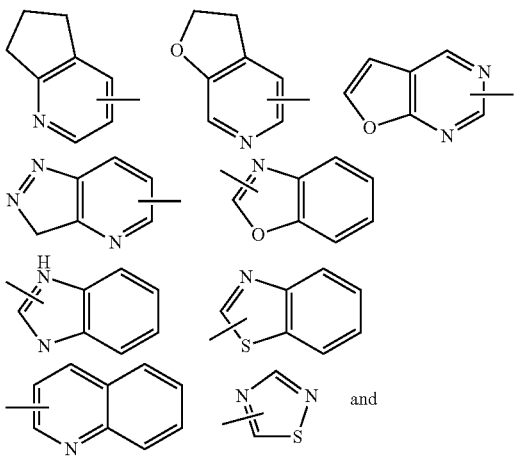

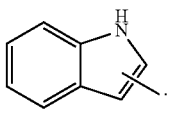

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio and heterocyclylthio.

The term "amino protecting group" refers to a group which prevents an amino group from reaction when other parts of the molecular are subject to a reaction, and can be easily removed. Non-limiting examples include 9-fluorenylmethyloxycarbonyl, tert-butoxycarbonyl, acetyl, benzyl, allyl, p-methoxybenzyl and the like. These groups can be optionally substituted by one to three substituent(s) (one, two or three substituent(s)) selected from the group consisting of halogen, alkoxy and nitro. The amino protecting group is preferably 9-fluorenylmethyloxycarbonyl.

The term "haloalkyl" refers to an alkyl group substituted by one or more halogen(s), wherein the alkyl is as defined above.

The term "deuterated alkyl" refers to an alkyl group substituted by one or more deuterium atom(s), wherein the alkyl is as defined above.

The term "hydroxyalkyl" refers to an alkyl group substituted by one or more hydroxy(s), wherein the alkyl is as defined above.

The term "hydroxy" refers to an —OH group.

The term "halogen" refers to fluorine, chlorine, bromine or iodine.

The term "amino" refers to a —NH$_2$ group.

The term "nitro" refers to a —NO$_2$ group.

The term "cyano" refers to a —CN group.

The term "amide" refers to a —C(O)N(alkyl) or —C(O)N(cycloalkyl) group, wherein the alkyl and cycloalkyl are as defined above.

The term "alkoxycarbonyl" refers to a —C(O)O(alkyl) or —C(O)O(cycloalkyl) group, wherein the alkyl and cycloalkyl are as defined above.

The present disclosure also comprises the compounds of formula (I) in various deuterated forms. Each of the available hydrogen atoms attached to the carbon atom can be independently replaced by a deuterium atom. Those skilled in the art can synthesize a compound of formula (I) in a deuterated form with reference to the relevant literatures. The compound of formula (I) in deuterated form can be prepared by employing commercially available deuterated raw materials, or they can be synthesized by conventional techniques with deuterated reagents including, but not limited to, deuterated borane, trideuterated borane in tetrahydrofuran, deuterated lithium aluminum hydride, deuterated iodoethane, deuterated iodomethane and the like.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1, 2 or 3 hydrogen atoms, independently substituted by a corresponding number of substituents. It goes without saying that the substituents only exist in their possible chemical position. The person skilled in the art is able to determine whether the substitution is possible or impossible by experiments or theory without excessive effort. For example, the combination of amino or hydroxy having free hydrogen and carbon atoms having unsaturated bonds (such as olefinic) may be unstable.

The term "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

The term "pharmaceutically acceptable salt" or "pharmaceutical salt" refers to a salt of the ligand-drug conjugate of the present disclosure or a salt of the compound of the present disclosure, which is safe and effective in mammals and has the desired biological activity. The ligand-drug conjugate of the present disclosure contains at least one amino, so it can form a salt with an acid. Non-limiting examples of pharmaceutically acceptable salts include hydrochloride, hydrobromide, hydroiodide, sulfate, bisulfate, citrate, acetate, succinate, ascorbate, oxalate, nitrate, sorbate, hydrogen phosphate, dihydrogen phosphate, salicylate, hydrogen citrate, tartrate, maleate, fumarate, formate, benzoate, methanesulfonate, ethanesulfonate, benzenesulfonate, p-toluenesulfonate.

The term "solvate" refers to a pharmaceutically acceptable solvate formed by a ligand-drug conjugate of the present disclosure with one or more solvent molecule(s). Non-limiting examples of solvent molecules include water, ethanol, acetonitrile, isopropanol, DMSO, ethyl acetate.

The term "drug loading" refers to the average number of cytotoxic drugs loaded on each ligand in the compound of formula (I), and can also be expressed as the ratio of the number of drug to the number of antibody. The drug loading can range from 0 to 12, preferably from 1 to 10 cytotoxic drugs (D) per ligand (Pc). In an embodiment of the present disclosure, the drug loading is expressed as n, also known as DAR value, and exemplary values can be an average of 1, 2, 3, 4, 5, 6, 7, 8, 9, 10. The average number of drugs per ADC molecule after coupling reaction can be determined by conventional methods such as UV/visible spectroscopy, mass spectrometry, ELISA test and HPLC characterization.

In an embodiment of the present disclosure, the cytotoxic drug is conjugated to the N-terminal amino and/or the ε-amino of lysine residues of the ligand via a linking unit. Typically, the number of drug molecules conjugated to the antibody in a coupling reaction will be less than the theoretical maximum.

The following non-limiting methods can be used to control the loading of the ligand-cytotoxic drug conjugates:
(1) controlling the molar ratio of the linking reagent to the monoclonal antibody,
(2) controlling the reaction time and temperature,
(3) selecting different reaction reagents.

The preparation of conventional pharmaceutical compositions can be found in the Chinese Pharmacopoeia.

The term "carrier" used in the composition of the present disclosure refers to a system that can change the way a drug enters the human body and distribution, control the drug release rate, and deliver the drug to the targeted organ. Drug carrier release and targeting systems can reduce drug degradation and loss, reduce side effects and improve bioavailability. For example, the polymer surfactants which can be used as carriers can be self-assembled to form various forms of aggregates due to their unique amphiphilic structure. Preferred examples include micelles, microemulsions, gels, liquid crystals, vesicles and the like. These aggregates have the ability to encapsulate drug molecules, while having good permeability to the membrane, and can be used as an excellent drug carrier.

The term "excipient" is an adjunct in a pharmaceutical formulation other than the main drug, which can also be referred to as an adjuvant, such as adhesives, fillers, disintegrants, lubricants in tablets; matrix parts in the semi-solid preparations ointment and cream; preservatives, antioxidants, flavoring agents, fragrances, co-solvents, emulsifiers, solubilizers, osmotic pressure regulators, colorants in liquid preparations and the like.

The term "diluent", also known as filler, is primarily intended to increase the weight and volume of the tablet. The addition of diluent ensures a certain volume, reduces the dose deviation of the main components, and improves the compression profile of the drug. When the tablet contains an oily component, an absorbent is added to absorb the oily substance, thereby keeping the "dry" state to facilitate tablet formation. For example, diluent includes starch, lactose, inorganic salts of calcium, microcrystalline cellulose and the like.

The pharmaceutical composition can be in the form of a sterile injectable aqueous solution. Acceptable vehicles or solvents that can be used are water, Ringer's solution or isotonic sodium chloride solution. The sterile injectable formulation can be a sterile injectable oil-in-water microemulsion in which the active ingredient is dissolved in the oil phase. For example, the active ingredient is dissolved in a mixture of soybean oil and lecithin. The oil solution is then added to a mixture of water and glycerin, and processed to form a micro-emulsion. The injectable solution or microemulsion can be introduced into a patient's bloodstream by local bolus injection. Alternatively, the solution and microemulsion are preferably administrated in a manner that maintains a constant circulating concentration of the compound of the present disclosure. In order to maintain this constant concentration, a continuous intravenous delivery device can be used. An example of such a device is Deltec CADD-PLUS.™. 5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent, for example, a solution prepared in 1,3-butanediol. Moreover, sterile fixed oils can easily be used as a solvent or suspending medium. For this purpose, any blending fixed oils including synthetic mono- or di-glyceride can be employed. Moreover, fatty acids, such as oleic acid, can also be employed in the preparation of an injection.

The present disclosure relates to a cleavable linker arm with a specific structure and an active substance with a specific structure, and an antibody-drug conjugate (ADC) composed of a linker arm, an active substance and an antibody. This ADC is a complex formed by linking a toxic substance to an antibody via a spacer. The antibody-drug conjugate (ADC) is degraded in the body to release active molecules, thereby showing an anti-tumor effect.

II. Synthesis Method

In order to achieve the object of the present disclosure, the present disclosure applies the following technical solution.

A method for preparing the compound of formula (Pc-$L_a$-Y-Dr), comprises the following step of:

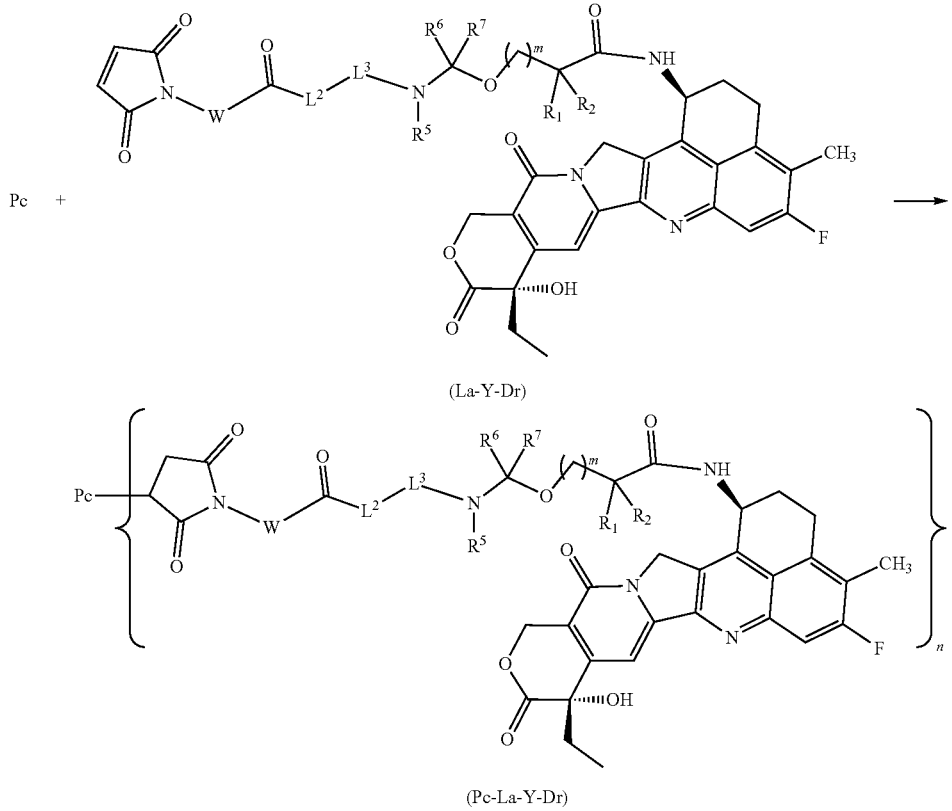

Pc is coupled with the compound of formula ($L_a$-Y-Dr) after reduction to obtain the compound of formula (Pc-$L_a$-Y-Dr); the reducing agent is preferably TCEP, particularly, it is preferable to reduce the disulfide bond on the antibody; wherein:

Pc, W, $L^2$, $L^3$, $R^1$, $R^2$, $R^5$~$R^7$, m and n are as defined in formula (Pc-$L_a$-Y-Dr).

The details of one or more embodiments of the present disclosure are set forth in the above specification. Although any methods and materials similar or equivalent to those described herein can be used in the practice or testing of the present disclosure, preferred methods and materials are described below. Through the specification and claims, other features, objectives and advantages of the present disclosure will be apparent. In the specification and claims, unless the context clearly indicates otherwise, the singular form includes the plural referent. Unless otherwise specified, all technical and scientific terms used herein are consistent with the common understanding of those of ordinary skill in the art to which the present disclosure belongs. All patents and publications cited in the specification are incorporated herein by reference. The following examples are presented to more fully illustrate the preferred embodiments of the present disclosure. These embodiments should not be construed as limiting the scope of the present disclosure in any way, and the scope of the present disclosure is defined by the claims.

The experimental methods in the examples of the present disclosure for which the specific conditions are not indicated were carried out according to conventional conditions or the conditions recommended by the material or product manufacturers. The reagents for which the specific sources are not indicated are conventional reagents purchased from market.

The structures of the compounds are identified by nuclear magnetic resonance (NMR) or mass spectrometry (MS). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), and the internal standard is tetramethylsilane (TMS). Chemical shifts are given in $10^{-6}$ (ppm).

MS is determined by a FINNIGAN LCQAd (ESI) mass spectrometer (manufacturer: Thermo, type: Finnigan LCQ advantage MAX).

UPLC is determined by a Waters Acquity UPLC SQD liquid chromatograph/mass spectrometer.

High performance liquid chromatography (HPLC) is determined on an Agilent 1200DAD high pressure liquid chromatograph (Sunfire C18 150×4.6 mm chromatographic column), and a Waters 2695-2996 high pressure liquid chromatograph (Gimini C18 150×4.6 mm chromatographic column).

UV-HPLC is determined on a Thermo nanodrop2000 UV spectrophotometer.

The proliferation inhibition rates and $IC_{50}$ values are determined by a PHERA starFS microplate reader (BMG Co., Germany).

Yantai Huanghai HSGF254 or Qingdao GF254 silica gel plate is used as the thin-layer silica gel chromatography (TLC) plate. The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is generally used as a carrier for column chromatography.

The known starting materials of the present disclosure can be prepared by the known methods in the art, or can be purchased from ABCR GmbH & Co. KG, Acros Organnics, Aldrich Chemical Company, Accela ChemBio Inc., Dari chemical Company etc.

Unless otherwise stated, the reactions are carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reaction is performed on a Parr 3916EKX hydrogenation instrument and a Qinglan QL-500 hydrogen generator or HC2-SS hydrogenation instrument.

In hydrogenation reactions, the reaction system is generally vacuumed and filled with hydrogen, and the above operation is repeated three times.

CEM Discover-S 908860 type microwave reactor is used in microwave reactions.

Unless otherwise stated, the solution of the reaction refers to an aqueous solution.

Unless otherwise stated, the reaction temperature of the reaction is room temperature.

Room temperature from 20° C. to 30° C. is the most suitable reaction temperature.

Preparation of PBS buffer (pH=6.5) in the examples: 8.5 g of $KH_2PO_4$, 8.56 g of $K_2HPO_4 \cdot 3H_2O$, 5.85 g of NaCl and 1.5 g of EDTA are set to 2 L in a flask, the mixture is subjected to ultrasonication to dissolve completely, and shaked well to give the buffer.

The eluent system in column chromatography and the developing solvent system in thin layer chromatography for purification of the compounds include: A: dichloromethane and isopropanol system, B: dichloromethane and methanol system, C: petroleum ether and ethyl acetate system. The ratio of the volume of the solvent is adjusted according to the polarity of the compounds, and a small quantity of acidic reagent or alkaline reagent such as triethylamine could also be added for adjustment.

Some of the compounds of the present disclosure are characterized by Q-TOF LC/MS. Regarding to Q-TOF LC/MS, Agilent 6530 Accurate-Mass Quadrupole-Time of Flight Mass Spectrometer and Agilent 1290-Infinity UHPLC (Agilent Poroshell 300SB-C8 5 μm, 2.1×75 mm column) are used.

Example 1

N-((1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-1-hydroxycyclopropane-1-carboxamide 1

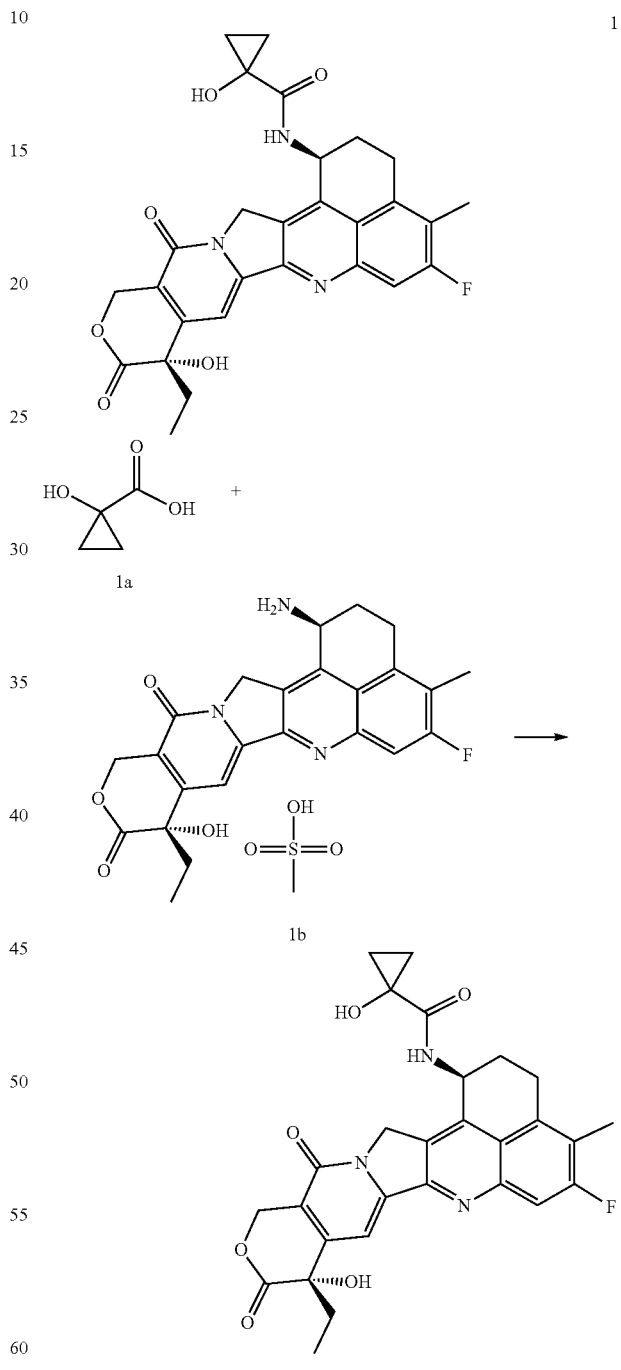

1 mL of N,N-dimethylformamide was added to exatecan methanesulfonate 1b (2.0 mg, 3.76 μmol, prepared according to the method disclosed in the patent application "EP0737686A1"), and the solution was cooled to 0-5° C.

under an ice-water bath. One drop of triethylamine was added dropwise, and the reaction solution was stirred until clear. 1-Hydroxycyclopropylcarboxylic acid 1a (1.4 mg, 3.7 μmol, prepared according to the known method disclosed in "Tetrahedron Letters, 25(12), 1269-72; 1984") and 4-(4,6-dimethoxy-1,3,5-triazin-2-yl)-4-methylmorpholinium chloride (3.8 mg, 13.7 μmol) were added successively to the reaction solution. After completion of the addition, the reaction solution was stirred at 0-5° C. for 2 hours. 5 mL of water was added to the reaction solution to quench the reaction, and the reaction solution was extracted with ethyl acetate (8 mL×3). The organic phases were combined, washed with saturated sodium chloride solution (5 mL×2), dried over anhydrous sodium sulfate and filtered. The filtrate was concentrated under reduced pressure, and the resulting residues were purified by thin layer chromatography with developing solvent system B to obtain the title product 1 (1.6 mg, yield: 82.1%).

MS m/z (ESI): 520.2 [M+1].

$^1$H NMR (400 MHz, CDCl$_3$): δ 7.90-7.84 (m, 1H), 7.80-7.68 (m, 1H), 5.80-5.70 (m, 1H), 5.62-5.54 (m, 2H), 5.44-5.32 (m, 2H), 5.28-5.10 (m, 2H), 3.40-3.15 (m, 3H), 2.44 (s, 3H), 2.23 (t, 1H), 2.06-1.75 (m, 2H), 1.68-1.56 (m, 1H), 1.22-1.18 (m, 2H), 1.04-0.98 (m, 2H), 0.89 (t, 3H).

Example 2

(S)-2-Cyclopropyl-N-((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)-2-hydroxyacetamide 2-A (R)-2-Cyclopropyl-N-((1S,9S)-9-ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)-2-hydroxyacetamide 2-B

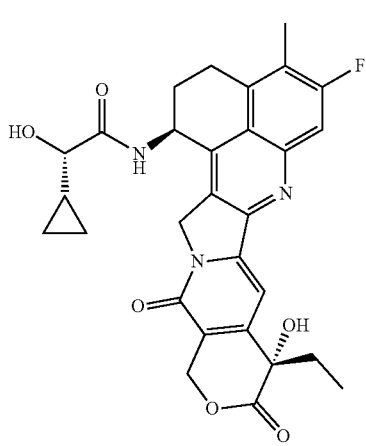

2-A

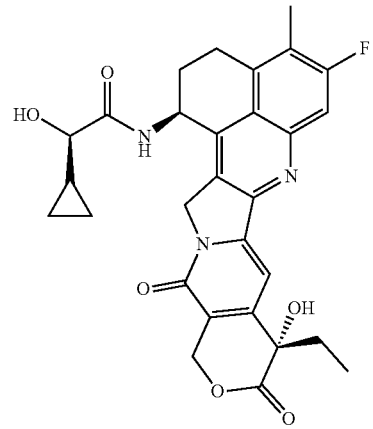

2-B

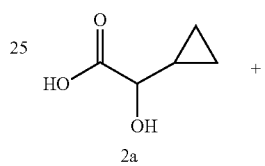

2a

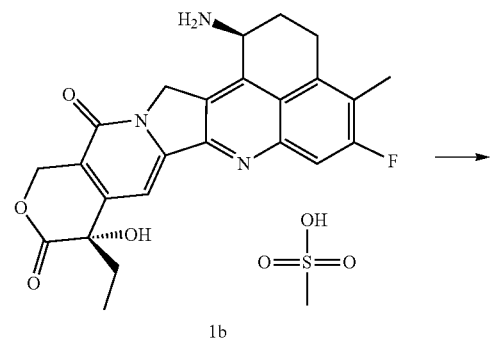

1b

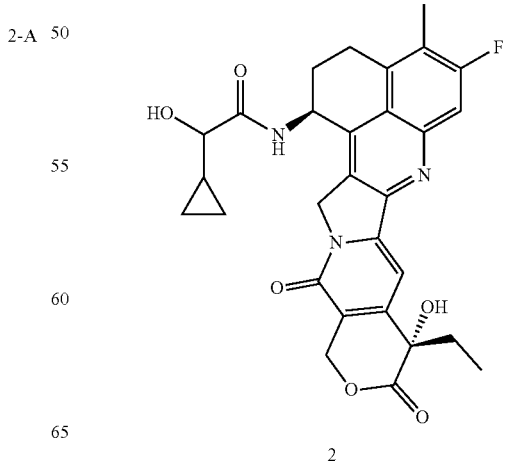

2

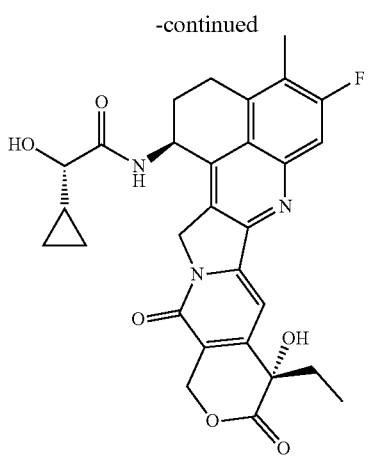

2-A

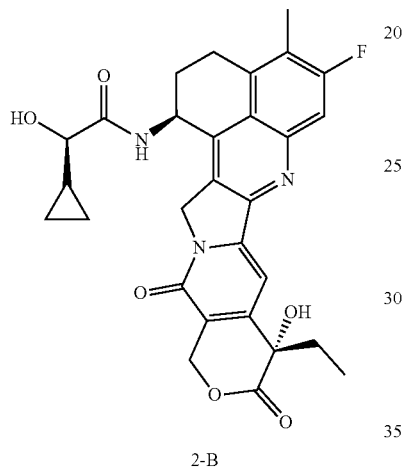

2-B 2 mL of ethanol and 0.4 mL of N,N-dimethylformamide were added to 1b (4 mg, 7.53 μmol). The solution was purged with argon three times, and cooled to 0-5° C. under an ice-water bath. 0.3 mL of N-methylmorpholine was added dropwise, and the reaction solution was stirred until clear. 2-Cyclopropyl-2-hydroxyacetic acid 2a (2.3 mg, 19.8 μmol, prepared according to the method disclosed in the patent application "WO2013106717"), 1-hydroxybenzotriazole (3 mg, 22.4 μmol) and 1-(3-dimethylaminopropyl)-3-ethylcarbodiimide hydrochloride (4.3 mg, 22.4 μmol) were added successively to the reaction solution. After completion of the addition, the reaction solution was stirred at 0-5° C. for one hour. The ice-water bath was removed, and the reaction solution was heated to 30° C. and stirred for 2 hours. The reaction solution was concentrated under reduced pressure, and the resulting crude compound 2 was purified by high performance liquid chromatography (separation conditions: column: XBridge Prep C18 OBD 5 μm 19*250 mm; mobile phase: A-water (10 mmol NH$_4$OAc), B-acetonitrile, gradient elution, flow rate: 18 mL/min). The corresponding fractions were collected, and concentrated under reduced pressure to obtain the title product (1.5 mg, 1.5 mg).

MS m/z (ESI): 534.0 [M+1].

Compound 2-B with Single Configuration (Having Shorter Retention Time)

UPLC analysis: retention time: 1.06 minutes, purity: 88% (column: ACQUITY UPLC BEHC18 1.7 μm 2.1*50 mm, mobile phase: A-water (5 mmol NH$_4$OAc), B-acetonitrile).

$^1$H NMR (400 MHz, DMSO-d$_6$): δ 8.37 (d, 1H), 7.76 (d, 1H), 7.30 (s, 1H), 6.51 (s, 1H), 5.58-5.56 (m, 1H), 5.48 (d, 1H), 5.41 (s, 2H), 5.32-5.29 (m, 1H), 3.60 (t, 1H), 3.19-3.13 (m, 2H), 2.38 (s, 3H), 2.20-2.14 (m, 1H), 1.98 (q, 2H), 1.87-1.83 (m, 1H), 1.50-1.40 (m, 1H), 1.34-1.28 (m, 1H), 0.86 (t, 3H), 0.50-0.39 (m, 4H).

Compound 2-A with Single Configuration (Having Longer Retention Time)

UPLC analysis: retention time: 1.10 minutes, purity: 86% (column: ACQUITY UPLC BEHC18 1.7 μm 2.1*50 mm, mobile phase: A-water (5 mmol NH$_4$OAc), B-acetonitrile).

$^1$H NMR (400 MHz, DMSO-d$_6$): δ 8.35 (d, 1H), 7.78 (d, 1H), 7.31 (s, 1H), 6.52 (s, 1H), 5.58-5.53 (m, 1H), 5.42 (s, 2H), 5.37 (d, 1H), 5.32 (t, 1H), 3.62 (t, 1H), 3.20-3.15 (m, 2H), 2.40 (s, 3H), 2.25-2.16 (m, 1H), 1.98 (q, 2H), 1.87-1.82 (m, 1H), 1.50-1.40 (m, 1H), 1.21-1.14 (m, 1H), 0.87 (t, 3H), 0.47-0.35 (m, 4H).

Example 3

(S)—N-((1S,9S)-9-Ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)-3,3,3-trifluoro-2-hydroxypropanamide 3-A (R)—N-((1S,9S)-9-Ethyl-5-fluoro-9-hydroxy-4-methyl-10,13-dioxo-1,2,3,9,10,12,13,15-octahydrobenzo[de]pyrano[3',4':6,7]indolizino[1,2-b]quinolin-1-yl)-3,3,3-trifluoro-2-hydroxypropanamide 3-B

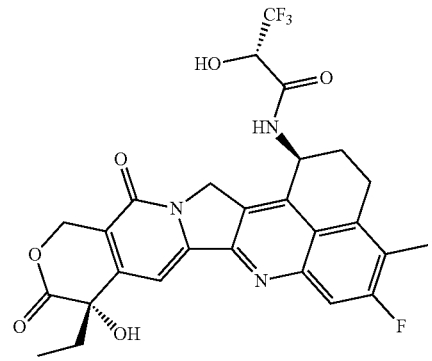

3-A

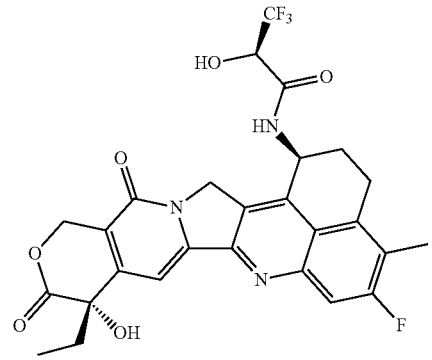

3-B

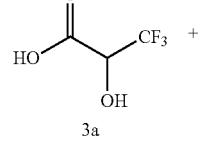

3a

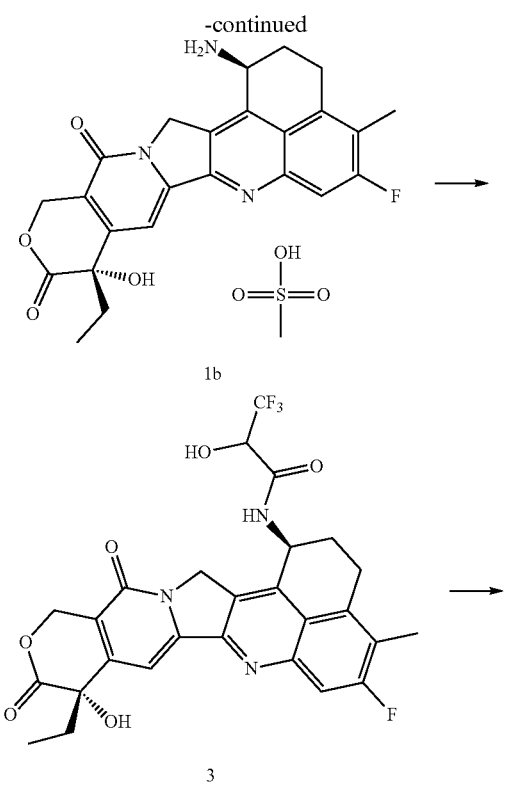

2 mL of ethanol and 0.4 mL of N,N-dimethylformamide were added to 1b (5.0 mg, 9.41 μmol), and the solution was cooled to 0-5° C. under an ice-water bath. 0.3 mL of N-methylmorpholine was added dropwise, and the reaction solution was stirred until clear. 3,3,3-Trifluoro-2-hydroxy-propionic acid 3a (4.1 mg, 28.4 μmol, supplier: Alfa), 1-hydroxybenzotriazole (3.8 mg, 28.1 μmol) and 1-(3-dimethylaminopropyl)-3-ethylcarbodiimide hydrochloride (5.4 mg, 28.2 μmol) were added successively to the reaction solution. After completion of the addition, the reaction solution was stirred at 0-5° C. for 10 minutes. The ice-water bath was removed, and the reaction solution was heated to 30° C. and stirred for 8 hours. The reaction solution was concentrated under reduced pressure, and the resulting crude compound 3 was purified by high performance liquid chromatography (separation conditions: column: XBridge Prep C18 OBD 5 μm 19*250 mm; mobile phase: A-water (10 mmol NH$_4$OAc), B-acetonitrile, gradient elution, flow rate: 18 mL/min). The corresponding fractions were collected, and concentrated under reduced pressure to obtain the title products (1.5 mg, 1.5 mg).

MS m/z (ESI): 561.9 [M+1].

Compound with Single Configuration (Having Shorter Retention Time)

UPLC analysis: retention time: 1.11 minutes, purity: 88% (column: ACQUITY UPLC BEHC18 1.7 μm 2.1*50 mm, mobile phase: A-water (5 mmol NH$_4$OAc), B-acetonitrile).

$^1$H NMR (400 MHz, DMSO-d$_6$): δ 8.94 (d, 1H), 7.80 (d, 1H), 7.32 (s, 1H), 7.20 (d, 1H), 6.53 (s, 1H), 5.61-5.55 (m, 1H), 5.45-5.23 (m, 3H), 5.15-5.06 (m, 1H), 4.66-4.57 (m, 1H), 3.18-3.12 (m, 1H), 2.40 (s, 3H), 2.26-2.20 (m, 1H), 2.16-2.08 (m, 1H), 2.02-1.94 (m, 1H), 1.89-1.82 (m, 1H), 1.50-1.40 (m, 1H), 0.87 (t, 3H).

Compound with Single Configuration (Having Longer Retention Time)

UPLC analysis: retention time: 1.19 minutes, purity: 90% (column: ACQUITY UPLC BEHC18 1.7 μm 2.1*50 mm, mobile phase: A-water (5 mmol NH$_4$OAc), B-acetonitrile).

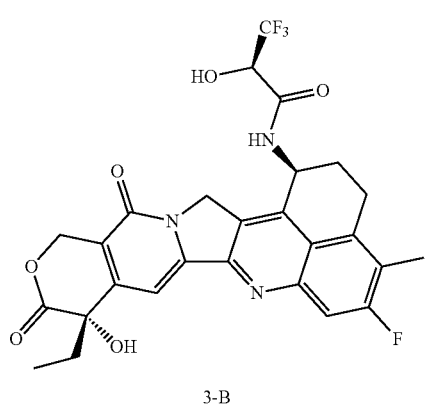

$^1$H NMR (400 MHz, DMSO-d$_6$): δ 8.97 (d, 1H), 7.80 (d, 1H), 7.31 (s, 1H), 7.16 (d, 1H), 6.53 (s, 1H), 5.63-5.55 (m, 1H), 5.45-5.20 (m, 3H), 5.16-5.07 (m, 1H), 4.66-4.57 (m, 1H), 3.18-3.12 (m, 1H), 2.40 (s, 3H), 2.22-2.14 (m, 1H), 2.04-1.95 (m, 2H), 1.89-1.82 (m, 1H), 1.50-1.40 (m, 1H), 0.87 (t, 3H).

Example 4
1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 4
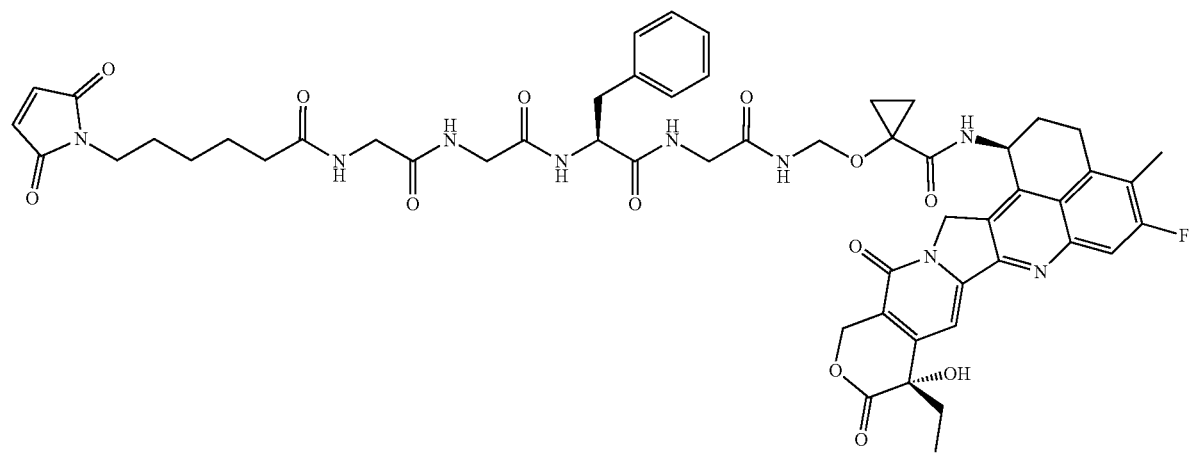
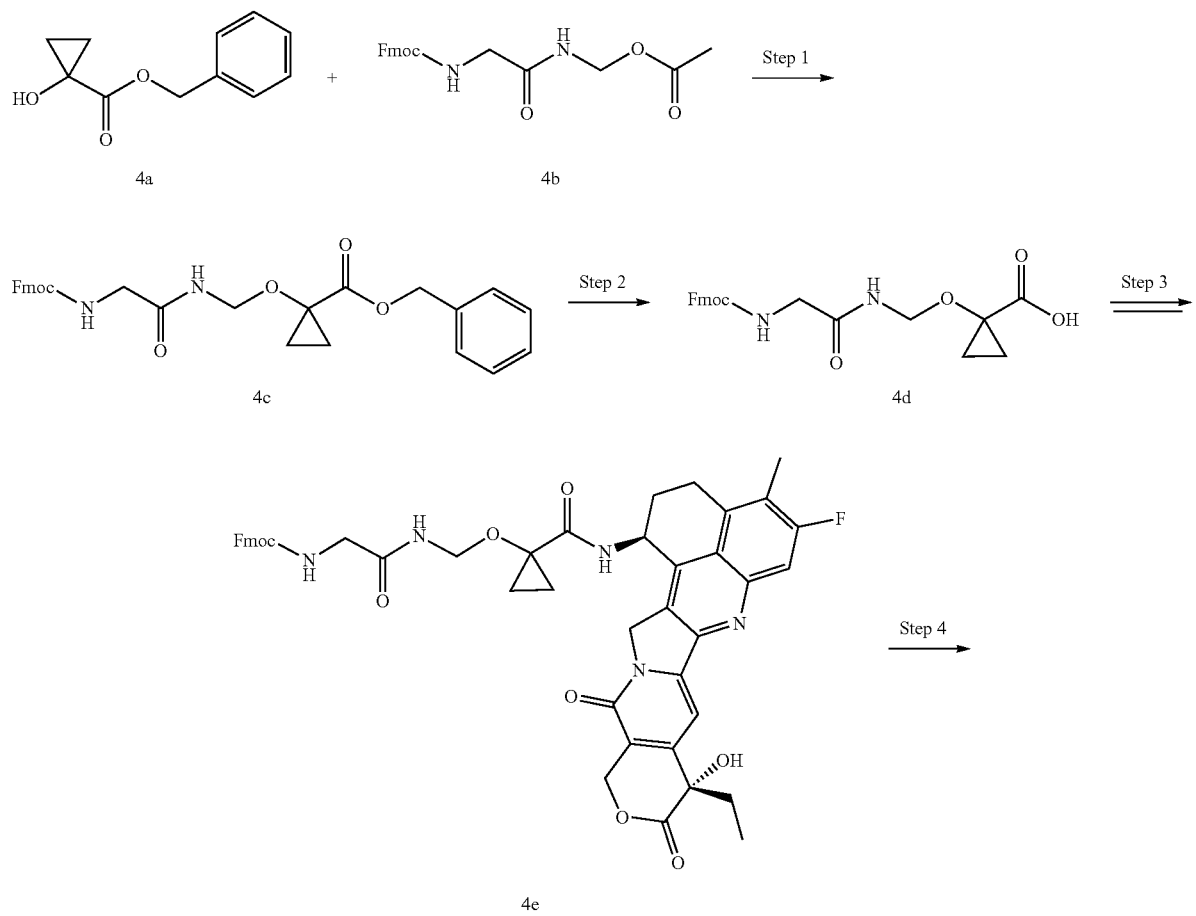

-continued

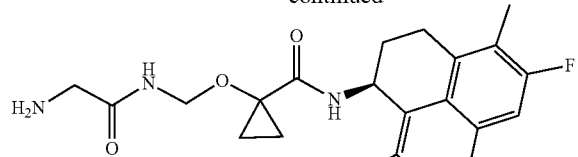

4f

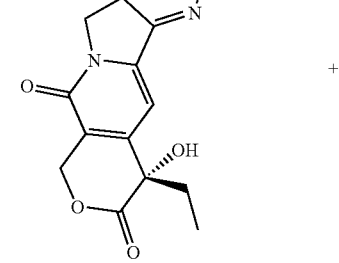

4g

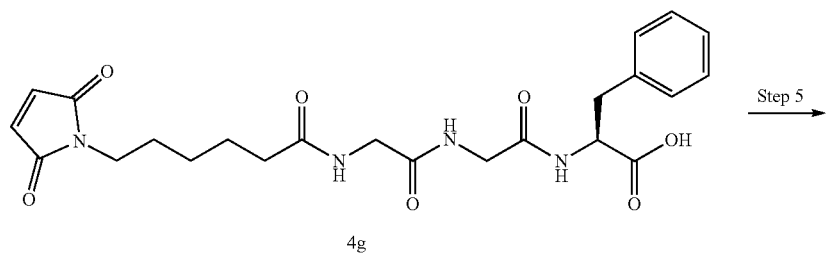

4

Step 1

Benzyl 1-((2-((((9H-fluoren-9-yl)methoxy)carbonyl)amino)acetamido)methoxy)cyclopropane-1-carboxylate 4c Benzyl 1-hydroxycyclopropane-1-carboxylate 4a (104 mg, 0.54 mmol, prepared according to the method disclosed in the patent application "US2005/20645") and (2-((((9H-fluoren-9-yl)methoxy)carbonyl)amino)acetamido)methyl acetate 4b (100 mg, 0.27 mmol, prepared according to the method disclosed in the patent application "CN105829346A") were added to a reaction flask, followed by the addition of 5 mL of tetrahydrofuran. The reaction solution was purged with argon three times and cooled to 0-5° C. under an ice-water bath, followed by the addition of potassium tert-butoxide (61 mg, 0.54 mmol). The ice-water bath was removed, and the reaction solution was warmed up to room temperature and stirred for 10 minutes. 20 mL of ice water was added to the reaction solution, which was then extracted with ethyl acetate (5 mL×2) and chloroform (5 mL×5). The organic phases were combined and concentrated. The resulting residues were dissolved in 3 mL of 1,4-dioxane and then added with 0.6 mL of water, sodium bicarbonate (27 mg, 0.32 mmol) and 9-fluorene methyl chloroformate (70 mg, 0.27 mmol), and the reaction solution was stirred at room temperature for 1 hour. 20 mL of water was added, and the reaction solution was extracted with ethyl acetate (8 mL×3). The organic phase was washed with saturated sodium chloride solution (20 mL), dried over anhydrous sodium sulfate and filtered. The filtrate was concentrated under reduced pressure, and the resulting residues were purified by silica gel column chromatography with developing solvent system B to obtain the title product 4c (100 mg, yield: 73.6%).

MS m/z (ESI): 501.0 [M+1].

Step 2

1-((2-((((9H-Fluoren-9-yl)methoxy)carbonyl)amino) acetamido)methoxy)cyclopropane-1-carboxylic acid 4d 4c (50 mg, 0.10 mmol) was dissolved in 3 mL of a mixed solvent of tetrahydrofuran and ethyl acetate (V:V=2:1), followed by the addition of palladium on carbon (25 mg, content: 10%). The reaction solution was purged with hydrogen three times and stirred at room temperature for 1 hour. The reaction solution was filtered through celite, and the filter cake was rinsed with tetrahydrofuran. The filtrate was concentrated to obtain the title product 4d (41 mg, yield: 100%).

MS m/z (ESI): 411.0 [M+1].

Step 3

(9H-Fluoren-9-yl)methyl (2-(((1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7] indolizino[1,2-b]quinolin-1-yl)carbamoyl) cyclopropoxy)methyl)amino)-2-oxoethyl)carbamate 4e 1b (7 mg, 0.013 mmol) was added to a reaction flask, followed by the addition of 1 mL of N,N-dimethylformamide. The solution was purged with argon three times, and cooled to 0-5° C. under an ice-water bath. One drop of triethylamine, 4d (7 mg, 0.017 mmol) in 0.5 mL of N,N-dimethylformamide, and 4-(4,6-dimethoxy-1,3,5-triazin-2-yl)-4-methylmorpholinium chloride (7 mg, 0.026 mmol) were added, and the reaction solution was stirred under an ice bath for 35 minutes. 10 mL of water was added, and the reaction solution was extracted with ethyl acetate (5 mL×3). The organic phase was washed with saturated sodium chloride solution (10 mL), dried over anhydrous sodium sulfate and filtered. The filtrate was concentrated under reduced pressure, and the resulting residues were purified by thin layer chromatography with developing solvent system B to obtain the title product 4e (8.5 mg, yield: 78.0%).

MS m/z (ESI): 828.0 [M+1].

Step 4

1-((2-Aminoacetamido)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 4f 4e (4 mg, 4.84 μmol) was dissolved in 0.2 mL of dichloromethane, followed by the addition of 0.1 mL of diethylamine. The reaction solution was stirred at room temperature for 2 hours. The reaction solution was concentrated under reduced pressure. 2 mL of toluene was added and the solution was concentrated under reduced pressure, which was repeated twice. 3 mL of n-hexane was added to pulp, and the upper layer of hexane was poured, which was repeated three times. The mixture was concentrated under reduced pressure to obtain the crude title product 4f (2.9 mg), which was used directly in the next step without purification.

MS m/z (ESI): 606.0 [M+1].

Step 5

1-(((S)-7-Benzyl-20-(2,5-dioxo-2,5-dihydro-1H-pyrrol-1-yl)-3,6,9,12,15-pentaoxo-2,5,8,11,14-pentaazaicosyl)oxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)cyclopropane-1-carboxamide 4

The crude compound 4f (2.9 mg, 4.84 μmol) was dissolved in 0.5 mL of N,N-dimethylformamide. The solution was purged with argon three times, and cooled to 0-5° C. under an ice-water bath. (S)-2(-2-(-2-(6-(2,5-Dioxo-1H-pyrrol-1-yl)hexanamido)acetamido)acetamido)-3-phenylpropionic acid 4g (2.7 mg, 5.80 μmol, prepared according to the method disclosed in the patent application "EP2907824") in 0.3 mL of N,N-dimethylformamide, and 4-(4,6-dimethoxy-1,3,5-triazin-2-yl)-4-methylmorpholinium chloride (2.7 mg, 9.67 μmol) were added, and the reaction solution was stirred under an ice bath for 30 minutes. The ice bath was removed, and the reaction solution was warmed up to room temperature and stirred for 15 minutes. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title product 4 (2 mg, yield: 39.0%).

MS m/z (ESI): 1060.0 [M+1].

$^1$H NMR (400 MHz, DMSO-$d_6$): δ 9.01 (d, 1H), 8.77 (t, 1H), 8.21 (t, 1H), 8.08-7.92 (m, 2H), 7.73 (d, 1H), 7.28 (s, 1H), 7.24-7.07 (m, 4H), 6.98 (s, 1H), 6.50 (s, 1H), 5.61 (q, 1H), 5.40 (s, 2H), 5.32 (t, 1H), 5.12 (q, 2H), 4.62 (t, 1H), 4.52 (t, 1H), 4.40-4.32 (m, 1H), 3.73-3.47 (m, 8H), 3.16-3.04 (m, 2H), 2.89 (dd, 1H), 2.69-2.55 (m, 2H), 2.37-2.23 (m, 4H), 2.12-1.93 (m, 4H), 1.90-1.74 (m, 2H), 1.52-1.38 (m, 4H), 1.33-1.11 (m, 5H), 0.91-0.81 (m, 4H).

Example 5

N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 5-A N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 5-B

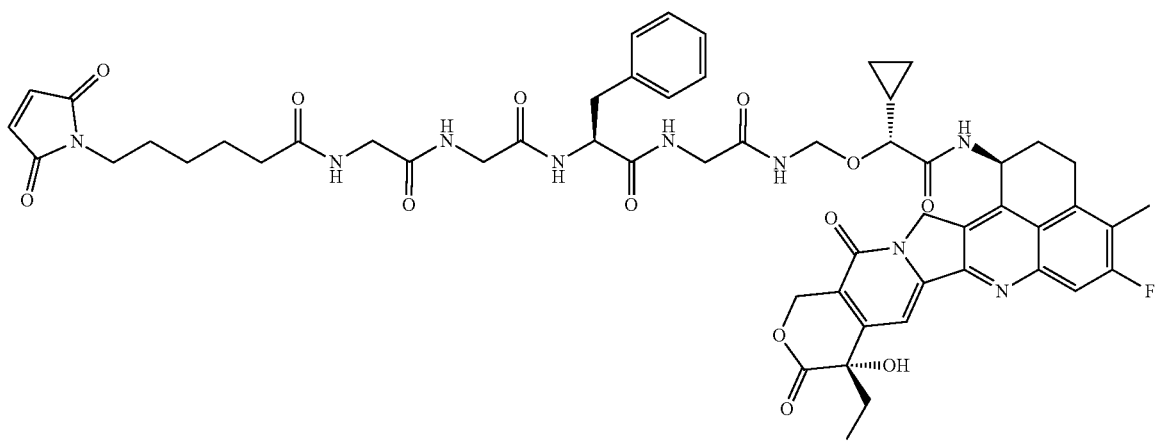

5-A

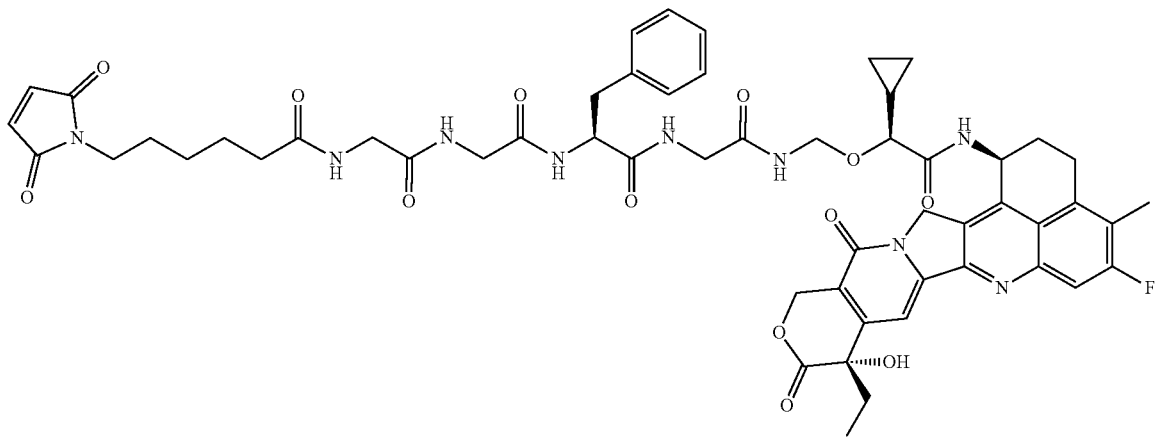

5-B

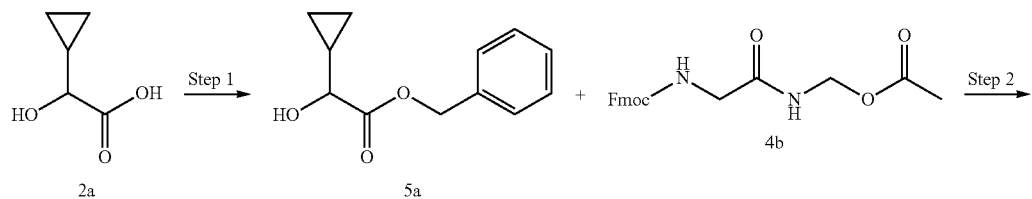

65 66
-continued
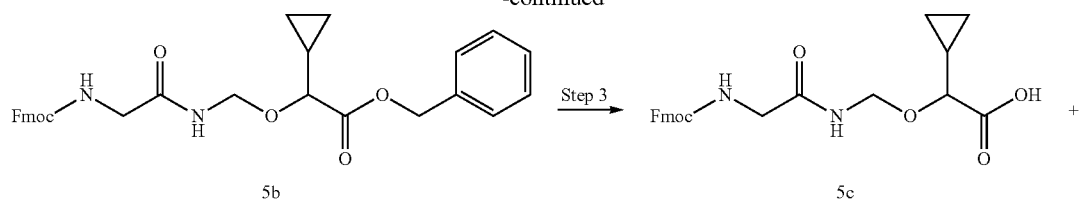
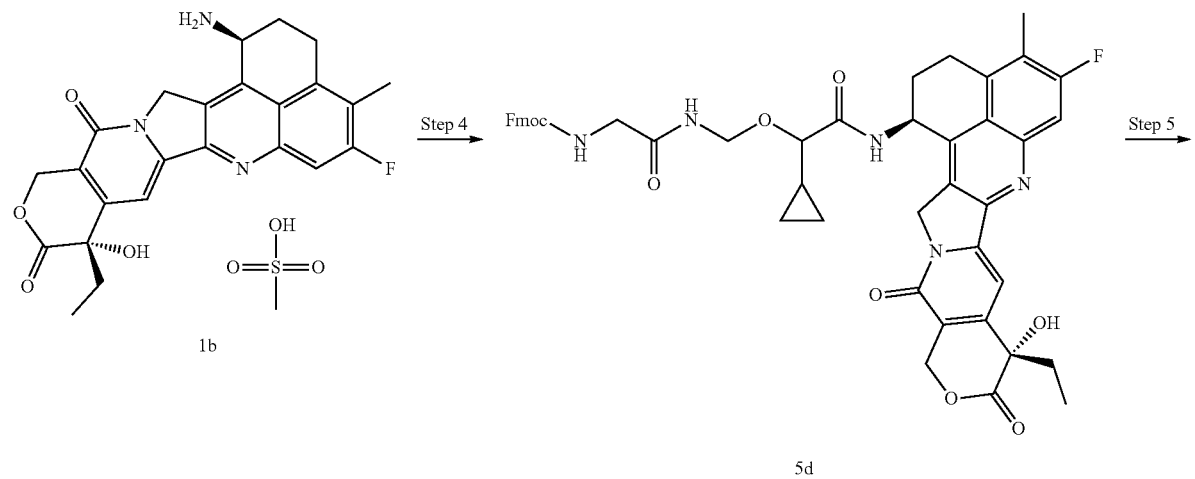
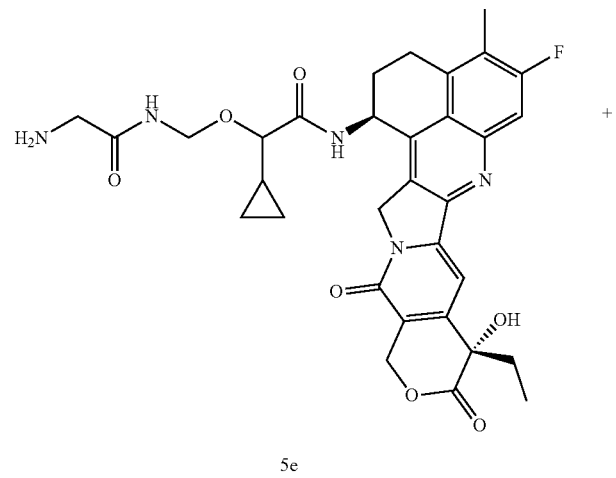
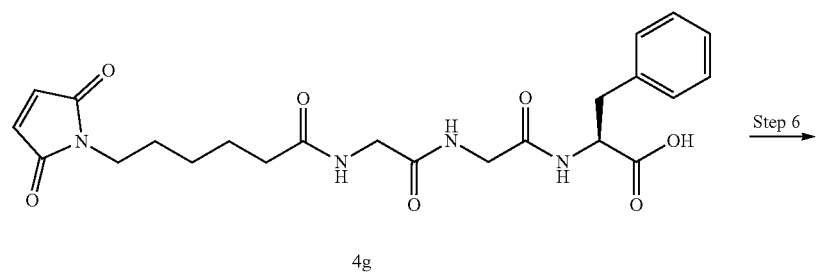

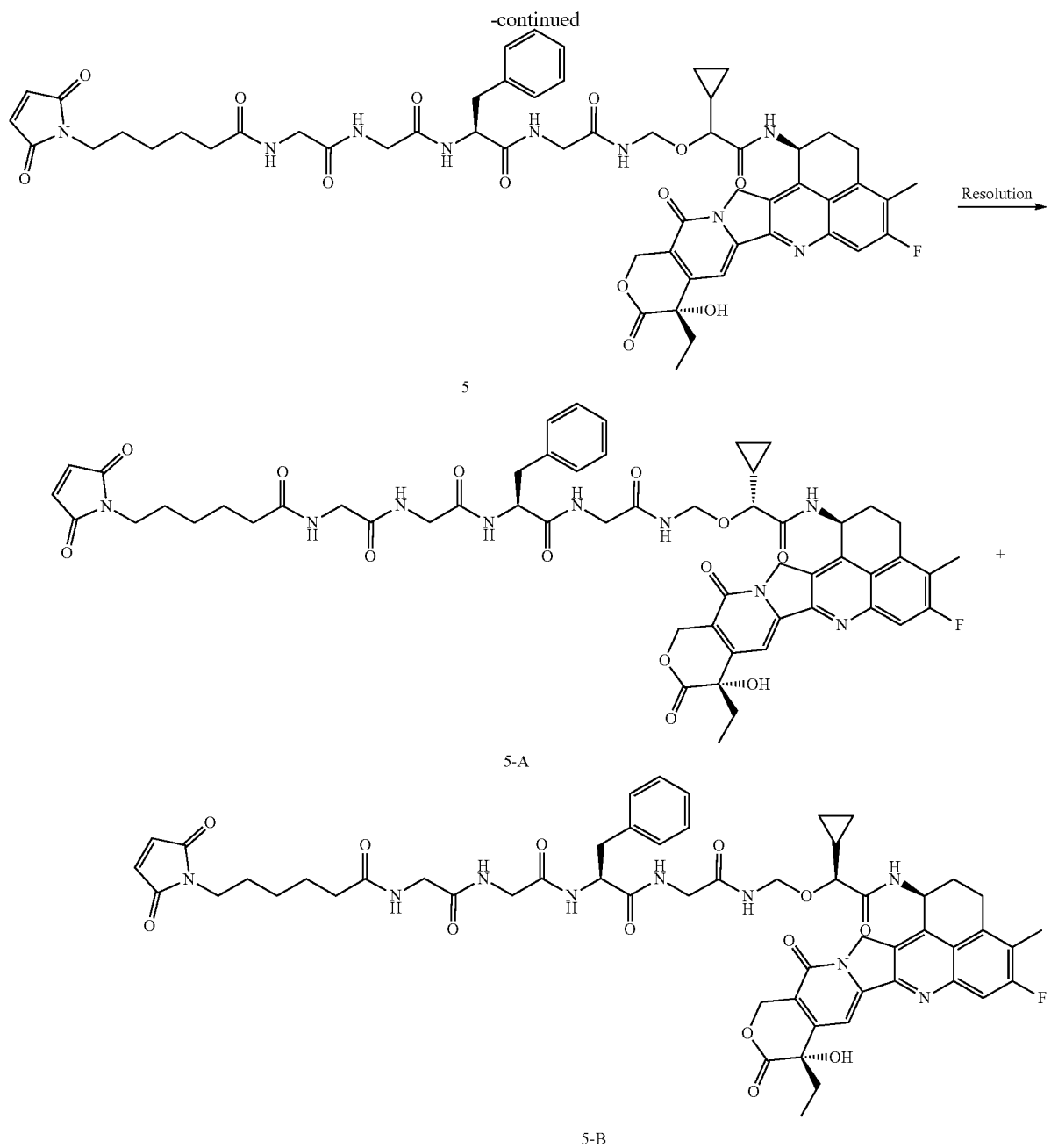

Step 1

Benzyl 2-cyclopropyl-2-hydroxyacetate 5a 2a (1.3 g, 11.2 mmol, prepared according to the method disclosed in the patent application "WO2013/106717") was dissolved in 50 mL of acetonitrile, and then added with potassium carbonate (6.18 g, 44.8 mmol), benzyl bromide (1.33 mL, 11.2 mmol) and tetrabutylammonium iodide (413 mg, 1.1 mmol) successively. The reaction solution was stirred at room temperature for 48 hours, and filtered through celite. The filter cake was rinsed with ethyl acetate (10 ml), and the filtrates were combined and concentrated under reduced pressure. The resulting residues were purified by silica gel column chromatography with developing solvent system C to obtain the title product 5a (2 g, yield: 86.9%).

Step 2

Benzyl 10-cyclopropyl-1-(9H-fluoren-9-yl)-3,6-dioxo-2,9-dioxa-4,7-diazaundecan-11-oate 5b 5a (120.9 mg, 0.586 mmol) and 4b (180 mg, 0.489 mmol) were added to a reaction flask, followed by the addition of 4 mL of tetrahydrofuran. The reaction solution was purged with argon three times and cooled to 0-5° C. under an ice-water bath. Potassium tert-butoxide (109 mg, 0.98 mmol) was added and the ice-water bath was removed. The reaction solution was warmed up to room temperature and stirred for 40 minutes. 10 mL of ice water was added to the reaction solution, which was then extracted with ethyl acetate (20 mL×2) and chloroform (10 mL×5). The organic phases were combined and concentrated. The resulting residues were dissolved in 4 mL of dioxane and then added with 2 mL of water, sodium bicarbonate (49.2 mg, 0.586 mmol) and 9-fluorene methyl chloroformate (126 mg, 0.49 mmol), and the reaction solution was stirred at room temperature for 2 hours. 20 mL of water was added, and the reaction solution was extracted with ethyl acetate (10 mL×3). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 5b (48 mg, yield: 19%).

MS m/z (ESI): 515.0 [M+1].

Step 3

10-Cyclopropyl-1-(9H-fluoren-9-yl)-3,6-dioxo-2,9-dioxa-4,7-diazaundecan-11-oic acid 5c 5b (20 mg, 0.038 mmol) was dissolved in 4.5 mL of a mixed solvent of tetrahydrofuran and ethyl acetate (V:V=2:1), followed by the addition of palladium on carbon (12 mg, content: 10%, dry). The reaction solution was purged with hydrogen three times and stirred at room temperature for 1 hour. The reaction solution was filtered through celite, and the filter cake was rinsed with ethyl acetate. The filtrate was concentrated to obtain the crude title product 5c (13 mg), which was used directly in the next step without purification.

MS m/z (ESI): 424.9 [M+1].

Step 4

(9H-Fluoren-9-yl)methyl (2-(((1-cyclopropyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-2-oxoethoxy)methyl)amino)-2-oxoethyl) carbamate 5d 1b (10 mg, 18.8 μmol) was added to a reaction flask, followed by the addition of 1 mL of N,N-dimethylformamide. The solution was purged with argon three times, and cooled to 0-5° C. under an ice-water bath. One drop of triethylamine, crude compound 5c (13 mg, 30.6 μmol) and 4-(4,6-dimethoxy-1,3,5-triazin-2-yl)-4-methylmorpholinium chloride (16.9 mg, 61.2 μmol) were added, and the reaction solution was stirred under an ice bath for 40 minutes. 10 mL of water was added, and the reaction solution was extracted with ethyl acetate (10 mL×3). The organic phases were combined. The organic phase was washed with saturated sodium chloride solution (10 mL×2), dried over anhydrous sodium sulfate and filtered. The filtrate was concentrated under reduced pressure. The resulting residues were purified by thin layer chromatography with developing solvent system B to obtain the title product 5d (19 mg, yield: 73.6%).

MS m/z (ESI): 842.1[M+1]

Step 5

2-((2-Aminoacetamido)methoxy)-2-cyclopropyl-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)acetamide 5e 5d (19 mg, 22.6 μmol) was dissolved in 2 mL of dichloromethane, followed by the addition of 1 mL of diethylamine. The reaction solution was stirred at room temperature for 2 hours. The reaction solution was concentrated under reduced pressure. 1 mL of toluene was added and the solution was concentrated under reduced pressure, which was repeated twice. 3 mL of n-hexane was added to the residues to pulp, and the supernatant was poured out after standing. The solid was retained. The solid residues were concentrated under reduced pressure by an oil pump until dryness to obtain the crude title product 5e (17 mg), which was used directly in the next step without purification.

MS m/z (ESI): 638.0[M+18].

Step 6

N-((2R,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 5-A N-((2S,10S)-10-Benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadecan-16-yl)-6-(2,5-dioxo-2,5-dihydro-1H-pyrrol-1-yl)hexanamide 5-B The crude compound 5e (13.9 mg, 22.4 μmol) was dissolved in 0.6 mL of N,N-dimethylformamide. The solution was purged with argon three times, and cooled to 0-5° C. under an ice-water bath. 4g (21.2 mg, 44.8 μmol) in 0.3 mL of N,N-dimethylformamide and 4-(4,6-dimethoxy-1,3,5-triazin-2-yl)-4-methylmorpholinium chloride (18.5 mg, 67.3 μmol) were added, and the reaction solution was stirred under an ice bath for 10 minutes. The ice bath was removed, and the reaction solution was warmed up to room temperature and stirred for 1 hour to obtain compound 5. The reaction solution was purified by high performance liquid chromatography (separation conditions: column: XBridge Prep C18 OBD 5 μm 19*250 mm; mobile phase: A-water (10 mmol $NH_4OAc$), B-acetonitrile, gradient elution, flow rate: 18 mL/min). The corresponding fractions were collected, and concentrated under reduced pressure to obtain the title products (2.4 mg, 1.7 mg).

MS m/z (ESI): 1074.4 [M+1].

Compound 5-A with Single Configuration (Having Shorter Retention Time):

UPLC analysis: retention time: 1.14 minutes, purity: 85% (column: ACQUITY UPLC BEHC18 1.7 μm 2.1*50 mm, mobile phase: A-water (5 mmol $NH_4OAc$), B-acetonitrile).

$^1$H NMR (400 MHz, DMSO-$d_6$): δ 8.60 (t, 1H), 8.51-8.49 (d, 1H), 8.32-8.24 (m, 1H), 8.13-8.02 (m, 2H), 8.02-7.96 (m, 1H), 7.82-7.75 (m, 1H), 7.31 (s, 1H), 7.26-7.15 (m, 4H), 6.99 (s, 1H), 6.55-6.48 (m, 1H), 5.65-5.54 (m, 1H), 5.41 (s, 2H), 5.35-5.15 (m, 3H), 4.74-4.62 (m, 2H), 4.54-4.40 (m, 2H), 3.76-3.64 (m, 4H), 3.62-3.48 (m, 2H), 3.20-3.07 (m, 2H), 3.04-2.94 (m, 2H), 2.80-2.62 (m, 2H), 2.45-2.30 (m, 3H), 2.25-2.15 (m, 2H), 2.15-2.04 (m, 2H), 1.93-1.78 (m, 2H), 1.52-1.39 (m, 3H), 1.34-1.12 (m, 5H), 0.87 (t, 3H), 0.64-0.38 (m, 4H).

Compound 5-B with Single Configuration (Having Longer Retention Time):

UPLC$^{analysis}$: retention time: 1.16 minutes, purity: 89% (column: ACQUITY UPLC BEHC18 1.7 μm 2.1*50 mm, mobile phase: A-water (5 mmol NH$_4$OAc), B-acetonitrile).

$^1$H NMR (400 MHz, DMSO-d$_6$): δ 8.68-8.60 (m, 1H), 8.58-8.50 (m, 1H), 8.32-8.24 (m, 1H), 8.13-8.02 (m, 2H), 8.02-7.94 (m, 1H), 7.82-7.75 (m, 1H), 7.31 (s, 1H), 7.26-7.13 (m, 4H), 6.99 (s, 1H), 6.55-6.48 (m, 1H), 5.60-5.50 (m, 1H), 5.41 (s, 2H), 5.35-5.15 (m, 3H), 4.78-4.68 (m, 1H), 4.60-4.40 (m, 2H), 3.76-3.58 (m, 4H), 3.58-3.48 (m, 1H), 3.20-3.10 (m, 2H), 3.08-2.97 (m, 2H), 2.80-2.72 (m, 2H), 2.45-2.30 (m, 3H), 2.25-2.13 (m, 2H), 2.13-2.04 (m, 2H), 2.03-1.94 (m, 2H), 1.91-1.78 (m, 2H), 1.52-1.39 (m, 3H), 1.34-1.12 (m, 5H), 0.91-0.79 (m, 3H), 0.53-0.34 (m, 4H).

Example 6

N-((2S,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 6-A N-((2S,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 6-B

6-A

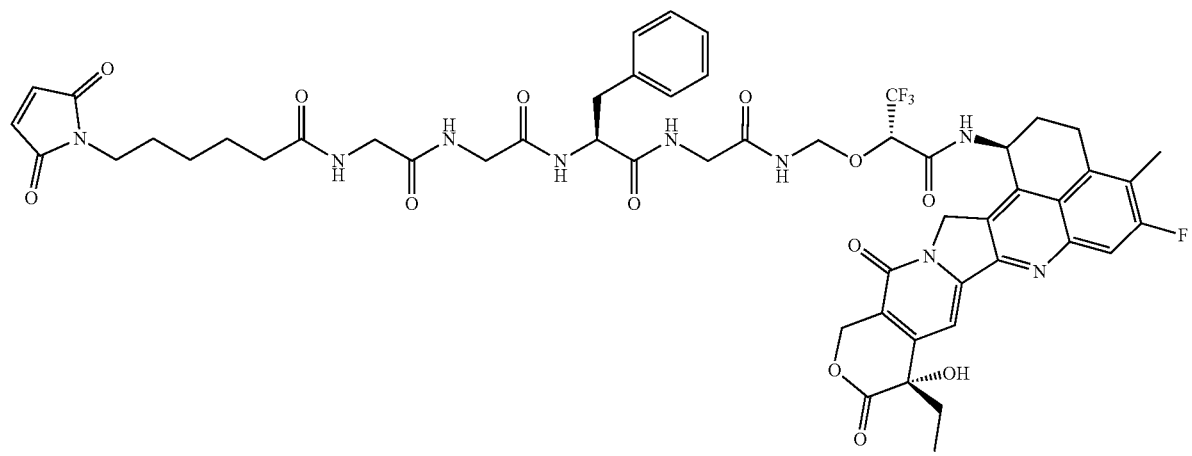

6-B

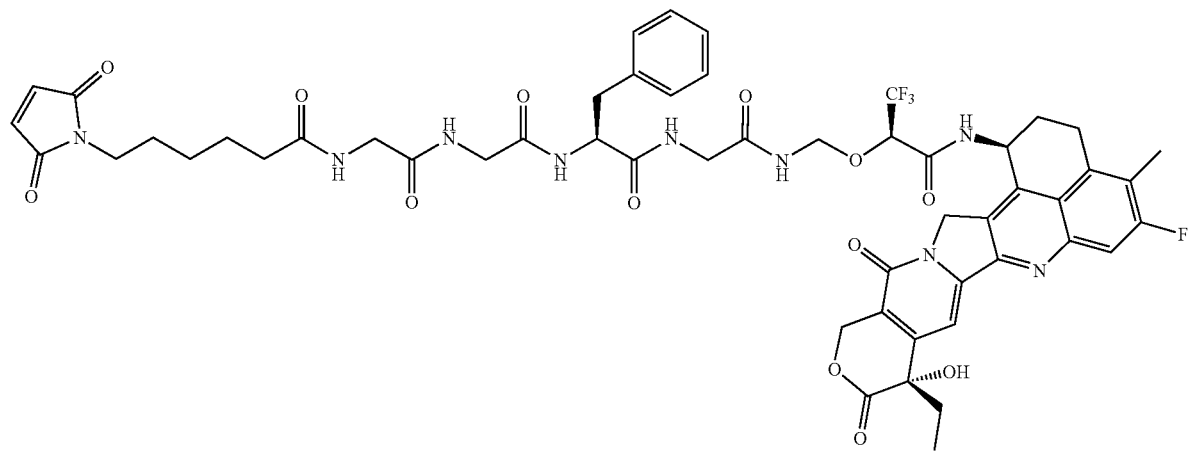

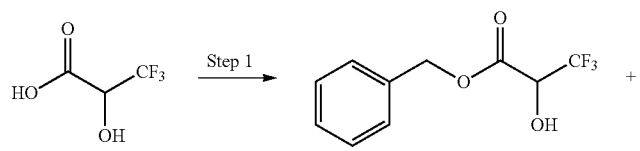

3a            6a

-continued
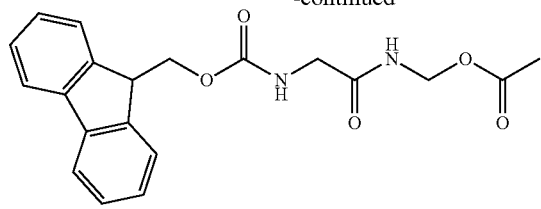
4b
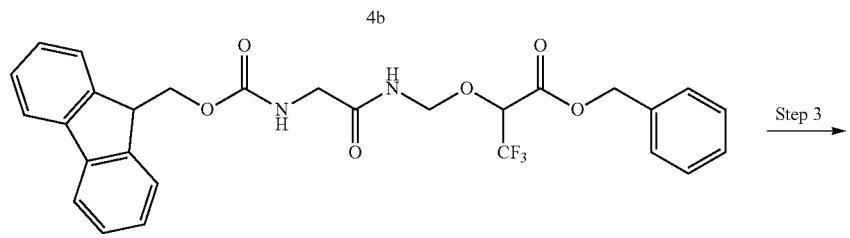
6b
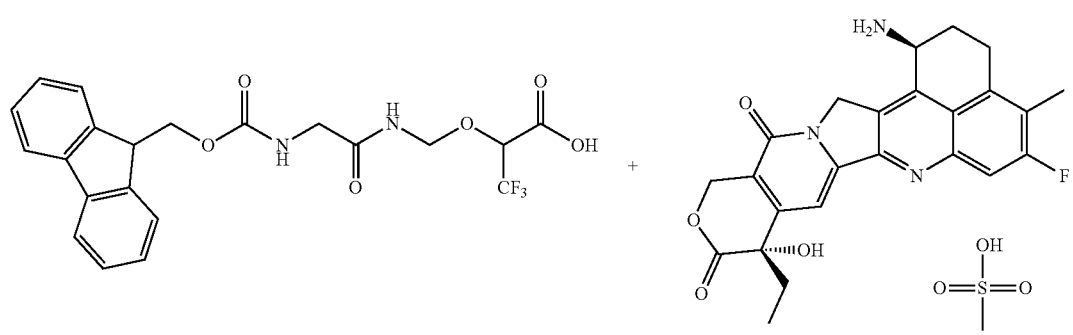
6c        1b
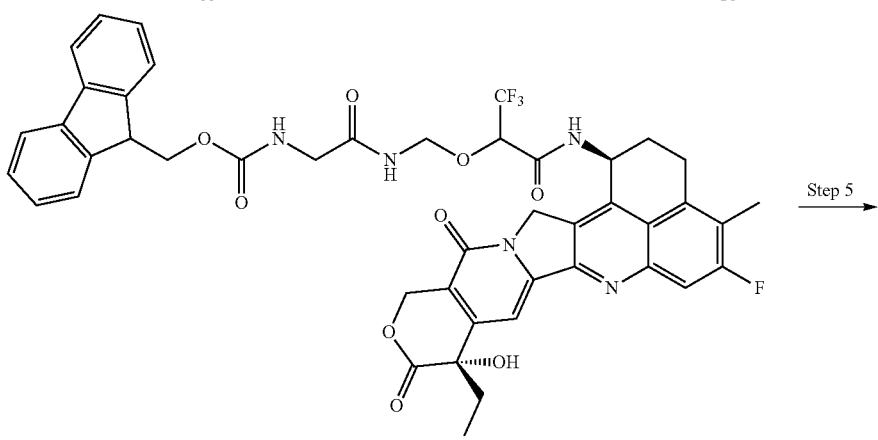
6d
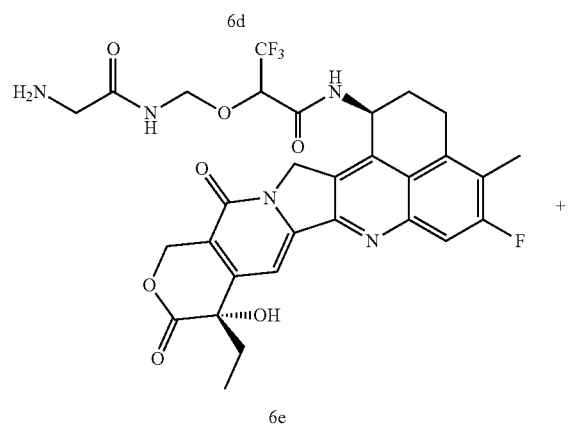
6e

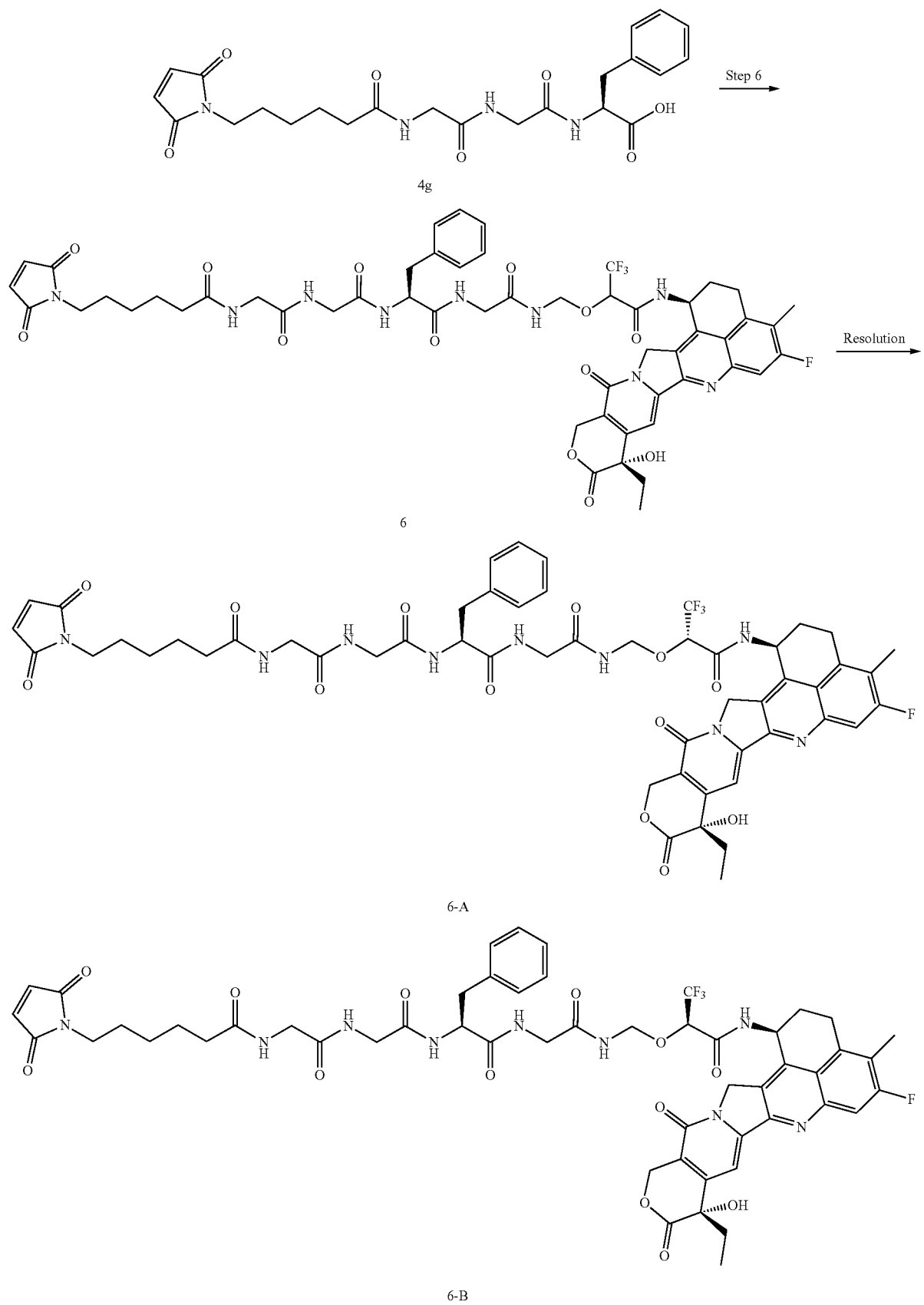

Step 1

Benzyl 3,3,3-trifluoro-2-hydroxypropanoate 6a 3a (1.80 g, 12.5 mmol) was dissolved in 100 mL of acetonitrile, and then added with potassium carbonate (5.17 g, 37.5 mmol), benzyl bromide (4.48 mL, 37.5 mmol) and tetrabutylammonium iodide (231 mg, 0.63 mmol) successively. The reaction solution was heated to 60° C. and stirred for 5 hours. The reaction solution was cooled to room temperature and filtered. The filtrate was concentrated under reduced pressure, and the resulting residues were purified by silica gel column chromatography with developing solvent system C to obtain the title product 6a (980 mg, yield: 33.5%).

$^1$H NMR (400 MHz, CDCl$_3$): δ 7.43-7.36 (m, 5H), 5.34 (s, 2H), 4.53 (s, 1H), 3.44 (s, 1H).

Step 2

Benzyl 1-(9H-fluoren-9-yl)-3,6-dioxo-10-(trifluoromethyl)-2,9-dioxa-4,7-diazaundecan-11-oate 6b 4b (63 mg, 0.17 mmol) and 6a (80 mg, 0.34 mmol) were added to a reaction flask, followed by the addition of 3 mL of tetrahydrofuran. The reaction solution was purged with argon three times and cooled to 0-5° C. under an ice-water bath. Potassium tert-butoxide (38 mg, 0.34 mmol) was added and the ice-water bath was removed. The reaction solution was warmed up to room temperature and stirred for 20 minutes. 10 mL ice water was added to the reaction solution, which was then extracted with ethyl acetate (20 mL×2) and chloroform (10 mL×5). The organic phases were combined and concentrated, and the resulting residues were dissolved in 2 mL of dioxane. 0.4 mL of water, sodium bicarbonate (19 mg, 0.23 mmol) and 9-fluorene methyl chloroformate (49 mg, 0.19 mmol) were added, and the reaction solution was stirred at room temperature for 1 hour. 20 mL of water was added, and the reaction solution was extracted with ethyl acetate (10 mL×3). The organic phase was washed with saturated sodium chloride solution (20 mL), dried over anhydrous sodium sulfate and filtered. The filtrate was concentrated under reduced pressure. The resulting residues were purified by silica gel column chromatography with developing solvent system C to obtain the title product 6b (51 mg, yield: 55.3%).

MS m/z (ESI): 559.9 [M+18].

Step 3

1-(9H-Fluoren-9-yl)-3,6-dioxo-10-(trifluoromethyl)-2,9-dioxa-4,7-diazaundecan-11-oic acid 6c 6b (15 mg, 0.28 mmol) was dissolved in 3 mL of a mixed solvent of tetrahydrofuran and ethyl acetate (V:V=2:1), followed by the addition of palladium on carbon (15 mg, content: 10%). The reaction solution was purged with hydrogen three times and stirred at room temperature for 1 hour. The reaction solution was filtered through celite, and the filter cake was rinsed with tetrahydrofuran. The filtrate was concentrated to obtain the crude title product 6c (13 mg).

MS m/z (ESI): 452.9 [M+1].

Step 4

(9H-Fluoren-9-yl)methyl (2-((((3-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,1,1-trifluoro-3-oxopropan-2-yl)oxy)methyl)amino)-2-oxoethyl)carbamate 6d 1b (10 mg, 18.8 μmol) was added to a reaction flask, followed by the addition of 1 mL of N,N-dimethylformamide. The solution was purged with argon three times, and cooled to 0-5° C. under an ice-water bath. One drop of triethylamine, 6c (13 mg, 28.7 μmol) in 0.5 mL of N,N-dimethylformamide, and 4-(4,6-dimethoxy-1,3,5-triazin-2-yl)-4-methylmorpholinium chloride (11 mg, 39.7 μmol) were added, and the reaction solution was stirred under an ice bath for 30 minutes. 10 mL of water was added, and the reaction solution was extracted with ethyl acetate (10 mL×3). The organic phase were combined, washed with saturated sodium chloride solution (10 mL×2), dried over anhydrous sodium sulfate and filtered. The filtrate was concentrated under reduced pressure, and the resulting residues were purified by thin layer chromatography with developing solvent system B to obtain the title product 6d (16 mg, yield: 97.8%).

MS m/z (ESI): 870.0[M+1].

Step 5

2-((2-Aminoacetamido)methoxy)-N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)-3,3,3-trifluoropropanamide 6e 6d (16 mg, 18.4 μmol) was dissolved in 0.6 mL of dichloromethane, followed by the addition of 0.3 mL of diethylamine. The reaction solution was stirred at room temperature for 2 hours. The reaction solution was concentrated under reduced pressure. 2 mL of toluene was added and the solution was concentrated under reduced pressure, which was repeated twice. 3 mL of n-hexane was added to the residues to pulp, and the supernatant was poured out after standing for a while to retain the solid, which was repeated three times. The solid residues were concentrated under reduced pressure by an oil pump until dryness to obtain the crude title product 6e (12 mg), which was used directly in the next step without purification.

MS m/z (ESI): 647.9 [M+1].

Step 6

N-((2S,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 6-A N-((2R,10S)-10-Benzyl-2-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)carbamoyl)-1,1,1-trifluoro-6,9,12,15-tetraoxo-3-oxa-5,8,11,14-tetraazahexadecan-16-yl)-6-(2,5-dioxo-2,5-dihydro-1H-pyrrol-1-yl)hexanamide 6-B The crude compound 6e (12 mg, 18.5 μmol) was dissolved in 1.0 mL of N,N-dimethylformamide. The solution was purged with argon three times, and cooled to 0-5° C. under an ice-water bath. 4g (14 mg, 29.6 μmol) in 0.3 mL of N,N-dimethylformamide, and 4-(4,6-dimethoxy-1,3,5-triazin-2-yl)-4-methylmorpholinium chloride (15 mg, 54.2 μmol) were added, and the reaction solution was stirred under an ice bath for 30 minutes. The ice bath was removed, and the reaction solution was warmed up to room temperature and stirred for 1 hour to obtain compound 6. The reaction solution was purified by high performance liquid chromatography (separation conditions: column: XBridge Prep C18 OBD 5 μm 19*250 mm; mobile phase: A-water (10 mmol NH$_4$OAc), B-acetonitrile, gradient elution, flow rate: 18 mL/min). The corresponding fractions were collected, and concentrated under reduced pressure to obtain the title products (2.7 mg, 2.6 mg).

MS m/z (ESI): 1102.0 [M+1].

Compound with Single Configuration (Having Shorter Retention Time):

UPLC analysis: retention time: 1.18 minutes, purity: 91% (column: ACQUITY UPLC BEHC18 1.7 μm 2.1*50 mm, mobile phase: A-water (5 mmol NH$_4$OAc), B-acetonitrile).

$^1$H NMR (400 MHz, DMSO-d$_6$): δ 8.97 (d, 1H), 8.85-8.76 (m, 1H), 8.37-8.27 (m, 1H), 8.12-8.02 (m, 1H), 8.02-7.95 (m, 1H), 7.80 (d, 1H), 7.31 (s, 1H), 7.26-7.10 (m, 4H), 6.99 (s, 1H), 6.66 (s, 1H), 6.52 (s, 1H), 5.65-5.54 (m, 1H), 5.41 (s, 1H), 5.37-5.25 (m, 3H), 5.23-5.13 (m, 1H), 4.81-4.68 (m, 2H), 4.51-4.41 (m, 1H), 3.78-3.45 (m, 6H), 3.21-3.13 (m, 1H), 3.02-2.93 (m, 1H), 2.77-2.63 (m, 2H), 2.45-2.29 (m, 3H), 2.24-2.05 (m, 3H), 2.04-1.93 (m, 5H), 1.90-1.75 (m, 2H), 1.52-1.38 (m, 4H), 0.90-0.78 (m, 5H).

Compound with Single Configuration (Having Longer Retention Time):

UPLC analysis: retention time: 1.23 minutes, purity: 90% (column: ACQUITY UPLC BEHC18 1.7 μm 2.1*50 mm, mobile phase: A-water (5 mmol NH$_4$OAc), B-acetonitrile).

$^1$H NMR (400 MHz, DMSO-d$_6$): δ 9.05 (d, 1H), 8.97-8.88 (m, 1H), 8.35-8.27 (m, 1H), 8.11-8.03 (m, 1H), 8.02-7.95 (m, 1H), 7.80 (d, 1H), 7.34 (s, 1H), 7.29-7.13 (m, 4H), 6.99 (s, 1H), 6.66 (s, 1H), 6.54 (s, 1H), 5.64-5.55 (m, 1H), 5.43 (s, 1H), 5.36-5.20 (m, 3H), 4.92-4.85 (m, 1H), 4.82-4.72 (m, 2H), 4.52-4.42 (m, 1H), 3.77-3.48 (m, 6H), 3.21-3.14 (m, 1H), 3.03-2.95 (m, 1H), 2.79-2.65 (m, 2H), 2.47-2.28 (m, 3H), 2.25-2.05 (m, 3H), 2.05-1.94 (m, 5H), 1.91-1.76 (m, 2H), 1.52-1.37 (m, 4H), 0.92-0.77 (m, 5H).

Example 7 Preparation of Related Antibodies and Detection Proteins Thereof

Example 7-1. B7H3 Antigen and Detection Protein

The human B7H3 sequence represented by SEQ ID NO: 1 was used as the template for B7H3 of the present disclosure, and the amino acid sequence of the antigen and detection protein involved in the present disclosure were designed. Unless otherwise specified, the following B7H3 antigen is human B7H3.

1.1 Human B7H3 Full-Length Amino Acid Sequence: B7H3 (SEQ ID NO: 1):

MLRRRGSPGMGVHVGAALGALWFCLTGALEVQVPEDPVVALVGTDATLCCSFSPEPGFSL

AQLNLIWQLTDTKQLVHSFAEGQDQGSAYANRTALFPDLLAQGNASLRLQRVRVADEGSFT

CFVSIRDFGSAAVSLQVAAPYSKPSMTLEPNKDLRPGDTVTITCSSYQGYPEAEVFWQDGQ

GVPLTGNVTTSQMANEQGLFDVHSILRVVLGANGTYSCLVRNPVLQQDAHSSVTITPQRSP

TGAVEVQVPEDPVVALVGTDATLRCSFSPEPGFSLAQLNLIWQLTDTKQLVHSFTEGRDQGS

AYANRTALFPDLLAQGNASLRLQRVRVADEGSFTCFVSIRDFGSAAVSLQVAAPYSKPSMTL

EPNKDLRPGDTVTITCSSYRGYPEAEVFWQDGQGVPLTGNVTTSQMANEQGLFDVHSVLR

VVLGANGTYSCLVRNPVLQQDAHGSVTITGQPMTFPPEALWVTVGLSVCLIALLVALAFVC

WRKIKQSCEEENAGAEDQDGEGEGSKTALQPLKHSDSKEDDGQEIA

Note:
The double-underlined portion is the signal peptide (Signal peptide: 1-28);
The underlined portion is the B7H3 extracellular domain (Extracellular domain: 29-466),
wherein 29-139 is Ig-like V-type 1 domain, and 145-238 is Ig-like C2-type 1 domain; 243-357 is Ig-like V-type 2 domain, and 363-456 is Ig-like C2-type 2 domain;
The dot-lined portion is the transmembrane domain portion (Transmembrane domain: 467-487);
The italic portion is the intracellular domain (Cytoplasmic domain: 488-534).

1.2 Mouse B7H3 Full-Length Amino Acid Sequence (SEQ ID NO: 2)

MLRGWGGPSVGVCVRTALGVLCLCLTGAVEVQVSEDPVVALVDTDATLRCSFSPEPGFSL

AQLNLIWQLTDTKQLVHSFTEGRDQGSAYSNRTALFPDLLVQGNASLRLQRVRVTDEGSY

TCFVSIQDFDSAAVSLQVAAPYSKPSMTLEPNKDLRPGNMVTITCSSYQGYPEAEVFWKDG

QGVPLTGNVTTSQMANERGLFDVHSVLRVVLGANGTYSCLVRNPVLQQDAHGSVTITGQP

LTFPPEALWVTVGLSVCLVVLLVALAFV CWRKIKQSCEEENAGAEDQDGDGEGSKTALRPLK

PSENKEDDGQEIA

Note:
The double-underlined portion is the signal peptide (Signal peptide: 1-28);
The underlined portion is the B7H3 extracellular domain (Extracellular domain: 29-248),
wherein 29-139 is Ig-like V-type domain, and 145-238 is Ig-like C2-type domain;
The dot-lined portion is the transmembrane domain portion (Transmembrane domain: 249-269);
The italic portion is the intracellular domain (Cytoplasmic domain: 270-316).

1.3 Human B7H3 Antigen for Screening and Detection (SEQ ID NO: 3)

It is a commercial product (R&D cat #1949-B3-050/CF, abbreviated as 2Ig-B7H3), and the sequence is as follows:

LEVQVPEDPVVALVGTDATLCCSFSPEPGFSLAQLNLIWQLTDTKQLVHS

FAEGQDQGSAYANRTALFPDLLAQGNASLRLQRVRVADEGSFTCFVSIRD

FGSAAVSLQVAAPYSKPSMTLEPNKDLRPGDTVTITCSSYQGYPEAEVFW

QDGQGVPLTGNVTTSQMANEQGLFDVHSILRVVLGANGTYSCLVRNPVLQ

QDAHSSVTITPQRSPTG-HHHHHH

Note:
The underlined portion is the B7H3 extracellular region;

The italic portion is the His-tag marker.

1.4 Human B7H3 Antigen for Detection (SEQ ID NO: 4)

It is a commercial product (SinoBiological cat #11188-H08H, abbreviated as 4Ig-B7H3), and the sequence is as follows:

LEVQVPEDPVVALVGTDATLCCSFSPEPGFSLAQLNLIWQLTDTKQLVHS

FAEGQDQGSAYANRTALFPDLLAQGNASLRLQRVRVADEGSFTCFVSIRD

FGSAAVSLQVAAPYSKPSMTLEPNKDLRPGDTVTITCSSYQGYPEAEVFW

QDGQGVPLTGNVTTSQMANEQGLFDVHSILRVVLGANGTYSCLVRNPVLQ

QDAHSSVTITPQRSPTGAVEVQVPEDPVVALVGTDATLRCSFSPEPGFSL

AQLNLIWQLTDTKQLVHSFTEGRDQGSAYANRTALFPDLLAQGNASLRLQ

RVRVADEGSFTCFVSIRDFGSAAVSLQVAAPYSKPSMTLEPNKDLRPGDT

VTITCSSYRGYPEAEVFWQDGQGVPLTGNVTTSQMANEQGLFDVHSVLRV

VLGANGTYSCLVRNPVLQQDAHGSVTITGQPMT-HHHHHH

Note:
The underlined portion is the B7H3 extracellular region;

The italic portion is the His-tag marker.

1.5 Mouse B7H3 Antigen for Screening and Detection (SEQ ID NO: 5)

It is a commercial product (R&D cat #1397-B3-050/CF), and the sequence is as follows:

VEVQVSEDPVVALVDTDATLRCSFSPEPGFSLAQLNLIWQLTDTKQLVHS

FTEGRDQGSAYSNRTALFPDLLVQGNASLRLQRVRVTDEGSYTCFVSIQD

FDSAAVSLQVAAPYSKPSMTLEPNKDLRPGNMVTITCSSYQGYPEAEVFW

KDGQGVPLTGNVTTSQMANERGLFDVHSVLRVVLGANGTYSCLVRNPVLQ

QDAHGSVTITGQPLTF-HHHHHH

Note:
The underlined portion is the B7H3 extracellular region;

The italic portion is the His-tag marker.

Example 7-2. Preparation of Fully Humanized Antibody 2.1 Screening of Positive Sequence B cells were isolated from human PBMC, spleen and lymph node tissues, and RNA was extracted to construct naive single chain phage antibody library (capacity 3.2× $10^{10}$). The constructed naive single chain phage library was packaged to form phage particles, and then subjected to panning by liquid phase method. The phage was bound to the biotinylated B7H3 in liquid phase, and then separated by streptavidin magnetic beads. In order to obtain positive sequences that can cross-bind to human B7H3 (R&D cat #1949-B3-050/CF) and mouse B7H3 (R&D cat #1397-B3-050/CF) respectively, biotinylated human B7H3 and biotinylated mouse B7H3 were used for alternate panning separately. 2 µg/ml of biotinylated human B7H3 was used in the first round of panning. 2 µg/ml of biotinylated mouse B7H3 was used in the second round of panning. 0.5 µg/ml of biotinylated human B7H3 was used in the third round of panning. After three rounds of panning, 500 monoclones were picked and packaged into phage for phage ELISA testing. The binding activity of monoclonal phage to human B7H3 (R&D cat #1949-B3-050/CF) and mouse B7H3 (R&D cat #1397-B3-050/CF) were tested separately. ELISA plate was coated with 1 µg/ml of human B7H3 or murine B7H3, and added with phage supernatant diluted at 1:1 with blocking buffer, and then detected with anti-M13 HRP. The clones with ELISA OD450 value of greater than 0.5, and with ratios of ELISA OD450 values for binding to human or mouse B7H3 to ELISA OD450 values for binding to 1% BSA greater than 2.0 were sequenced and the specific sequence 1702 was obtained (also called h1702 in the present disclosure, the antibodies h1702 and h1702DS referred to in the present disclosure are the same as h1702 and h1702-1 of the patent application PCT/CN2018/081249, all the contents of the patent application PCT/CN2018/081249 are incorporated into the present disclosure).

2.2 Construction of Intact Monoclonal Antibody

The specific sequence 1702 was obtained by phage library screening, and the process for constructing the intact monoclonal antibody thereof was as follows.

Based on the single chain antibody sequence obtained by sequencing, primers were designed to construct the VH/VK/VL gene fragment of each single chain antibody sequence by PCR. The heavy chain variable region of 1702 was obtained.

```
                                            SEQ ID NO: 6
>heavy chain variable sequence of 1702
QVQLVQSGGGVVQPGTSLRLSCAASGFIFSSSAMHWVRQAPGKGLEWVAV

ISYDGSNKYYVDSVKGRFTISRDNSKNTLYLQMNSLRAEDTAVYYCARSA

RLYASFDYWGQGALVTVSS

SEQ ID NO: 7
>light chain variable sequence of 1702
QTVVTQEPSFSVSPGGTVTLTCGLSSGSVSTSHYPSWYQQTPGQAPRAIL

IYNTNTRSSGVPDRFSGSILGNKAALTITGAQADDESDYYCAIHVDRDIW

VFGGGTKLTVL

Note:
The order is FR1-CDR1-FR2-CDR2-FR3-CDR3-FR4. The italics portions in sequence are FR sequences, and the underlined portions are the CDR sequences.
```

The CDR sequences in the light chain and heavy chain of each antibody are shown in Table 1.

TABLE 1

CDR region sequences of each heavy and light chain

| Antibody | | Heavy chain | | Light chain |
|---|---|---|---|---|
| 1702 | HCDR1 | GFIFSSSA SEQ ID NO: 8 | LCDR1 | SGSVSTSHY SEQ ID NO: 11 |
| | HCDR2 | ISYDGSNK SEQ ID NO: 9 | LCDR2 | NTN SEQ ID NO: 12 |
| | HCDR3 | ARSARLYASFDY SEQ ID NO: 10 | LCDR3 | AIHVDRDIWV SEQ ID NO: 13 |

The antibody variable region was then homologously recombined with the constant region gene (CH1-FC/CL) fragment to construct the intact antibody VH-CH1-FC/VK-CL/VL-CL.

The constructed intact full-length antibody 1702 sequence is as follows.

```
Heavy chain (IgG1) amino acid sequence of 1702:
                                         (SEQ ID NO: 14)
QVQLVQSGGGVVQPGTSLRLSCAASGFIFSSSAMHWVRQAPGKGLEWVAV

ISYDGSNKYYVDSVKGRFTISRDNSKNTLYLQMNSLRAEDTAVYYCARSA

RLYASFDYWGQGALVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK

Light chain amino acid sequence of 1702: Lamada
                                         (SEQ ID NO: 15)
QTVVTQEPSFSVSPGGTVTLTCGLSSGSVSTSHYPSWYQQTPGQAPRMLI

YNTNTRSSGVPDRFSGSILGNKAALTITGAQADDESDYYCAIHVDRDIWV

FGGGTKLTVLGQPKANPTVTLFPPSSEELQANKATLVCLISDFYPGAVTV

AWKADGSPVKAGVETTKPSKQSNNKYAASSYLSLTPEQWKSHRSYSCQVT

HEGSTVEKTVAPTECS
```

In order to further improve the stability of the antibody, the amino acids of the light chain sequence of 1702 were mutated. Specific mutation involves that the first amino acid residue Q at N-terminus of the light chain (SEQ ID NO: 15) was replaced by D, the first amino acid residue S at C-terminus was deleted, so as to obtain a more stable and uniform monoclonal antibody 1702DS (also called h1702DS in the present disclosure).

The heavy chain sequence of 1702DS after mutation modification is SEQ ID NO: 14, and the light chain amino acid sequence is as follows: (SEQ ID NO: 16).

```
DTVVTQEPSFSVSPGGTVTLTCGLSSGSVSTSHYPSWYQQTPGQAPRMLI

YNTNTRSSGVPDRFSGSILGNKAALTITGAQADDESDYYCAIHVDRDIWV

FGGGTKLTVLGQPKANPTVTLEPPSSEELQANKATLVCLISDFYPGAVTV

AWKADGSPVKAGVETTKPSKQSNNKYAASSYLSLTPEQWKSHRSYSCQVT

HEGSTVEKTVAPTEC
```

2.3 Expression and Purification of Fully Humanized Antibody

The plasmids expressing the light and heavy chain of the antibody respectively were transfected into HEK293E cells at a ratio of 1.5:1. The supernatant was collected after 6 days, and the debris was removed by high-speed centrifugation, and purification was performed by a Protein A column. The column was rinsed with PBS until the A280 reading dropped to the baseline. The target protein was eluted with an acidic eluent of pH 3.0-pH 3.5, and neutralized with 1 M Tris-HCl (pH 8.0-9.0). The eluted sample was appropriately concentrated and further purified by gel chromatography Superdex200 (GE) which had been equilibrated by PBS to remove the aggregate. The monomer peak was collected and packed for later use.

Preparation Examples of B7H3 Antibody-Drug Conjugate

Example 8 ADC-1

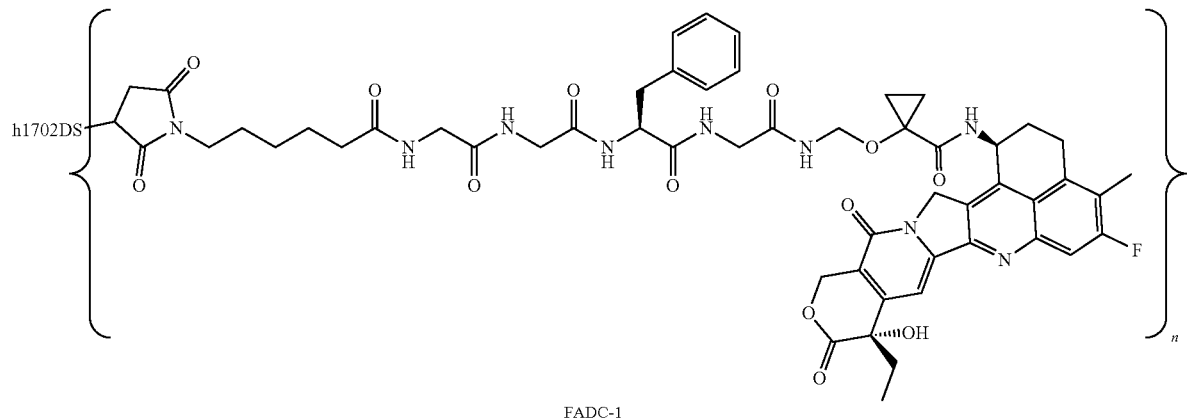

FADC-1

A formulated aqueous solution of tris(2-carboxyethyl) phosphine (10 mM, 0.347 mL, 3.47 μmol) was added to a PBS-buffered aqueous solution of antibody 1702DS (0.05 M PBS-buffered aqueous solution with pH=6.5; 7.3 ml, 13.8 mg/ml, 0.681 μmol) at 37° C. The reaction solution was placed in a water bath shaker, and shaked at 37° C. for 3 hours before stopping the reaction. The reaction solution was cooled to 25° C. in a water bath, and diluted to 14.0 ml. 3.3 ml of the solution was taken for the next reaction.

Compound 4 (3.0 mg, 2.75 μmol) was dissolved in 0.15 mL of DMSO, and then added to 3.3 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-1 of formula FADC-1 (1.35 mg/mL, 13 mL), which was stored at 4° C.

The average value calculated by UV-HPLC: n=7.50.

Example 9 ADC-2

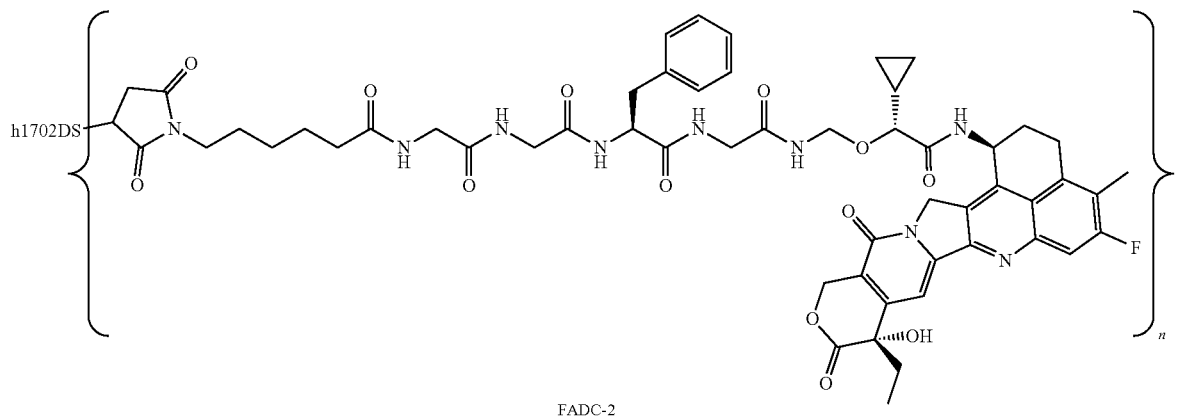

FADC-2

A formulated aqueous solution of tris(2-carboxyethyl)phosphine (10 mM, 0.050 mL, 0.50 μmol) was added to a PBS-buffered aqueous solution of antibody 1702DS (0.05 M PBS-buffered aqueous solution with pH=6.5; 1.0 ml, 13.8 mg/ml, 0.093 μmol) at 37° C. The reaction solution was placed in a water bath shaker, and shaked at 37° C. for 3 hours before stopping the reaction. The reaction solution was cooled to 25° C. in a water bath, and diluted to 2.0 ml. 1.15 ml of the solution was taken for the next reaction.

Compound 5-having shorter retention time, the compound 5-A (1.29 mg, 1.02 μmol) was dissolved in 0.10 mL of DMSO, and then added to 1.15 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-2 of formula FADC-2 (2.63 mg/mL, 2.4 mL), which was stored at 4° C.

The average value calculated by UV-HPLC: n=7.24.

Example 10 ADC-3

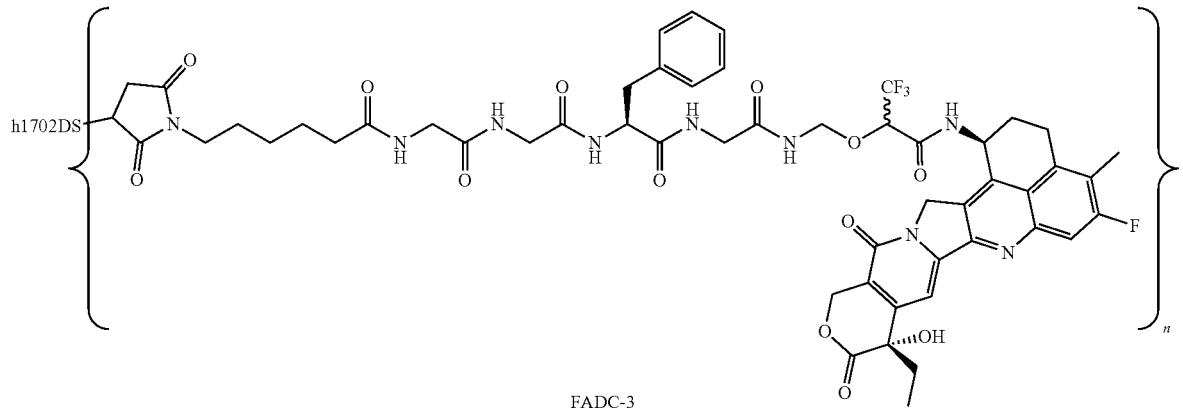

FADC-3

A formulated aqueous solution of tris(2-carboxyethyl)phosphine (10 mM, 0.347 mL, 3.47 μmol) was added to a PBS-buffered aqueous solution of antibody 1702DS (0.05 M PBS-buffered aqueous solution with pH=6.5; 7.3 ml, 13.8 mg/mi, 0.681 μmol) at 37° C. The reaction solution was placed in a water bath shaker, and shaked at 37° C. for 3 hours before stopping the reaction. The reaction solution was cooled to 25° C. in a water bath, and diluted to 14.0 ml. 3.3 ml of the solution was taken for the next reaction.

Compound 6—the compound having longer retention time (3.0 mg, 2.75 μmol) was dissolved in 0.15 mL of DMSO, and then added to 3.3 ml of the above solution. The reaction solution was placed in a water bath shaker, and shaked at 25° C. for 3 hours before stopping the reaction. The reaction solution was desalted and purified with a Sephadex G25 gel column (elution phase: 0.05 M PBS-buffered aqueous solution with pH=6.5, containing 0.001 M EDTA) to obtain the PBS-buffered solution of the exemplary product ADC-3 of formula FADC-3 (1.28 mg/mL, 13 mL), which was stored at 4° C.

The average value calculated by UV-HPLC: n=7.58.

Example 11 ADC-4

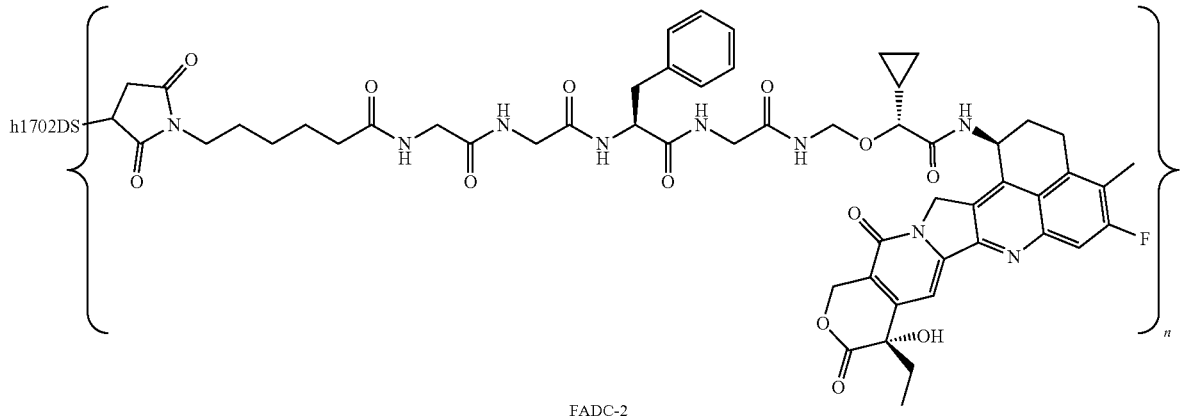

FADC-2

A formulated aqueous solution of tris(2-carboxyethyl) phosphine (TCEP) (10 mM, 73.7 μL, 740 nmol) was added to a PBS-buffered aqueous solution of antibody 1702DS (0.05 M PBS-buffered aqueous solution with pH=6.5; 10.0 mg/ml, 2.14 mL, 144.60 nmol) at 37° C. The reaction solution was placed in a water bath shaker, and shaked at 37° C. for 3 hours before stopping the reaction. The reaction solution was cooled to 25° C. in a water bath.

Compound 5-having shorter retention time, the compound 5-A (3.0 mg, 2793 nmol) was dissolved in 150 μl of DMSO, and then added to the above solution. The reaction solution was placed in a water bath shaker, and shaked at 25° C. for 3 hours before stopping the reaction. The reaction solution was desalted and purified with a Sephadex G25 gel column (elution phase: 0.05M PBS-buffered aqueous solution with pH=6.5, containing 0.001 M EDTA) to obtain the PBS-buffered solution of the exemplary product ADC-4 of formula FADC-2 (1.28 mg/mL, 13.0 mL), which was stored at 4° C.

The average value calculated by UV-Vis: n=6.87.

Example 12 ADC-5

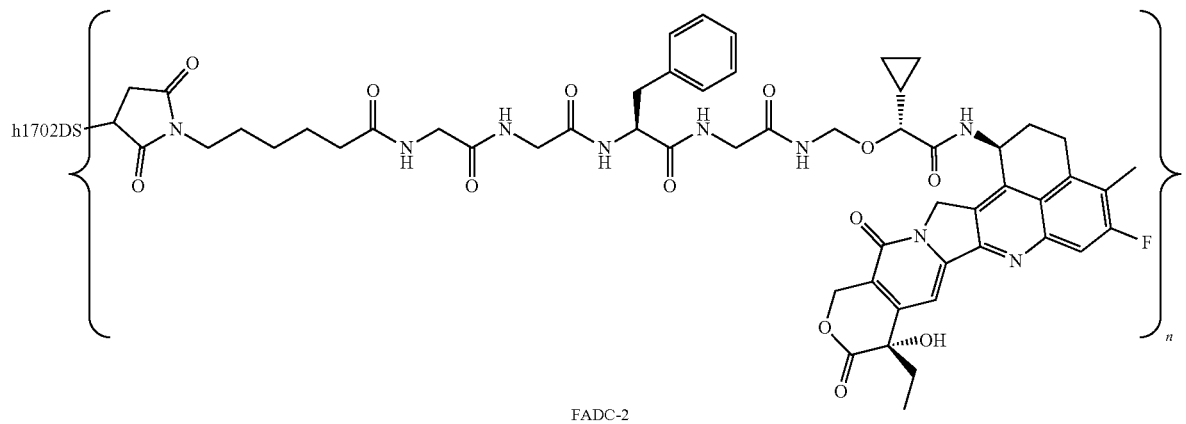

FADC-2

A formulated aqueous solution of tris(2-carboxyethyl) phosphine (TCEP) (10 mM, 30.1 μL, 300 nmol) was added to a PBS-buffered aqueous solution of antibody 1702DS (0.05 M PBS-buffered aqueous solution with pH=6.5; 10.0 mg/ml, 0.89 mL, 60.14 nmol) at 37° C. The reaction solution was placed in a water bath shaker, and shaked at 37° C. for 3 hours before stopping the reaction. The reaction solution was cooled to 25° C. in a water bath.

Compound 5-having shorter retention time, the compound 5-A (1.02 mg, 950 nmol) was dissolved in 100 μl of DMSO, and then added to the above solution. The reaction solution was placed in a water bath shaker, and shaked at 25° C. for 3 hours before stopping the reaction. The reaction solution was desalted and purified with a Sephadex G25 gel column (elution phase: 0.05M PBS-buffered aqueous solution with pH=6.5, containing 0.001 M EDTA) to obtain the PBS-buffered solution of the exemplary product ADC-5 of formula FADC-2 (1.94 mg/mL, 3.5 mL), which was stored at 4° C.

The average value calculated by UV-Vis: n=6.11.

According to the above reaction procedures and conventional technical means in the field, the reaction conditions were adjusted to obtain exemplary products of formula FADC-2 with n values of 2.97 and 4.8 respectively: ADC-6 (n=2.97); ADC-7 (n=4.8).

Example 13 ADC-8

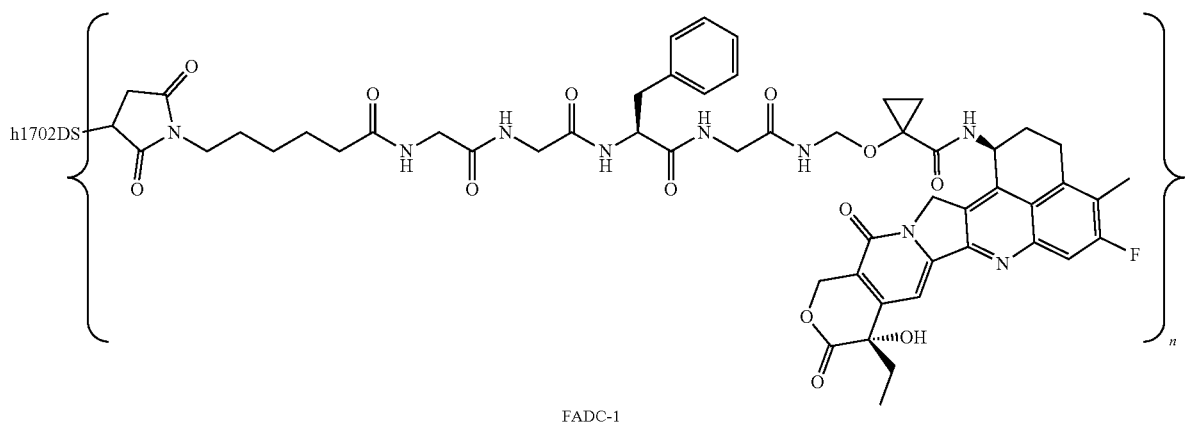

FADC-1

A formulated aqueous solution of tris(2-carboxyethyl) phosphine (TCEP) (10 mM, 30.1 μL, 300 nmol) was added to a PBS-buffered aqueous solution of antibody 1702DS (0.05 M PBS-buffered aqueous solution with pH=6.5; 10.0 mg/ml, 0.89 mL, 60.14 nmol) at 37° C. The reaction solution was placed in a water bath shaker, and shaked at 37° C. for 3 hours before stopping the reaction. The reaction solution was cooled to 25° C. in a water bath.

Compound 4 (1.0 mg, 943 nmol) was dissolved in 100 μl of DMSO, and then added to the above solution. The reaction solution was placed in a water bath shaker, and shaked at 25° C. for 3 hours before stopping the reaction. The reaction solution was desalted and purified with a Sephadex G25 gel column (elution phase: 0.05M PBS-buffered aqueous solution with pH=6.5, containing 0.001 M EDTA) to obtain the PBS-buffered solution of the exemplary product ADC-8 of formula FADC-1 (1.47 mg/mL, 4.5 mL), which was stored at 4° C.

The average value calculated by UV-Vis: n=6.33.

Biological Assay

Test Example 1. Biacore Test for Antibody Affinity

The reaction affinity of anti-B7H3 antibody and B7H3-ADC to human 2Ig-B7H3 antigen and human 4Ig-B7H3 antigen was determined using a Biacore, GE instrument.

A biosensor chip Protein A (Cat. #29127556, GE) was used to affinity capture a certain amount of antibody/ADC to be tested. Series diluted human 2Ig-B7H3 antigen (Cat. #1949-B3-050/CF, R&D) and human 4Ig-B7H3 antigen (Cat. #11188-H08H, Sino Biological) were flowed through the surface of the chip. Real-time reaction signal was detected by using Biacore instrument (Biacore T200, GE) to obtain the association and dissociation curves. After completion of each cycle of dissociation, the biochip was washed and regenerated with glycine-hydrochloric acid regeneration solution (pH 1.5) (Cat. #BR-1003-54, GE). The buffer used in the experiment was HBS-EP buffer solution (pH 7.4) (Cat. #BR-1001-88, GE).

The experimental data was fitted with BIAevaluation version 4.1 GE software in a (1:1) Langmuir model to obtain affinity values. The experimental results are shown in Table 2.

TABLE 2

Reaction affinity between h1702 antibody and various antigens (unit: M)

| Antibody | Human 2Ig-B7H3 | Human 4Ig-B7H3 |
|---|---|---|
| h1702 | 7.97E−7 | 8.55E−9 |
| ADC-2 | | 7.55E−9 |

Conclusion: h1702 antibody has a strong affinity with antigens. At the same time, the Biacore affinity test with human 2Ig-B7H3 and human 4Ig-B7H3 shows that the affinity of ADC is similar to that of the naked antibody.

Test Example 2. In Vitro Endocytosis Test

In this experiment, the endocytosis effect of the antibody was evaluated based on the intensity of fluorescence signal of the intracellular antibody. The B7-H3 antibody and APC anti-human IgG Fc (Biolegend, 409306) were mixed at a molar ratio of 1:2 and incubated on ice for 15 minutes. The antibody mixture was incubated with $2 \times 10^5$ U87MG cells (human brain astroblastoma, Chinese Academy of Sciences cell bank, Catalog #TCHu138) on ice for 30 minutes, and excess antibody was removed by washing. The cells were transferred to a 37° C. prewarmed medium, and incubated at 37° C. for 0, 15, 30, 60 and 120 minutes respectively. The cells were centrifuged and resuspended in the antibody elution solution (0.05M glycine, 0.1M NaCl, pH 2.45). After incubating for 7 minutes at room temperature, the antibody elution solution was removed by washing, and the intracellular fluorescence signal was read using BD Verse (results shown in FIG. 1). The results show that h1702 was efficiently endocytosed into cells after binding to U87MG cells.

Test Example 3. $T_{1/2}$ Evaluation on SD Rats

4 SD rats (purchased from Shanghai JieSiJie Laboratory Animal Co., Ltd., half male and half female) were maintained in light/dark cycle adjusted at 12/12 hours, with constant temperature of 24±3° C., humidity of 50-60%, and free access to food and water. On the day of the experiment, SD rats were injected with the test agent B7H3 antibody/ADC respectively into tail vein at a dose of 3 mg/kg and an injection volume of 5 ml/kg.

The time point for blood collection: On the first day of administration, blood was taken from ocular fundus vein at 5 min, 8 h, 24 h (Day 2), Day 3, Day 5, Day 8, Day 11 and Day 15 after administration, each 200 µL (equivalent to 100 µL of serum). The collected blood samples were left to stand at room temperature for half an hour until coagulation, and then centrifuged at 10,000×g at 4° C. for 10 minutes. The supernatant was collected and immediately stored at −80° C.

The B7H3 antibody concentration in the serum was measured by ELISA, and PK analysis was performed. The results are shown in Table 3.

TABLE 3

$T_{1/2}$ of B7H3 antibody in SD rat

| Test agent | Administration mode | $T_{1/2}$ (average ± SD, hour) |
|---|---|---|
| h1702 | IV (3 mg/kg) | 185 ± 017 |

The results show that the half-life of h1702 of the present disclosure in rats is about 185 hours (7.7 days).

Test Example 4. Chemical Stability of the B7H3 Antibody

Chemical modification after antibody preparation is one of the common reasons leading to the product stability problem, especially the high degree of deamination, oxidation or isomerization modification at some amino acids in the CDR region. Those modifications should be avoided or reduced. 500 µg of the antibody to be tested was dissolved in 500 µl of PBS (pH 7.4), and subjected to a water bath at 40° C. Samples were taken at day 0, 10, and 20 respectively for enzymatic hydrolysis experiments. 100 µg of samples were taken at different time points and dissolved in 100 µl of 0.2 M His-HCl (histidine hydrochloride buffer) and 8 M Gua-HCl (pH 6.0, citrulline hydrochloride buffer). 3 µl of 0.1 g/mL DTT (dithiothreitol) was added, and subjected to water bath at 50° C. for 1 hour. The samples were ultra-filtered twice with 0.02 M His-HCl solution (pH 6.0), and 3 µL of 0.25 mg/mL trypsin (invitrogen, CAT#25200-072) was added. The mixture was subjected to enzymolysis overnight at 37° C. in a water bath. LC-MS was carried out using Agilent 6530 Q-TOF, and potential modification sites were analyzed by mass spectrometry (the results are shown in Table 4). The results show that the B7H3 antibody h1702 of the present disclosure has no significantly increased tendency towards deamidation, oxidation or heterogeneity, indicating that the antibody has excellent physical and chemical stability.

TABLE 4

Chemical stability of various antibodies

| Sample | Light chain/heavy chain | Site/ modification | Day 0 | Day 10 | Day 20 |
|---|---|---|---|---|---|
| h1702 | LC | M48/oxidation | 2.82% | 2.9% | 2.83% |
| | HC | M34/oxidation | 3.52% | 3.46% | 3.38% |
| | | M83/oxidation | 0.98% | 1.01% | 0.01% |

Test Example 5. Stability of h1702DS Antibody

The stability of h1702 and h1702DS was tested by SEC, non-reducing CE-SDS test method (pH 9.0) and IEX test method.

SEC test: Waters e2695 chromatograph and Xbridge BEH 200A SEC column were used. 50 µg of antibody was loaded, and eluted with PBS mobile phase in constant gradient.

CE-SDS Nr Method:
Samples were processed using the Beckman SDS-MW Analysis Kit. 100 µg of protein was added with a buffer solution, and heated to denature. Data was collected using PA800 capillary electrophoresis apparatus.

IEX Method:
Waters Acquity H-Class chromatograph and Thermo MAbPac SCX-10 column were used. 50 µg of the antibody was loaded, and a linear gradient was applied, using CX-1 pH Gradient Buffer Kit as the mobile phase. Ultraviolet signal at a wavelength of 280 nm was collected.

TABLE 5

Comparison of the stability of h1702 and h1702DS

| | SEC | CE-SDS (pH9.0) | IEX |
|---|---|---|---|
| h1702 | 100% | 71.21% | 40.5% |
| h1702DS | 100% | 94.67% | 86.21% |

Test Example 6: In Vitro Cell Proliferation Test

In this experiment, the inhibition effect of B7H3-ADC on cell proliferation was evaluated based on $IC_{50}$ by detecting the intracellular ATP content.

U87MG cells (human brain astroblastoma, Chinese Academy of Sciences cell bank, Catalog #TCHu138), Calu-6 cells (lung cancer cells, ATCC, Catalog #ATCC@ HTB-56™), Detroit562 cells (human pharyngeal carcinoma cells, ATCC, Catalog #ATCC@ CCL-138™) and A498 cells (kidney cancer cells, ATCC, Catalog #ATCC@ HTB-44™) were cultured in EMEM medium containing 10% FBS, and passaged 2 to 3 times a week with a passage ratio of 1:3 or 1:6. EMEM medium preparation: MEM medium (GE, CAT #SH30024.01), NEAA (sigma, CAT#M7145-100ML) and sodium pyruvate solution (sigma, CAT #S8636-100ML).

A-375 (melanoma cells, ATCC, Catalog #ATCC@ CRL-1619™) was cultured in DMEM (GE, SH30243.01) medium containing 10% FBS, and passaged 2 to 3 times a week with a passage ratio of 1:3 or 1:6.

CHO-K1 (which does not express human B7H3, ATCC, Catalog #ATCC@ CCL-61™) was cultured in F12 (Gibco, 11765-054) medium containing 10% FBS, and passaged 2 to 3 times a week with a passage ratio of 1:4 or 1:6.

For passage, the medium was removed and the cell layer was washed with 5 mL of 0.25% trypsin, then the trypsin was removed and the cells were digested for 3 to 5 minutes in an incubator. Then the cells were resuspended by the addition of fresh medium. The cells were counted, and the cell suspension was formulated to the corresponding density (U87MG cells: 500 cells/well; A-498 cells: 500 cells/well; A-375 cells: 300 cells/well; Calu-6 cells: 800 cells/well; detroit562 cells: 2000 cells/well; and CHO-K1 cells: 500 cells/well).

180 µL of cell suspension was added to a 96-well plate, and 200 µL of medium was added to the periphery of the 96-well plate. The plate was incubated for 24 hours in an incubator (37° C., 5% $CO_2$).

The samples to be tested were diluted with PBS or DMSO at a 3-fold ratio to 9 concentrations (the initial concentration of each ADC was 500 nM). The samples were added to the plate, which was incubated for 6 days in the incubator (37° C., 5% $CO_2$). 90 µl of CellTiter-Glo reagent was added to each well of the 96-well plate, and the plate was left to stand in the dark at room temperature for 10 minutes. The chemiluminescence signal value was read in Victor3, and the data was processed by GraphPad software. The measured $IC_{50}$ values are shown in Table 6 and FIGS. 2A to 2F.

TABLE 6

Inhibition effect of the ADC of the present disclosure on cell proliferation

|  | A498 | Calu-6 | U87 | A375 | Detroit562 | CHOK1 |
|---|---|---|---|---|---|---|
| ADC-2 | 418.9* | 70.6 | 49.1 | 33.3 | 31.6 | >500 |
| ADC-3 | 13.1 | 1.91 | 3.78 | 1.51 | 1.89 | 36.8 |
| ADC-1 | 196.6 | 26.54 | 29 | 23.72 | 26.9 | >500 |

*The unit is nM.

Test Example 7: Efficacy Evaluation of the ADC of the Present Disclosure on Human Brain Astroblastoma U87MG Xenograft Tumor in Nude Mice I. Test Purpose BALB/c nude mice were used as the test animal to evaluate the efficacy of the ADC compound of the present disclosure on human brain astroblastoma U87MG xenograft tumor in nude mice.

II. Test Drugs and Materials
1. Test Drugs
   ADC-5 (1mpk, 3mpk)
   ADC-8 (1mpk, 3mpk)
   Blank: PBS buffer solution (pH 7.4)
2. Formulation Method: PBS Buffer Solution (pH 7.4).
3. Test Animals
   BALB/c nude mice (SPF, female), purchased from Shanghai JieSiJie Laboratory Animal Co., Ltd.

III. Test Process

BALB/c nude mice (female, 6 to 7 weeks old) for test were inoculated subcutaneously with human brain astroblastoma U87MG cells (as defined above). On Day 10 after the inoculation, the animals were randomly grouped to 8 animals per group (DO), and the drugs were administered by intraperitoneal injection once a week for 3 times. The tumor volume and body weight were measured 2 to 3 times a week, and the data were recorded. The calculation formula of tumor volume (V) is as follows:

$$V = \tfrac{1}{2} \times a \times b^2$$

wherein:
a and b represent length and width respectively.
Relative volume $(RTV) = V_T/V_0$
Tumor inhibition rate $(\%) = (C_{RTV} - T_{RTV})/C_{RTV}$ (%)
wherein $V_0$ and $V_T$ represent the tumor volume at the beginning of the test and at the end of the test, respectively. $C_{RTV}$ and $T_{RTV}$ represent the relative tumor volume of the control group (blank) and the test group at the end of the test, respectively.

IV. Test Results

Intraperitoneal injection (i.p.) administration was carried out once a week for 3 times. On Day 18 of the observation, the tumor inhibition rate of ADC-8 1mpk reached 39.22% (P<0.01); the tumor inhibition rate of ADC-8 3mpk reached 80.24% (P<0.0001); the tumor inhibition rate of ADC-5 1mpk reached 27.53% (P<0.05); and the tumor inhibition rate of ADC-5 3mpk reached 55.88% (P<0.0001). On Day 22 (D22) of the observation, the tumor inhibition rate of each administration group was further improved, the tumor inhibition rate of ADC-8 1mpk reached 47.7% (P<0.0001); the tumor inhibition rate of ADC-8 3mpk reached 89.8% (P<0.0001); the tumor inhibition rate of ADC-5 1mpk reached 40.6% (P<0.0001); and the tumor inhibition rate of ADC-5 3mpk reached 63.3% (P<0.0001).

Figure 3:
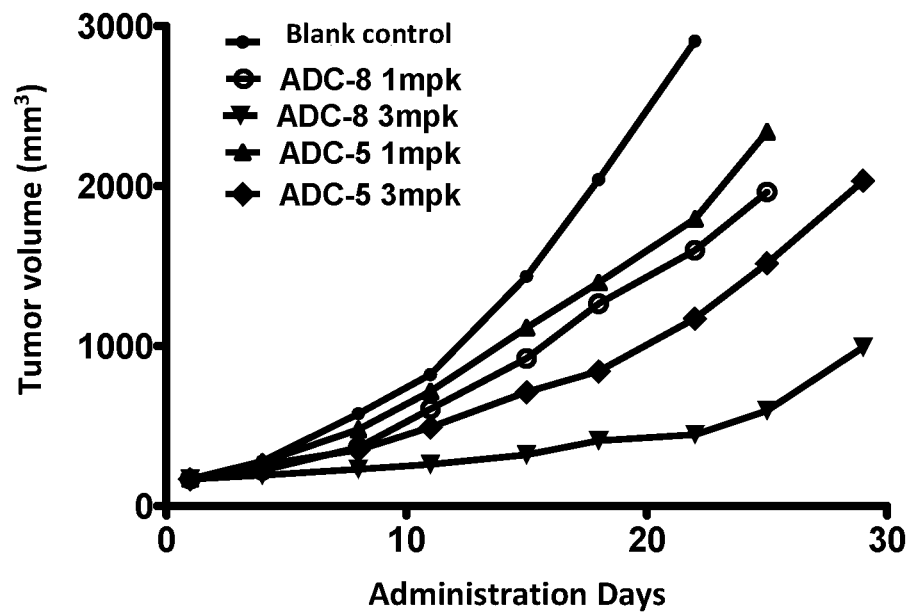
FIG. 3: The inhibitory effect of ADC-8 (1 mpk, 3 mpk) and ADC-5 (1 mpk, 3 mpk) of the present disclosure on U87MG xenograft tumor in nude mice upon intraperitoneal injection in Test Example 7.

During the administration, the animals in each group showed normal body weight, suggesting that the ADC has no obvious side effects. The test results are shown in Table 7 and FIG. 3. The tested antibodies can effectively inhibit the growth of U87MG xenograft tumor in tumor-bearing nude mice, in a dose-dependent manner.

TABLE 7

Efficacy of the ADC of the present disclosure on U87MG xenograft tumor in tumor-bearing nude mice (D22)

| Group | Average tumor volume (mm³) | | | | | | Relative tumor volume | | | | Tumor inhibition rate (%) | |
|---|---|---|---|---|---|---|---|---|---|---|---|---|
|  | D0 | SEM | D18 | SEM | D22 | SEM | D18 | SEM | D22 | SEM | D18 | D22 |
| Blank control | 167 | 18 | 2041 | 288 | 2907 | 328 | 12.01 | 0.97 | 17.76 | 1.63 | — | — |
| ADC-8 1 mpk | 168 | 18 | 1264 | 222 | 1599 | 271 | 7.30 | 0.91 | 9.19 | 0.99 | 39.22** | 47.7*** |
| ADC-8 3 mpk | 168 | 17 | 409 | 73 | 448 | 89 | 2.37 | 0.32 | 2.55 | 0.37 | 80.24*** | 89.8*** |
| ADC-5 1 mpk | 168 | 16 | 1397 | 81 | 1795 | 111 | 8.71 | 0.70 | 11.25 | 1.02 | 27.53* | 40.6*** |
| ADC-5 3 mpk | 168 | 16 | 842 | 42 | 1172 | 80 | 5.30 | 0.42 | 7.55 | 0.95 | 55.88* | 63.3* | vs blank: *p < 0.05, p < 0.01, *p < 0.001

Test Example 8: Efficacy Evaluation of the ADC of the Present Disclosure on Human Pharyngeal Carcinoma Pleural Fluid Metastatic Cell Detroit562 Xenograft Tumor in Nude Mice I. Test Purpose BALB/c nude mice were used as the test animal to evaluate the efficacy of the ADC compound of the present disclosure on human pharyngeal carcinoma pleural fluid metastatic cell Detroit 562 xenograft tumor in nude mice.

II. Test Drugs and Materials

1. Test Drugs

ADC-1 (1mpk, 3mpk)

ADC-2 (1mpk, 3mpk)

Negative control ADC (3mpk): ligand-toxin conjugate formed by coupling of a non-B7H3 target with a reference compound (Example 58 in patent application "CN104755494A").

2. Formulation Method: The Drugs were all Diluted and Formulated with PBS.

3. Test Animals

BALB/c nude nude mice, purchased from Changzhou Cavens Laboratory Animal Co., Ltd.

III. Test Process

BALB/c nude mice (female, 6 to 7 weeks old) for test were inoculated subcutaneously with human pharyngeal carcinoma pleural fluid metastatic cell Detroit 562 cells. On Day 10 after the inoculation, the animals were randomly grouped with 8 animals per group (D0), and the drugs were administered by intraperitoneal injection once a week for 3 times. The tumor volume and body weight were measured 2 to 3 times a week, and the data were recorded. The calculation formula of tumor volume (V) is as follows:

$$V = \tfrac{1}{2} \times a \times b^2$$

wherein:

a and b represent length and width respectively.

Relative volume (RTV)=$V_T/V_0$

Tumor inhibition rate (%)=$(C_{RTV}-T_{RTV})/C_{RTV}$ (%)

wherein $V_0$ and $V_T$ represent the tumor volume at the beginning of the test and at the end of the test, respectively. $C_{RTV}$ and $T_{RTV}$ represent the relative tumor volume of the control group (negative control) and the test group at the end of the test, respectively.

IV. Test Results

Intraperitoneal injection administration was carried out once a week for 3 times. On Day 28 of the observation, the tumor inhibition rate of ADC-1 1 mg/kg (1mpk) reached 40.85%; the tumor inhibition rate of ADC-1 3 mg/kg (3mpk) reached 62.55% (P<0.05); the tumor inhibition rate of ADC-2 1 mg/kg (1mpk) reached 44.26%; and the tumor inhibition rate of ADC-2 3 mg/kg (3mpk) reached 72.27% (P<0.01).

Figure 4:
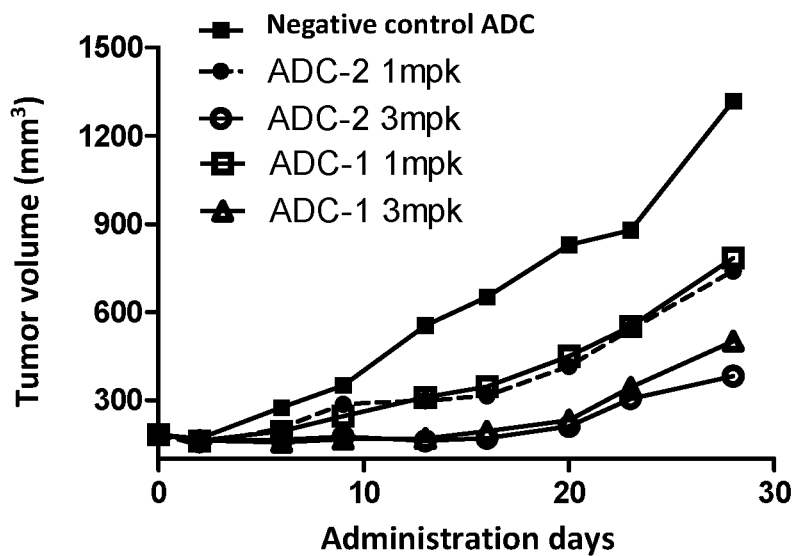
FIG. 4: The inhibitory effect of ADC-2(1 mpk, 3 mpk) and ADC-1 (1 mpk, 3 mpk) of the present disclosure on Detroit562 xenograft tumor in nude mice upon intraperitoneal injection in Test Example 8.

During the administration, the animals in each group show normal body weights, suggesting that the ADC has no obvious side effects. The test results are shown in Table 8 and FIG. 4. The tested antibodies can effectively inhibit the growth of Detroit 562 xenograft tumor in tumor-bearing nude mice, and show a dose-dependent manner.

TABLE 8

Efficacy of the ADC of the present disclosure on Detroit 562 xenograft tumor in tumor-bearing nude mice (D28)

| Group | Average tumor volume ($mm^3$) Day 0 | SEM | Average tumor volume ($mm^3$) Day 28 | SEM | Relative tumor volume Day 28 | SEM | Tumor inhibition rate (%) on Day 28 |
|---|---|---|---|---|---|---|---|
| Negative control | 182.70 | 6.79 | 1317.99 | 223.20 | 7.47 | 1.46 | — |
| ADC-1 1 mpk | 182.46 | 6.45 | 784.30 | 136.27 | 4.42 | 0.80 | 40.85 |
| ADC-1 3 mpk | 182.60 | 6.38 | 501.07 | 123.58 | 2.80 | 0.68 | 62.55* |
| ADC-2 1 mpk | 182.65 | 6.53 | 738.73 | 152.08 | 4.16 | 0.87 | 44.26 |
| ADC-2 3 mpk | 182.59 | 6.50 | 381.48 | 105.76 | 2.07 | 0.58 | 72.27** |

Test Example 9: In Vitro Cell Proliferation of ADCs with Various Drug Loadings

The efficacy of ADC compounds of formula FADC-2, ADC-4 (n=6.87), ADC-6 (n=2.97) and ADC-7 (n=4.8) was determined in in vitro cell proliferation test according to the experimental procedures as same as Test Example 6.

Figure 5A:
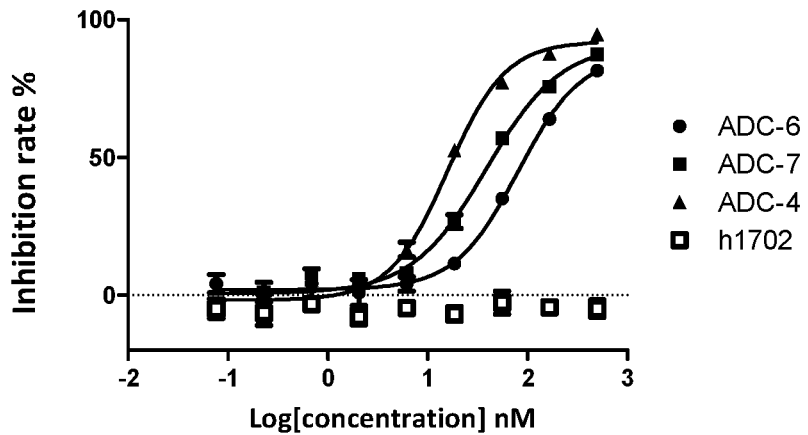
FIG. 5A: The proliferation inhibition rate of ADC-4, ADC-6 and ADC-7 of the present disclosure on Detroit562 cells in Test Example 9.
Figure 5B:
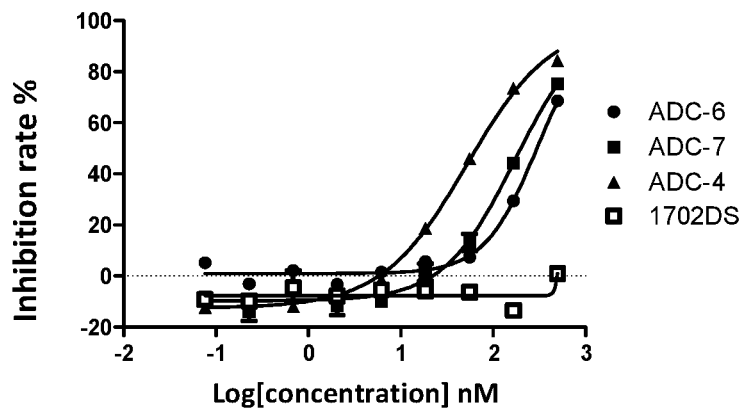
FIG. 5B: The proliferation inhibition rate of ADC-4, ADC-6 and ADC-7 of the present disclosure on Calu-6 cells in Test Example 9.
Figure 5C:
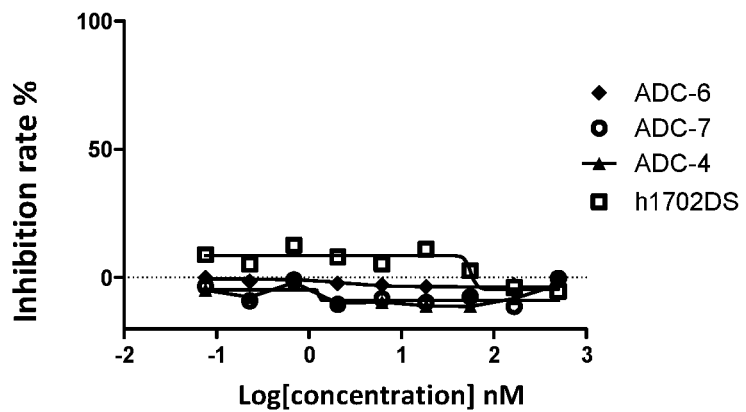
FIG. 5C: The proliferation inhibition rate of ADC-4, ADC-6 and ADC-7 of the present disclosure on CHOK1 cells in Test Example 9.

The measured $IC_{50}$ value and maximum inhibition rate are shown in Table 9 and FIGS. 5A, 5B and 5C. FADC-2 with various DAR values show an effect on inhibiting cell proliferation, and the inhibition effect is positively correlated with the DAR value, while the naked antibody shows no effect on inhibiting cell proliferation.

TABLE 9

| ADC | Detroit562 IC50 (nM) | Detroit562 Maximum inhibition rate (%) | Calu-6 (as defined above) IC50 (nM) | Calu-6 (as defined above) Maximum inhibition rate (%) | CHOK1 (as defined above) IC50 (nM) | CHOK1 (as defined above) Maximum inhibition rate (%) |
|---|---|---|---|---|---|---|
| ADC-6 | 80.4 | 81.59 | 321.5 | 64.60 | >500 | 2.15 |
| ADC-7 | 38.9 | 87.45 | 148.1 | 77.62 | >500 | -2.05 |
| ADC-4 | 15.9 | 94.64 | 53.6 | 84.44 | >500 | 9.09 |
| h1702DS | >500 | -2.77 | >500 | 0.99 | >500 | 12.62 |

Test Example 10: Plasma Stability

ADC-4 sample was thoroughly mixed with human plasma, monkey plasma (Shanghai Medicilon Inc.) and 1% BSA (Sigma) PBS solution (Sangon Biotech (Shanghai) Co., Ltd.) respectively at a final concentration of 100 μg/ml, and filtered for sterilization. The mixture was incubated in a water bath at 37° C., and the starting day of incubation was recorded as Day 0. Samples were collected at Day 7, Day 14 and Day 21 for free toxin detection.

Samples collected at different time points were cooled to room temperature, and mixed well by vortex. 25 μl of sample was added to a 96-well plate. 50 μL of internal standard working solution (100 ng/mL camptothecin in acetonitrile) and 150 μl of acetonitrile were added. The solution was vortexed for 5 minutes, and centrifuged for 10 minutes (4000 rpm). 5 μl of the solution was taken out for LC/MS/MS (Applied Biosystems, Inc., USA) analysis.

Figure 6:
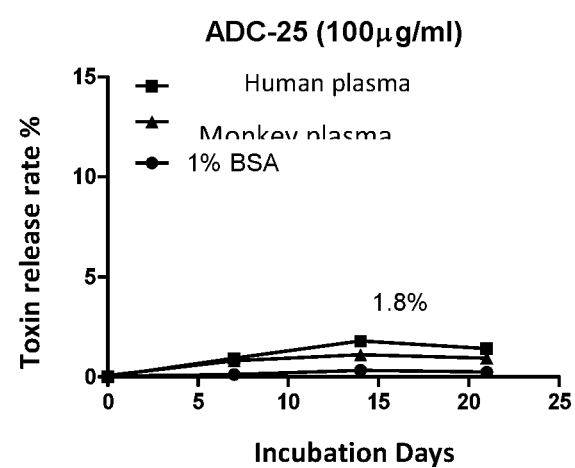
FIG. 6: Plasma stability test results of ADC-4 of the present disclosure in Test Example 10.

The results are shown in FIG. 6. ADC-4 is quite stable in human plasma, monkey plasma and 1% BSA PBS solution. The release rate of free toxin does not exceed 2%, and become stable on Day 14.

What is claimed is:

1. A ligand-drug conjugate of formula (Pc-L$_b$-Y-Dr) or a pharmaceutically acceptable salt or solvate thereof:

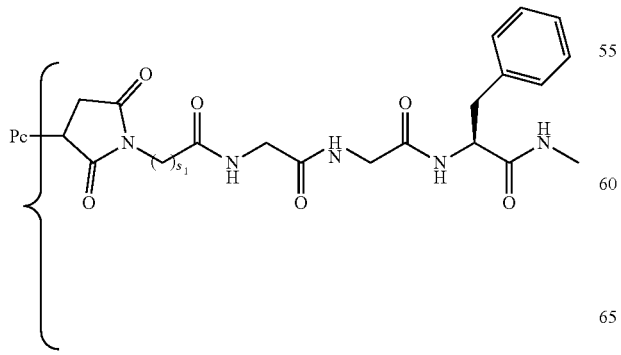

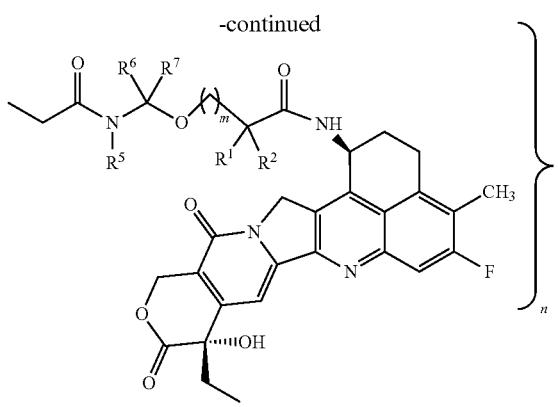

(Pc-L$_b$-Y-Dr)

wherein:
R1 and R2 together with the carbon atom to which they are attached form a cyclopropyl;

R5 is a hydrogen atom;
R6 and R7 are each a hydrogen atom;
s1 is 5;
m is 0;
n is an integer from 1 to 10;
Pc is an anti-B7H3 antibody or an antigen-binding fragment thereof comprising:
a heavy chain variable region (VH) comprising the amino acid sequence set forth in SEQ ID NO: 8 (HCDR1), the amino acid sequence set forth in SEQ ID NO: 9 (HCDR2), and the amino acid sequence set forth in SEQ ID NO: 10 (HCDR3) and
a light chain variable region (VL) comprising the amino acid sequence set forth in SEQ ID NO: 11 (LCDR1), the amino acid sequence set forth in SEQ ID NO: 12 (LCDR2), and the amino acid sequence set forth in SEQ ID NO: 13 (LCDR3).

2. The ligand-drug conjugate of formula (Pc-$L_b$-Y-Dr) or the pharmaceutically acceptable salt or solvate thereof according to claim 1, wherein the VH comprises human framework regions, and the VL comprises human framework regions.

3. The ligand-drug conjugate of formula (Pc-$L_b$-Y-Dr) or the pharmaceutically acceptable salt or solvate thereof according to claim 1, wherein the VH comprises the amino acid sequence set forth in SEQ ID NO: 6, and the VL comprises the amino acid sequence set forth in SEQ ID NO: 7.

4. The ligand-drug conjugate of formula (Pc-$L_b$-Y-Dr) or the pharmaceutically acceptable salt or solvate thereof according to claim 1, wherein the VH comprises the amino acid sequence set forth in SEQ ID NO: 6, and the VL comprises the amino acid sequence set forth in SEQ ID NO: 17.

5. The ligand-drug conjugate of formula (Pc-$L_b$-Y-Dr) or the pharmaceutically acceptable salt or solvate thereof according to claim 1, wherein the anti-B7H3 antibody or the antigen-binding fragment thereof comprises a heavy chain comprising a human IgG1, IgG2, IgG3 or IgG4 constant region and a light chain comprising a human kappa or lambda light chain constant region.

6. The ligand-drug conjugate of formula (Pc-$L_b$-Y-Dr) or the pharmaceutically acceptable salt or solvate thereof according to claim 1, wherein the anti-B7H3 antibody comprises:
i) a heavy chain comprising the amino acid sequence set forth in SEQ ID NO: 14, and a light chain comprising the amino acid sequence set forth in SEQ ID NO: 15; or
ii) a heavy chain comprising the amino acid sequence set forth in SEQ ID NO: 14, and a light chain comprising the amino acid sequence set forth in SEQ ID NO: 16.

7. The ligand-drug conjugate of formula (Pc-$L_b$-Y-Dr) or the pharmaceutically acceptable salt or solvate thereof according to claim 1, wherein the antigen-binding fragment is selected from the group consisting of: Fab, Fab', F(ab')2, and scFv.

8. The ligand-drug conjugate of formula (Pc-$L_b$-Y-Dr) or the pharmaceutically acceptable salt or solvate thereof according to claim 1, wherein n is an integer from 2 to 8.

9. The ligand-drug conjugate of formula (Pc-$L_b$-Y-Dr) or the pharmaceutically acceptable salt or solvate thereof according to claim 8:

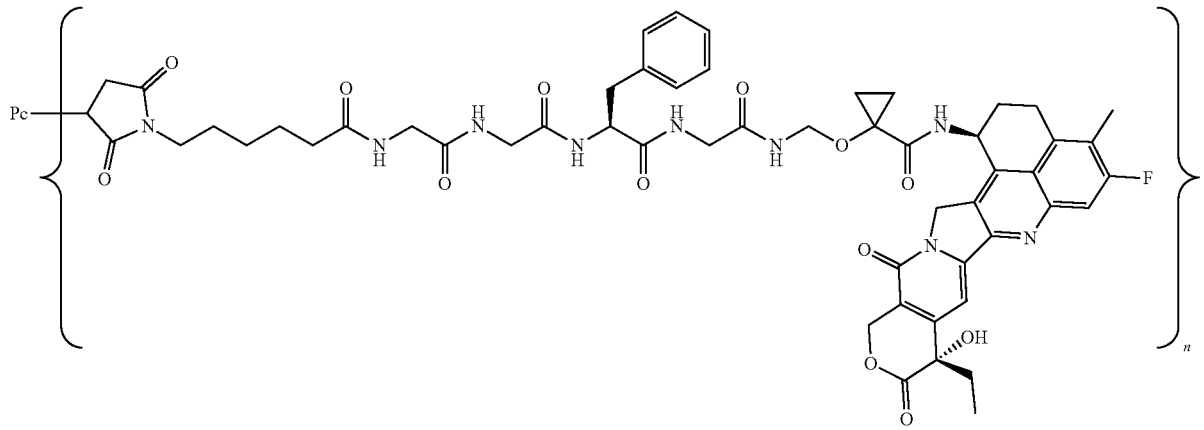

wherein the anti-B7H3 antibody or the antigen-binding fragment thereof comprises a heavy chain comprising the amino acid sequence set forth in SEQ ID NO: 14 and a light chain comprising the amino acid sequence set forth in SEQ ID NO: 16.

10. A pharmaceutical composition, comprising the ligand-drug conjugate or the pharmaceutically acceptable salt or solvate thereof according to claim 1, and a pharmaceutically acceptable excipient, diluent, and/or carrier.

11. A method of treating a human having a B7H3-mediated disease or disorder, the method comprising: administering to the human a therapeutically effective amount of the ligand-drug conjugate or the pharmaceutically acceptable salt or solvate thereof according to claim 1.

12. A ligand-drug conjugate of formula (Pc-L$_b$-Y-Dr) or a pharmaceutically acceptable salt or solvate thereof:

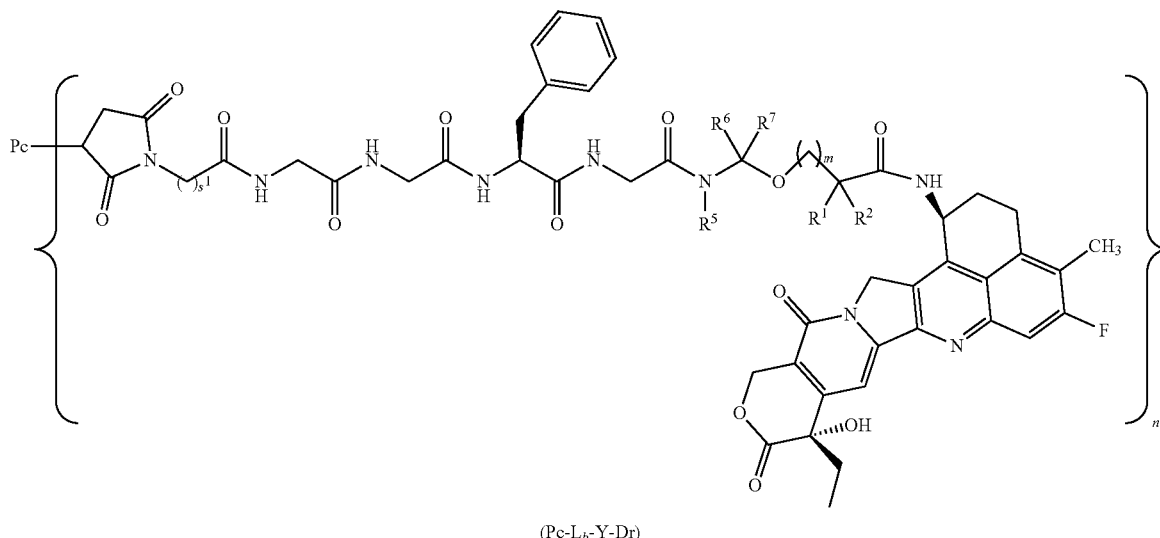

(Pc-L$_b$-Y-Dr)

wherein:
R$^1$ is cyclopropylalkyl;
R$^2$ is a hydrogen atom;
R$^5$ is a hydrogen atom;
R$^6$ and R$^7$ are each a hydrogen atom;
s$^1$ is 5;
m is 0;
n is an integer from 1 to 10;
Pc is an anti-B7H3 antibody or an antigen-binding fragment thereof comprising:
a heavy chain variable region (VH) comprising the amino acid sequence set forth in SEQ ID NO: 8 (HCDR1), the amino acid sequence set forth in SEQ ID NO: 9 (HCDR2), and the amino acid sequence set forth in SEQ ID NO: 10 (HCDR3) and
a light chain variable region (VL) comprising the amino acid sequence set forth in SEQ ID NO: 11 (LCDR1), the amino acid sequence set forth in SEQ ID NO: 12 (LCDR2), and the amino acid sequence set forth in SEQ ID NO: 13 (LCDR3).

13. The ligand-drug conjugate of formula (Pc-L$_b$-Y-Dr) or the pharmaceutically acceptable salt or solvate thereof according to claim 12, wherein the VH comprises human framework regions, and the VL comprises human framework regions.

14. The ligand-drug conjugate of formula (Pc-L$_b$-Y-Dr) or the pharmaceutically acceptable salt or solvate thereof according to claim 12, wherein the VH comprises the amino acid sequence set forth in SEQ ID NO: 6, and the VL comprises the amino acid sequence set forth in SEQ ID NO: 7.

15. The ligand-drug conjugate of formula (Pc-L$_b$-Y-Dr) or the pharmaceutically acceptable salt or solvate thereof according to claim 12, wherein the VH comprises the amino acid sequence set forth in SEQ ID NO: 6, and the VL comprises the amino acid sequence set forth in SEQ ID NO: 17.

16. The ligand-drug conjugate of formula (Pc-L$_b$-Y-Dr) or the pharmaceutically acceptable salt or solvate thereof according to claim 12, wherein the anti-B7H3 antibody or the antigen-binding fragment thereof comprises a heavy chain comprising a human IgG1, IgG2, IgG3 or IgG4 constant region and a light chain comprising a human kappa or lambda light chain constant region.

17. The ligand-drug conjugate of formula (Pc-L$_b$-Y-Dr) or the pharmaceutically acceptable salt or solvate thereof according to claim 12, wherein the anti-B7H3 antibody comprises:
  i) a heavy chain comprising the amino acid sequence set forth in SEQ ID NO: 14, and a light chain comprising the amino acid sequence set forth in SEQ ID NO: 15; or
  ii) a heavy chain comprising the amino acid sequence set forth in SEQ ID NO: 14, and a light chain comprising the amino acid sequence set forth in SEQ ID NO: 16.

18. The ligand-drug conjugate of formula (Pc-L$_b$-Y-Dr) or the pharmaceutically acceptable salt or solvate thereof according to claim 12, wherein the antigen-binding fragment is selected from the group consisting of: Fab, Fab', F(ab')2, and scFv.

19. The ligand-drug conjugate of formula (Pc-L$_b$-Y-Dr) or the pharmaceutically acceptable salt or solvate thereof according to claim 12, wherein n is an integer from 2 to 8.

20. The ligand-drug conjugate of formula (Pc-L$_b$-Y-Dr) or the pharmaceutically acceptable salt or solvate thereof according to claim 12, having the formula:
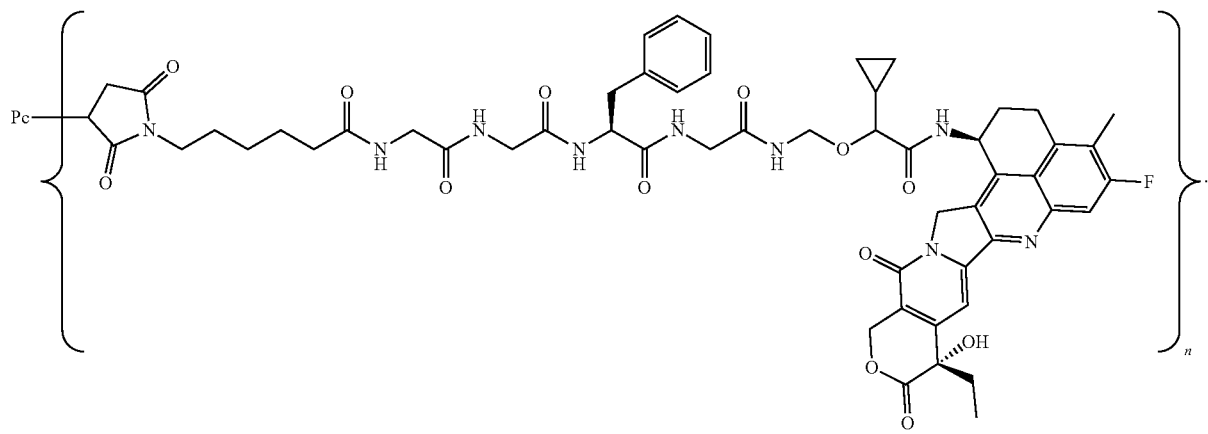
21. The ligand-drug conjugate of formula (Pc-L$_b$-Y-Dr) or the pharmaceutically acceptable salt or solvate thereof according to claim 12, having the formula selected from:
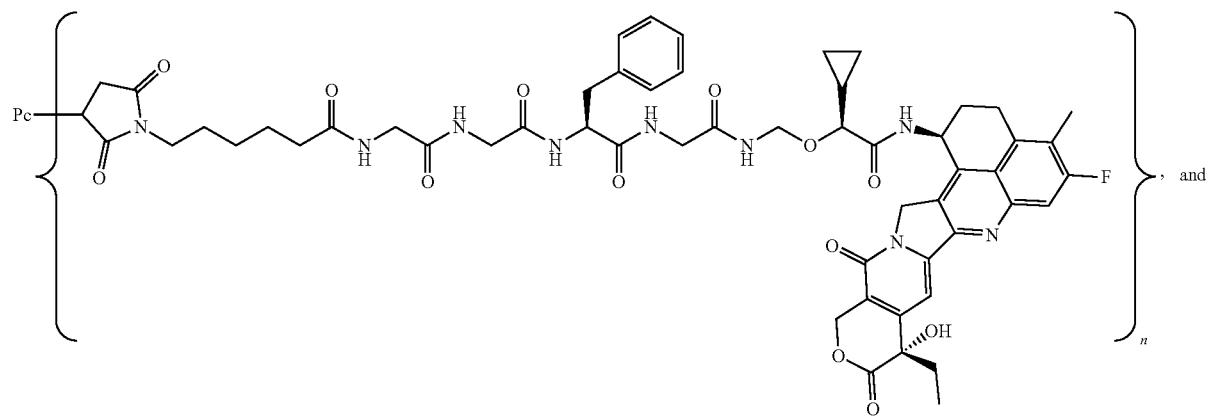, and
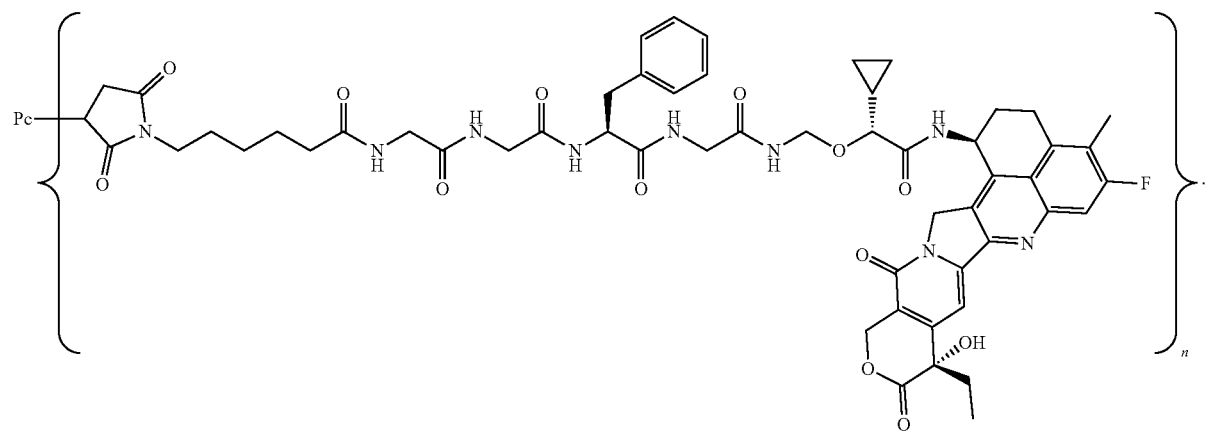

22. The ligand-drug conjugate of formula (Pc-L$_b$-Y-Dr) or the pharmaceutically acceptable salt or solvate thereof according to claim 21, having the formula selected from:

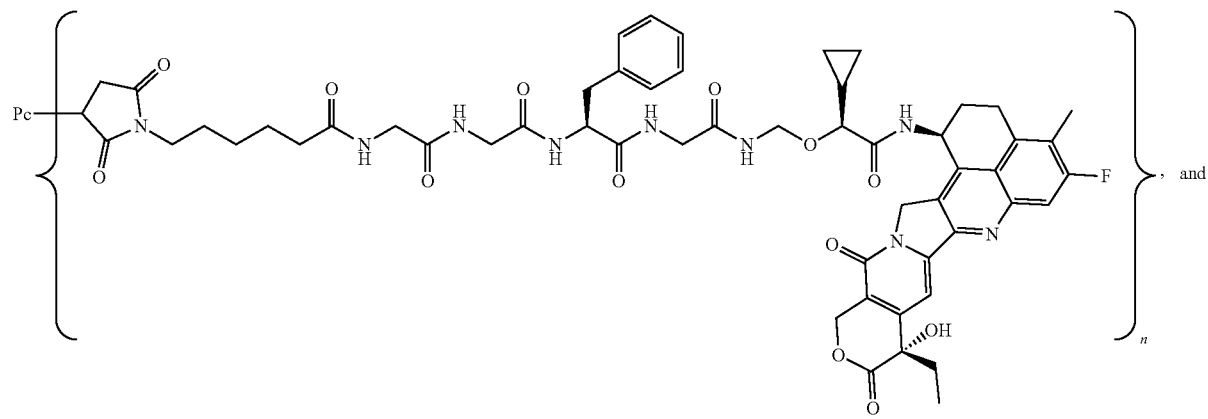

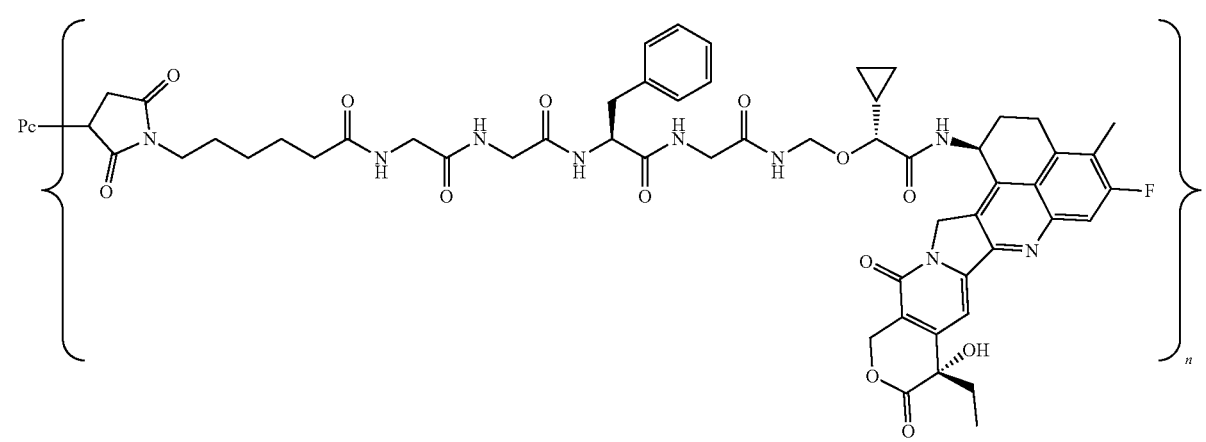

wherein the anti-B7H3 antibody or the antigen-binding fragment thereof comprises a heavy chain comprising the amino acid sequence set forth in SEQ ID NO: 14 and a light chain comprising the amino acid sequence set forth in SEQ ID NO: 16.

23. A pharmaceutical composition, comprising the ligand-drug conjugate or the pharmaceutically acceptable salt or solvate thereof according to claim 12, and a pharmaceutically acceptable excipient, diluent, and/or carrier.

24. A method of treating a human having a B7H3-mediated disease or disorder, the method comprising: administering to the human a therapeutically effective amount of the ligand-drug conjugate or the pharmaceutically acceptable salt or solvate thereof according to claim 12.

25. A ligand-drug conjugate of formula (Pc-L$_b$-Y-Dr) or a pharmaceutically acceptable salt or solvate thereof, having the formula:

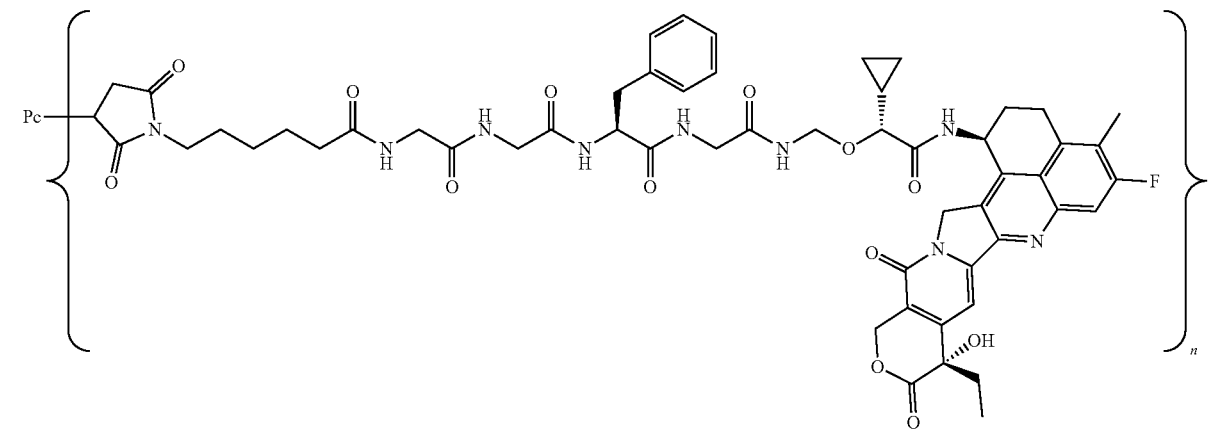

wherein
n is an integer from 1 to 10; and
Pc is an anti-B7H3 antibody or an antigen-binding fragment thereof, comprising a heavy chain variable region having the amino acid sequence set forth in SEQ ID NO: 6, and a light chain variable region having the amino acid sequence set forth in SEQ ID NO: 7.

26. A ligand-drug conjugate of formula (Pc-L$_b$-Y-Dr) or a pharmaceutically acceptable salt or solvate thereof, having the formula:

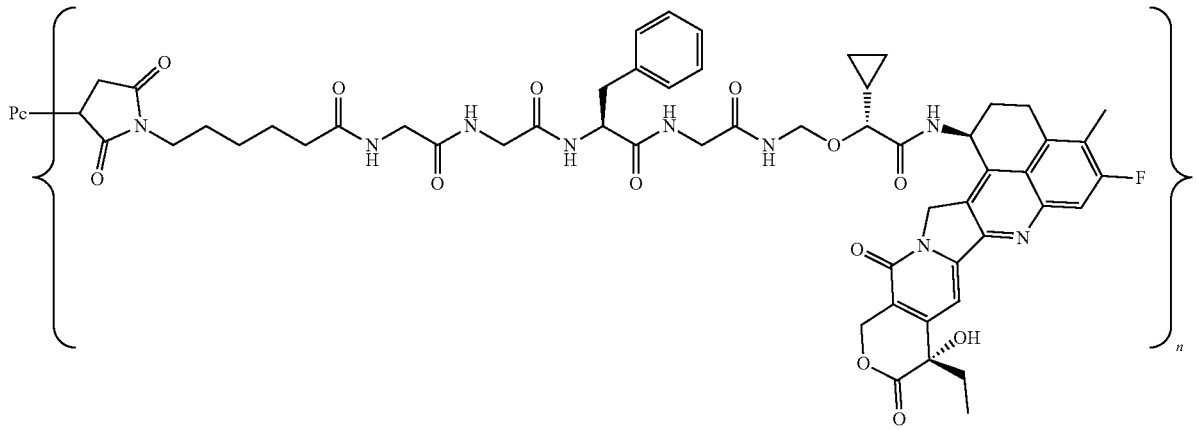

wherein
n is an integer from 1 to 10; and
Pc is an anti-B7H3 antibody or an antigen-binding fragment thereof, comprising a heavy chain variable region having the amino acid sequence set forth in SEQ ID NO: 6, and a light chain variable region having the amino acid sequence set forth in SEQ ID NO: 17.

27. A ligand-drug conjugate of formula (Pc-L$_b$-Y-Dr) or a pharmaceutically acceptable salt or solvate thereof, having the formula:

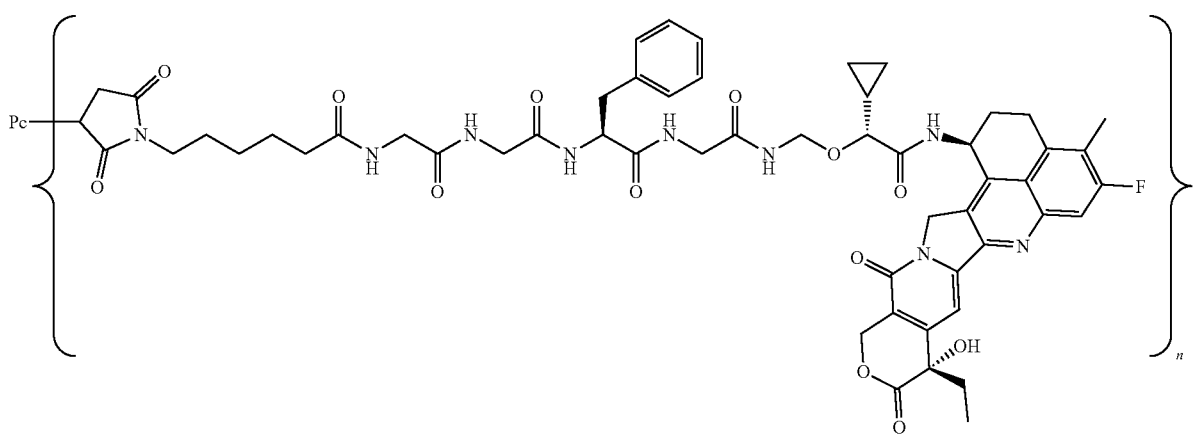

wherein
n is an integer from 1 to 10; and
Pc is an anti-B7H3 antibody or an antigen-binding fragment thereof, comprising a heavy chain comprising the amino acid sequence set forth in SEQ ID NO: 14, and a light chain comprising the amino acid sequence set forth in SEQ ID NO: 16.

28. A ligand-drug conjugate of formula (Pc-L$_b$-Y-Dr) or a pharmaceutically acceptable salt or solvate thereof:

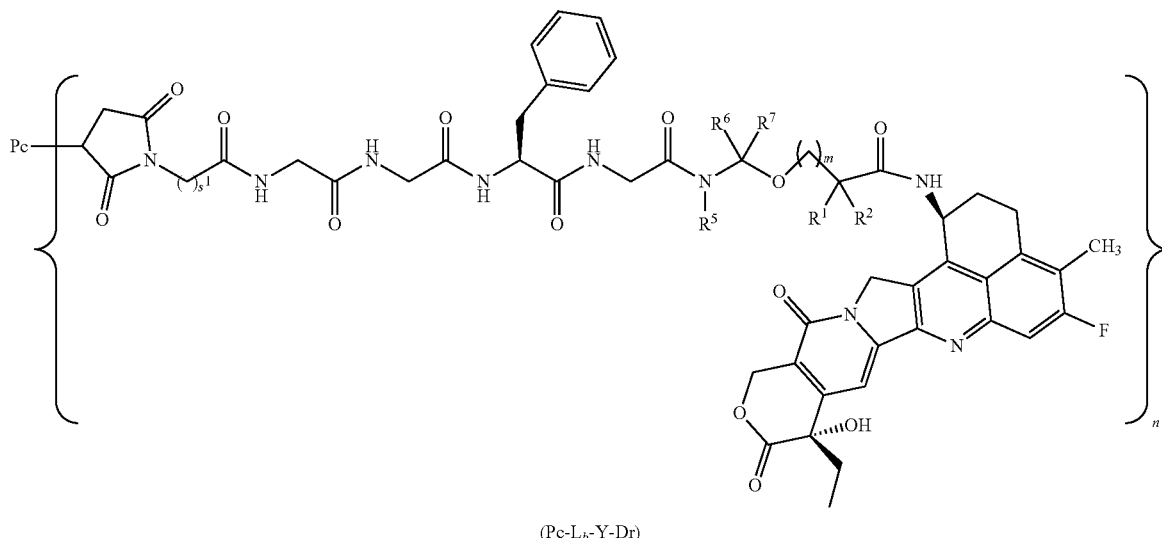

(Pc-L$_b$-Y-Dr)

wherein:
R1 is CF3;
R2 is a hydrogen atom;
R5 is a hydrogen atom;
R6 and R7 are each a hydrogen atom; s1 is 5;
m is 0;
n is an integer from 1 to 10;
Pc is an anti-B7H3 antibody or an antigen-binding fragment thereof comprising:
a heavy chain variable region (VH) comprising the amino acid sequence set forth in SEQ ID NO: 8 (HCDR1), the amino acid sequence set forth in SEQ ID NO: 9 (HCDR2), and the amino acid sequence set forth in SEQ ID NO: 10 (HCDR3) and
a light chain variable region (VL) comprising the amino acid sequence set forth in SEQ ID NO: 11 (LCDR1), the amino acid sequence set forth in SEQ ID NO: 12 (LCDR2), and the amino acid sequence set forth in SEQ ID NO: 13 (LCDR3).

29. The ligand-drug conjugate of formula (Pc-L$_b$-Y-Dr) or the pharmaceutically acceptable salt or solvate thereof according to claim 28, wherein the VH comprises human framework regions, and the VL comprises human framework regions.

30. The ligand-drug conjugate of formula (Pc-L$_b$-Y-Dr) or the pharmaceutically acceptable salt or solvate thereof according to claim 28, wherein the VH comprises the amino acid sequence set forth in SEQ ID NO: 6, and the VL comprises the amino acid sequence set forth in SEQ ID NO: 7.

31. The ligand-drug conjugate of formula (Pc-L$_b$-Y-Dr) or the pharmaceutically acceptable salt or solvate thereof according to claim 28, wherein the VH comprises the amino acid sequence set forth in SEQ ID NO: 6, and the VL comprises the amino acid sequence set forth in SEQ ID NO: 17.

32. The ligand-drug conjugate of formula (Pc-L$_b$-Y-Dr) or the pharmaceutically acceptable salt or solvate thereof according to claim 28, wherein the anti-B7H3 antibody or the antigen-binding fragment thereof comprises a heavy chain comprising a human IgG1, IgG2, IgG3 or IgG4 constant region and a light chain comprising a human kappa or lambda light chain constant region.

33. The ligand-drug conjugate of formula (Pc-L$_b$-Y-Dr) or the pharmaceutically acceptable salt or solvate thereof according to claim 28, wherein the anti-B7H3 antibody comprises:
i) a heavy chain comprising the amino acid sequence set forth in SEQ ID NO: 14, and a light chain comprising the amino acid sequence set forth in SEQ ID NO: 15; or
ii) a heavy chain comprising the amino acid sequence set forth in SEQ ID NO: 14, and a light chain comprising the amino acid sequence set forth in SEQ ID NO: 16.

34. The ligand-drug conjugate of formula (Pc-L$_b$-Y-Dr) or the pharmaceutically acceptable salt or solvate thereof according to claim 28, wherein the antigen-binding fragment is selected from the group consisting of: Fab, Fab', F(ab')$_2$, and scFv.

35. The ligand-drug conjugate of formula (Pc-L$_b$-Y-Dr) or the pharmaceutically acceptable salt or solvate thereof according to claim 28, wherein n is 2 to 8, and n is an integer.

36. The ligand-drug conjugate of formula (Pc-L$_b$-Y-Dr) or the pharmaceutically acceptable salt or solvate thereof according to claim 28, selected from the group consisting of:
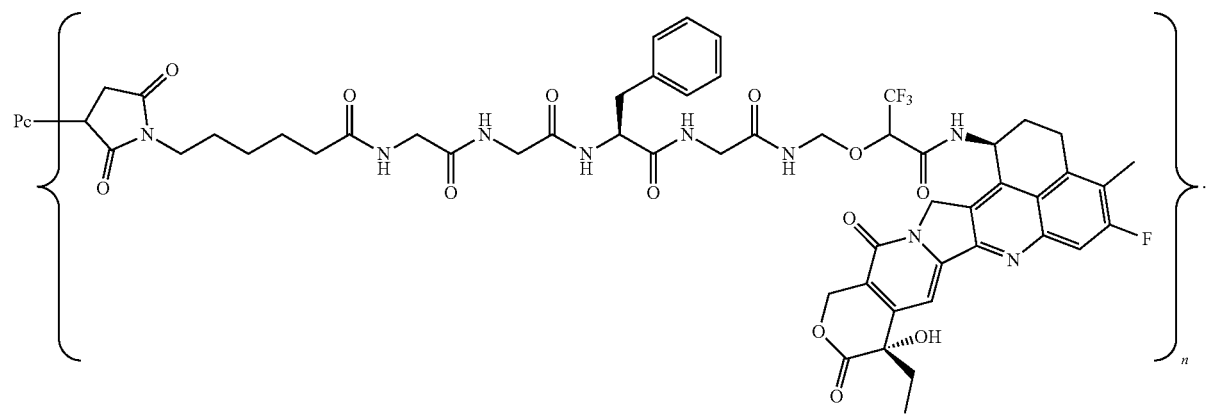
37. The ligand-drug conjugate of formula (Pc-L$_b$-Y-Dr) or the pharmaceutically acceptable salt or solvate thereof according to claim 28, selected from the group consisting of:
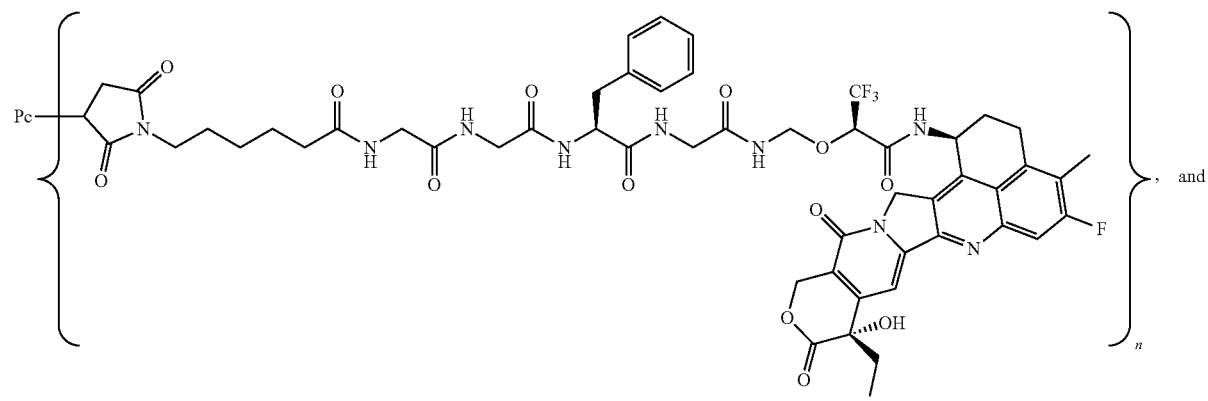
, and
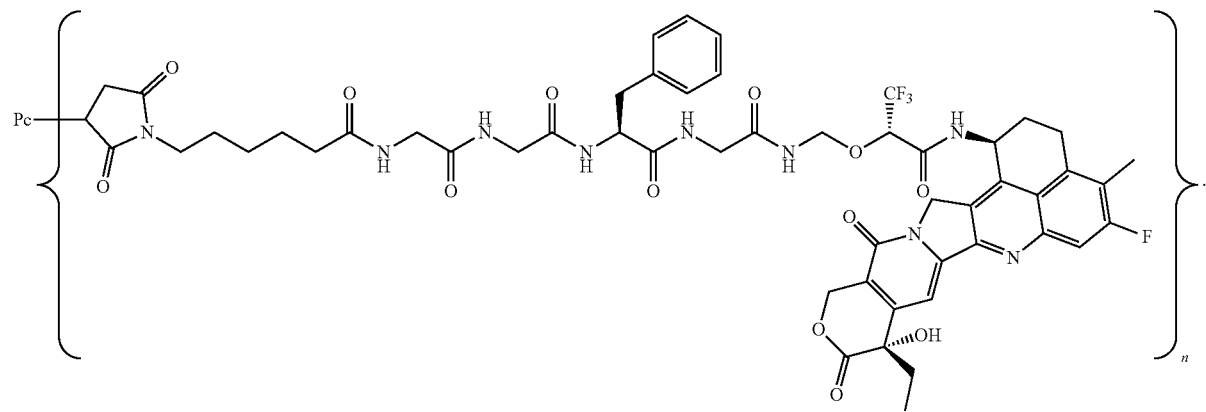

38. The ligand-drug conjugate of formula (Pc-L$_b$-Y-Dr) or the pharmaceutically acceptable salt or solvate thereof according to claim 37, selected from the group consisting of:

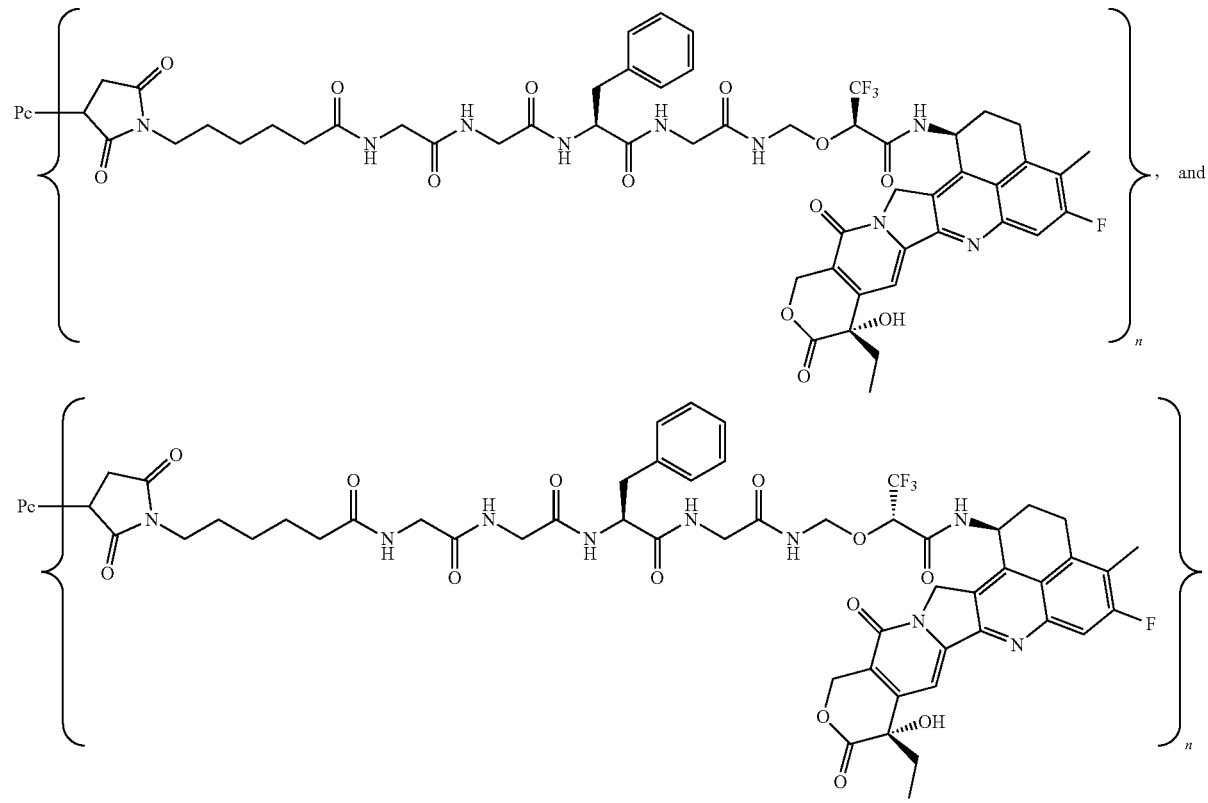

wherein
the anti-B7H3 antibody or the antigen-binding fragment thereof comprises a heavy chain comprising the amino acid sequence set forth in SEQ ID NO: 14 and a light chain comprising the amino acid sequence set forth in SEQ ID NO: 16.

39. A pharmaceutical composition, comprising the ligand-drug conjugate or the pharmaceutically acceptable salt or solvate thereof according to claim 28, and a pharmaceutically acceptable excipient, diluent, and/or carrier.

40. A method of treating a human having a B7H3-mediated disease or disorder, the method comprising: administering to the human a therapeutically effective amount of the ligand-drug conjugate or the pharmaceutically acceptable salt or solvate thereof according to claim 28.

* * * * *